(12) United States Patent
Sakagami et al.

(10) Patent No.: US 9,291,807 B2
(45) Date of Patent: Mar. 22, 2016

(54) IMAGE ACQUISITION DEVICE AND IMAGE ACQUISITION METHOD

(71) Applicant: Sony Corporation, Tokyo (JP)

(72) Inventors: Junichi Sakagami, Tokyo (JP); Kenji Tanaka, Tokyo (JP); Seiji Wada, Kanagawa (JP); Kenji Yamane, Kanagawa (JP)

(73) Assignee: Sony Corporation, Tokyo (JP)

( * ) Notice: Subject to any disclaimer, the term of this patent is extended or adjusted under 35 U.S.C. 154(b) by 0 days.

(21) Appl. No.: 14/559,161

(22) Filed: Dec. 3, 2014

(65) Prior Publication Data

US 2015/0160449 A1 Jun. 11, 2015

(30) Foreign Application Priority Data

Dec. 10, 2013 (JP) ................................. 2013-255066

(51) Int. Cl.
*G02B 21/16* (2006.01)
*G02B 21/36* (2006.01)
*G01N 21/64* (2006.01)
*G01J 3/44* (2006.01)

(52) U.S. Cl.
CPC ............ *G02B 21/361* (2013.01); *G01J 3/4406* (2013.01); *G01N 21/6458* (2013.01); *G02B 21/16* (2013.01); *G01N 2021/6419* (2013.01); *G01N 2021/6441* (2013.01); *G01N 2201/1053* (2013.01)

(58) Field of Classification Search
CPC ................ G01N 21/6458; G01N 2201/06113; G02B 21/361; G02B 21/16
See application file for complete search history.

(56) References Cited

U.S. PATENT DOCUMENTS

| 6,051,835 A | * | 4/2000 | Pettipiece et al. | ....... 250/339.09 |
| 2004/0069857 A1 | * | 4/2004 | Leblans et al. | ................ 235/494 |
| 2013/0169966 A1 | * | 7/2013 | Shchegrov et al. | ........... 356/369 |

FOREIGN PATENT DOCUMENTS

JP 2012-008261 A 6/2010

* cited by examiner

*Primary Examiner* — David Porta
*Assistant Examiner* — Faye Boosalis
(74) *Attorney, Agent, or Firm* — Wolf, Greenfield & Sacks, P.C.

(57) ABSTRACT

There is provided an image acquisition device including a light source configured to emit laser light and to be capable of controlling a wavelength of the laser light, a measurement unit configured to scan a sample using the laser light and to measure an intensity of measurement target light from the sample by receiving the laser light, and a control unit configured to generate an image of the sample based on intensity distribution of the measured measurement target light. The control unit controls a wavelength of the laser light based on the intensity distribution of the measured measurement target light.

18 Claims, 44 Drawing Sheets

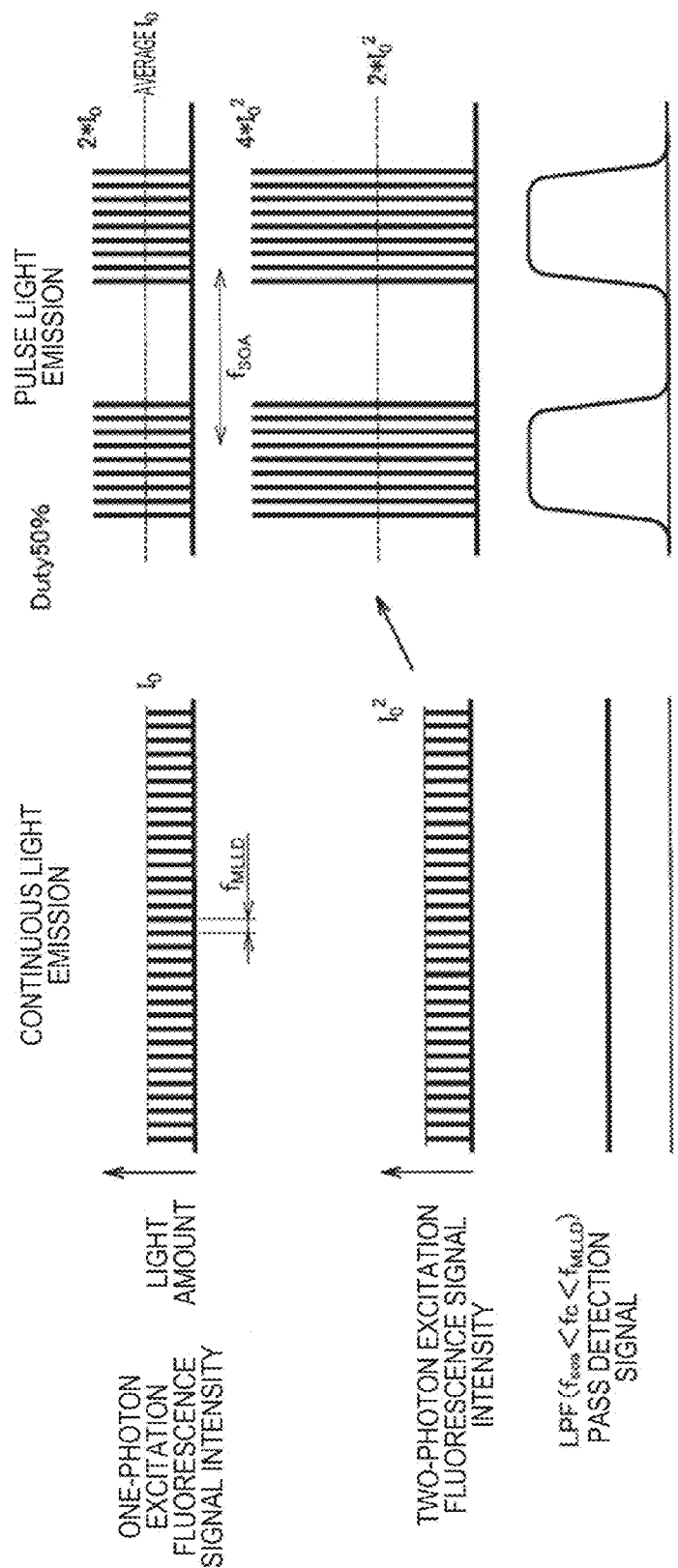

IMAGE ACQUISITION DEVICE AND IMAGE ACQUISITION METHOD

CROSS REFERENCE TO RELATED APPLICATIONS

This application claims the benefit of Japanese Priority Patent Application JP 2013-255066 filed Dec. 10, 2013, the entire contents of which are incorporated herein by reference.

BACKGROUND

The present disclosure relates to an image acquisition device and an image acquisition method.

In the field of biology, biotechnology, and the like, various kinds of microscopes are used to observe physiological responses and forms of living cells. Among the various kinds of microscopes, for example, there is a microscope through which a target is observed as a fluorescent or phosphorescent phenomenon occurring in a biological or non-biological measurement sample (which may be referred to hereinafter as a "sample"). For example, JP 2012-8261A discloses an example of a fluorescence microscope.

In addition, recently, a laser used as a light source has been made to have a short wavelength, and a two-photon (multi-photon) excitation microscope which uses a two-photon absorption process in material excitation has also come to be used as such a fluorescence microscope.

Such a fluorescence microscope scans a sample using excitation light output from, for example, a laser light source, then creates distribution of intensity of fluorescence from the sample, and thereby generates an image of the sample based on the distribution of the intensity.

SUMMARY

An image acquisition device that uses the same light source as the fluorescence microscope as described above mostly uses a laser light source with a fixed wavelength which can emit light with an excitation wavelength decided in advance depending on, for example, a fluorochrome to be used.

However, there are cases in which a fluorescence base substance in a sample fades with elapse of time, and in such a case, an excitation wavelength changes, and thus it is necessary to change the wavelength of excitation light output from a laser light source. When such a situation is dealt with by employing a configuration of using a laser light source with a fixed wavelength, it is necessary to provide a plurality of kinds of laser light sources, which results in an increase in a size of a device, which seriously hinders user convenience, and a price of the device tends to increase.

In addition, the excitation wavelength of the fluorescence base substance in the sample changes according to a degree of fading, and thus, in a configuration in which a plurality of laser light sources with fixed wavelengths are provided, there are cases in which an operator has to specify a laser light source which excites the fluorescence base substance by appropriately switching laser light sources in use, which results in deterioration of convenience. In addition, in the configuration in which a plurality of kinds of laser light sources are switched to be used, even if fluorescence from a sample in which fading has progressed can be excited, an image with high contrast is not necessarily obtained.

Therefore, the present disclosure proposes a novel and improved image acquisition device and image acquisition method which enable an image with a high contrast to be obtained using an easier method even in a situation in which an excitation wavelength of a sample changes.

According to an embodiment of the present disclosure, there is provided an image acquisition device including a light source configured to emit laser light and to be capable of controlling a wavelength of the laser light, a measurement unit configured to scan a sample using the laser light and to measure an intensity of measurement target light from the sample by receiving the laser light, and a control unit configured to generate an image of the sample based on intensity distribution of the measured measurement target light. The control unit controls a wavelength of the laser light based on the intensity distribution of the measured measurement target light.

According to another embodiment of the present disclosure, there is provided an image acquisition method including scanning a sample using laser light emitted from a light source configured to be capable of controlling a wavelength of the laser light and measuring an intensity of measurement target light generated from the sample by receiving the laser light, generating an image of the sample based on intensity distribution of the measured measurement target light, and controlling a wavelength of the laser light based on the intensity distribution of the measured measurement target light.

According to one or more embodiments of the present disclosure described above, an image acquisition device and an image acquisition method which enable an image with a high contrast to be obtained using an easier method even in a situation in which an excitation wavelength of a sample changes.

Note that the effect described above is not necessarily limiting, and along with or instead of the effect, any effect that is desired to be introduced in the present specification or other effects that can be expected from the present specification may be exhibited.

BRIEF DESCRIPTION OF THE DRAWINGS

FIG. 13B is a characteristic diagram showing a state in which peak power of a laser has been raised through intermittent light emission;

DETAILED DESCRIPTION OF THE EMBODIMENT(S)

Figure 1:
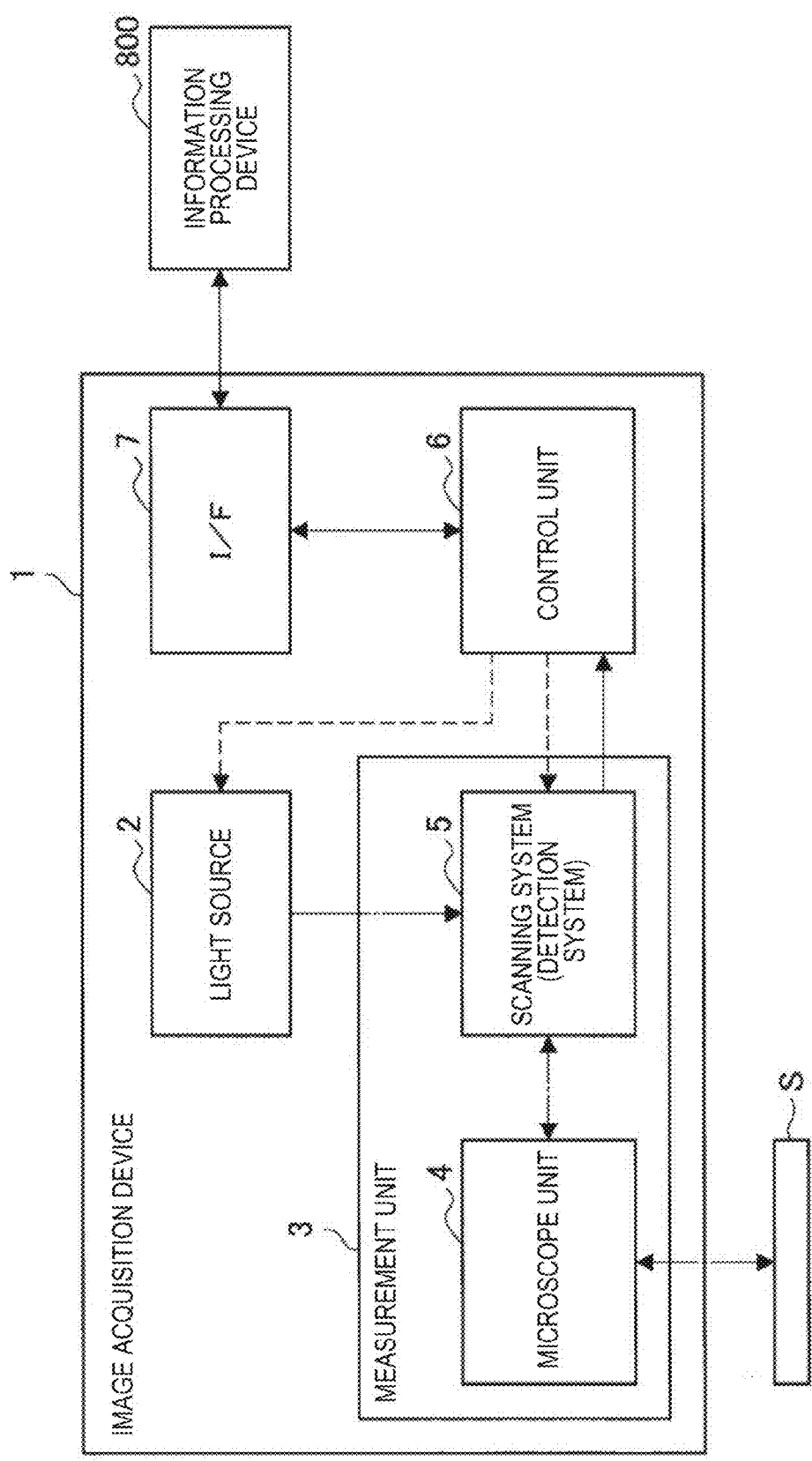
FIG. 1 is an illustrative diagram showing an example of a schematic configuration of an image acquisition device according to a first embodiment of the present disclosure.

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that description will be provided in the following order.
1. First Embodiment
  1.1. Overview of an image acquisition device
  1.2. Regarding a microscope
    1.2.1. Regarding a type of microscope: confocal microscope
    1.2.2. Regarding a type of microscope: two-photon excitation microscope
    1.2.3. Regarding a scanning method of a microscope
  1.3. Image acquisition device according to a comparative example
    1.3.1. Configuration of an optical system
    1.3.2. Configuration of a microscope unit
    1.3.3. Functional configuration of an image acquisition device
  1.4. Problem of the image acquisition device according to the comparative example
  1.5. Configuration of an image acquisition device
    1.5.1. Overview
    1.5.2. Configuration of a light source
    1.5.3. Configuration of an optical system
    1.5.4. Functional configuration of an image acquisition device
  1.6. File format of a raw file
  1.7. Details of a correction process
    1.7.1. Principle of correction
    1.7.2. Flow of an operation relating to correction 1.8. Details of intensity control of laser light
  1.8.1. Principle of intensity control
  1.8.2. Flow of an operation relating to intensity control
  1.9. Intensity control of laser light at a warm-up time
  1.10. Operation of an information processing device
  1.11. Conclusion
2. Second Embodiment
  2.1. Overview of an image acquisition device
  2.2. Configuration of the image acquisition device
    2.2.1. Configuration of an optical system
    2.2.2. Functional configuration of the image acquisition device
  2.3. File format of a raw file
  2.4. Flow of operations of the image acquisition device
  2.5. Details of wavelength control
    2.5.1. Principle of wavelength control: a case in which a sample is observed using a plurality of observation wavelengths
    2.5.2. An aspect of wavelength control: a case in which a sample is observed using a single observation wavelength
  2.6. Conclusion
3. Third Embodiment
  3.1. Overview of an image acquisition device
  3.2. Configuration of the image acquisition device
    3.2.1. Configuration of an optical system
    3.2.2. Functional configuration of the image acquisition device
  3.3. Conclusion
4. Fourth Embodiment
  4.1. Overview of an image acquisition device
  4.2. Configuration of the image acquisition device
  4.3. File format of a raw file
  4.4. Conclusion
5. Hardware configuration
6. Conclusion

1. First Embodiment

1.1. Overview of an Image Acquisition Device

First, an overview of an image acquisition device according to a first embodiment of the present disclosure will be described with reference to FIG. 1. FIG. 1 is an illustrative diagram showing an example of a schematic configuration of the image acquisition device according to the first embodiment of the present disclosure.

As shown in FIG. 1, the image acquisition device 1 according to the present embodiment includes a light source 2, a measurement unit 3, a control unit 6, and an interface (I/F) 7. The image acquisition device 1 according to the present embodiment scans a sample S using light emitted from the light source 2, measures fluorescence discharged from the sample S using the measurement unit 3, and thereby acquires an image of the sample S based on the measured fluorescence. Note that light obtained from the sample S, such as the fluorescence in this case, is equivalent to an example of "measurement target light."

Particularly, with regard to the image acquisition device 1 according to the present embodiment, at least the light source 2 and the measurement unit 3 are provided within the image acquisition device 1 (in other words, within the same housing). In the example shown in FIG. 1, for example, the light source 2, the measurement unit 3, the control unit 6, and the I/F 7 are provided within the image acquisition device 1.

The measurement unit 3 includes a microscope unit 4 which serves as a microscope to be described later, and a scanning system (detection system) 5 which handles scanning of the sample S and detection of fluorescence discharged from the sample S.

In addition, the control unit 6 controls operations of the light source 2 and the measurement unit 3, and converts light measured (detected) by the measurement unit 3 into an image. In addition, the control unit 6 controls the operation of the light source 2 based on the light measured (detected) by the measurement unit 3, thereby causing the light source 2 to operate stably.

The I/F 7 is an interface which enables the image acquisition device 1 to transmit and receive information to and from a user or another device. The image acquisition device 1 may be connected to, for example, an external network via the I/F 7 (for example, a communication interface), and output an image generated by the control unit 6 to an information processing device 800 connected via the external network.

Details of the light source 2, the measurement unit 3, the control unit 6, and the I/F 7 of the image acquisition device 1 according to the present embodiment will be separately described later in "1.5. Configuration of an image acquisition device."

Note that, as long as at least the light source 2 and the measurement unit 3 of the image acquisition device 1 according to the present embodiment are provided within the same housing, other constituent elements (for example, the control unit 6 and the I/F 7) may not necessarily be provided within the image acquisition device 1. For example, an information processing device which can transmit and receive information to and from the image acquisition device 1 which includes the light source 2 and the measurement unit 3 may be separately provided, and the control unit 6 and the I/F 7 may be provided in the information processing device. It is of course needless to say that the control unit 6 and the I/F 7 may be provided on the information processing device 800 side.

1.2. Regarding a Microscope

Prior to describing details of the image acquisition device 1 according to the present embodiment, a microscope which is used as the microscope unit 4 of the measurement unit 3 of the image acquisition device 1 according to the present embodiment will be described herein with reference to FIGS. 2 to 8.

Figure 2:
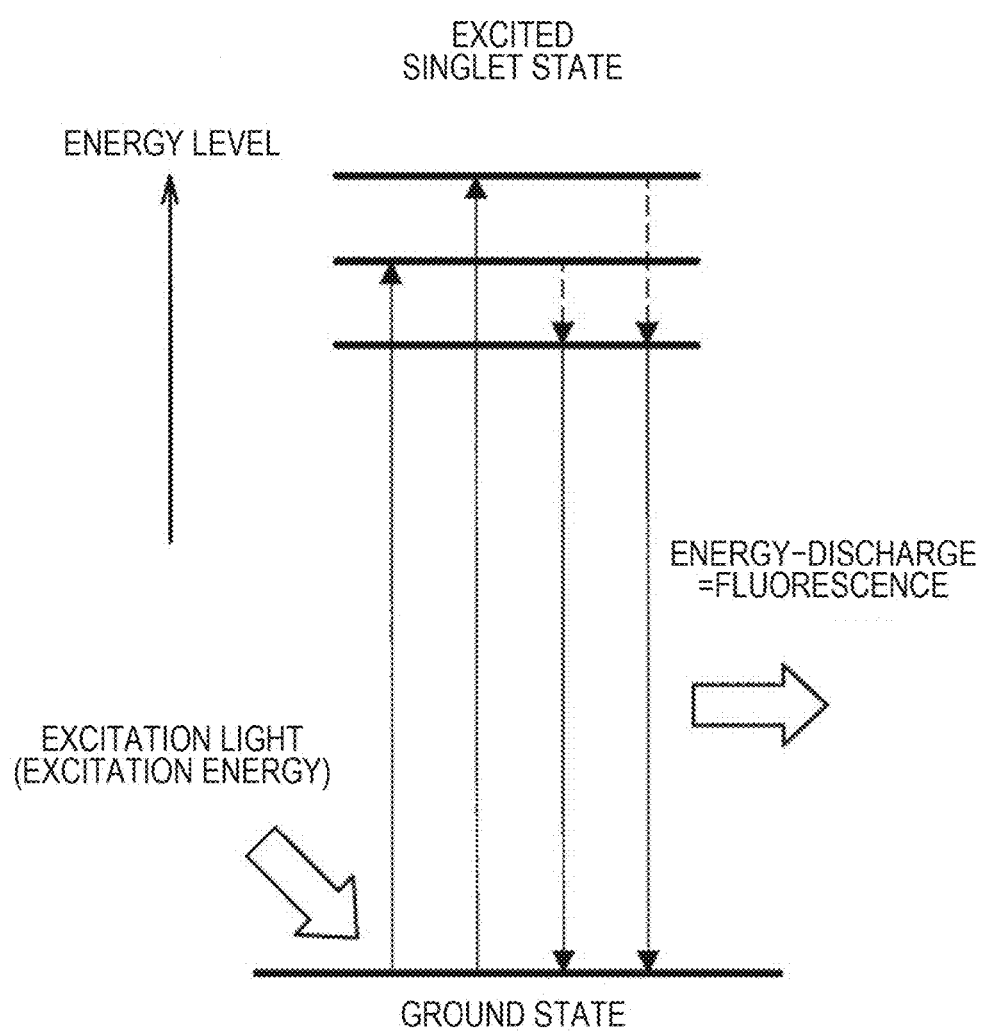
FIG. 2 is an illustrative diagram for describing fluorescence.

As one of phenomena occurring in the sample S on which the present embodiment focuses, fluorescence discharged from the sample S can be exemplified. First, fluorescence will be briefly described below with reference to FIG. 2. FIG. 2 is an illustrative diagram for describing fluorescence.

When light having a predetermined wavelength is radiated to a molecule which constitutes a measurement sample (or adheres to a measurement sample), there are cases in which electrons in the molecule move from an energy level corresponding to a ground state to an energy level corresponding to an excited state using energy of the radiated light. The light radiated at that time is called excitation light. When a molecule which is in the ground state is excited and thus an excited singlet state occurs, excited electrons are supposed to move to any energy level corresponding to the excited singlet state, however, the excited electrons move to a lower energy level while discharging energy through internal conversion. Energy is sometimes discharged as light when electrons in an excited state return to the ground state, and the light discharged at that time is fluorescence, which is the focus of the present embodiment.

<<1.2.1. Regarding a Type of Microscope: Confocal Microscope>>

Figure 3:
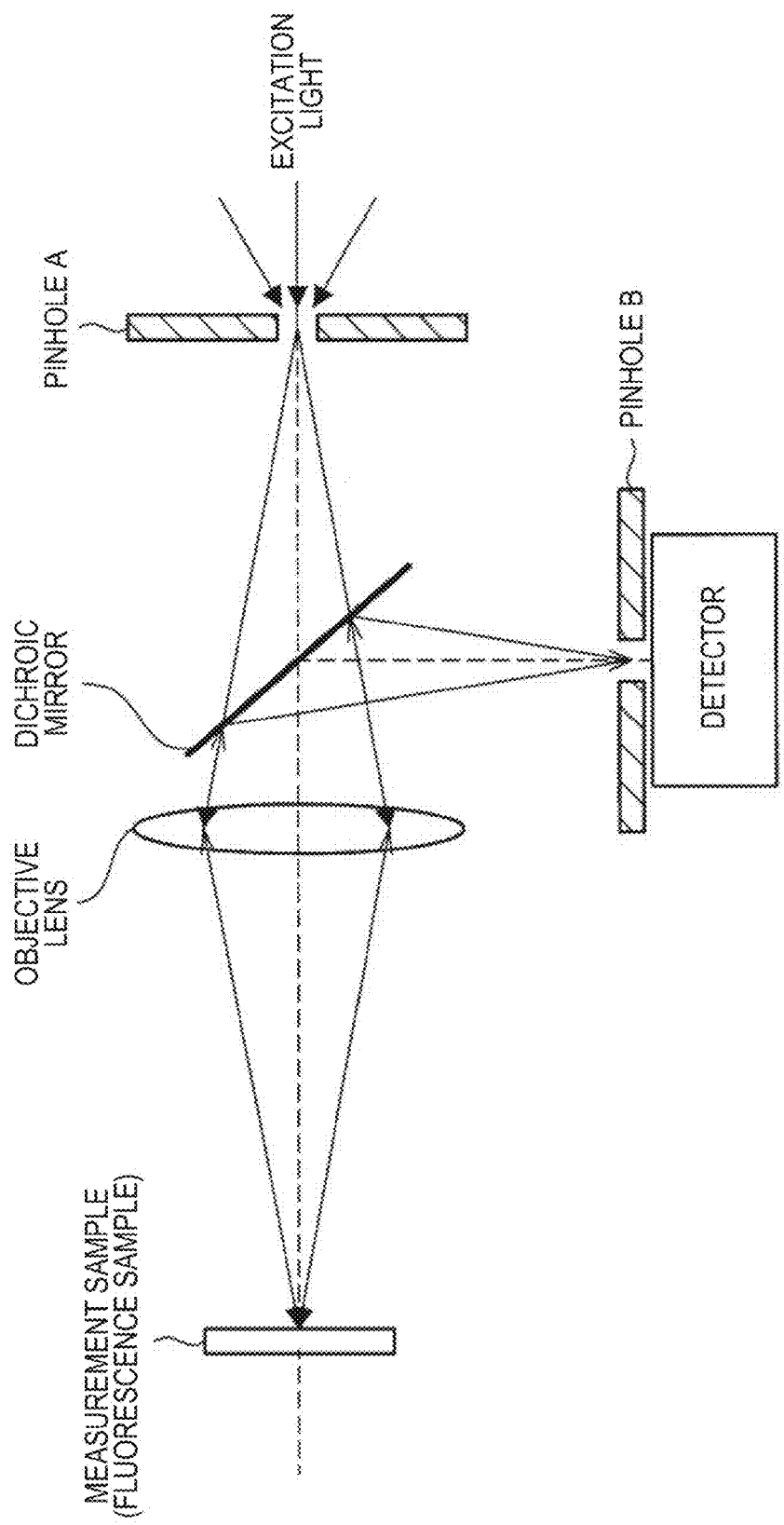
FIG. 3 is an illustrative diagram for describing the principle of a confocal microscope.
Figure 4:
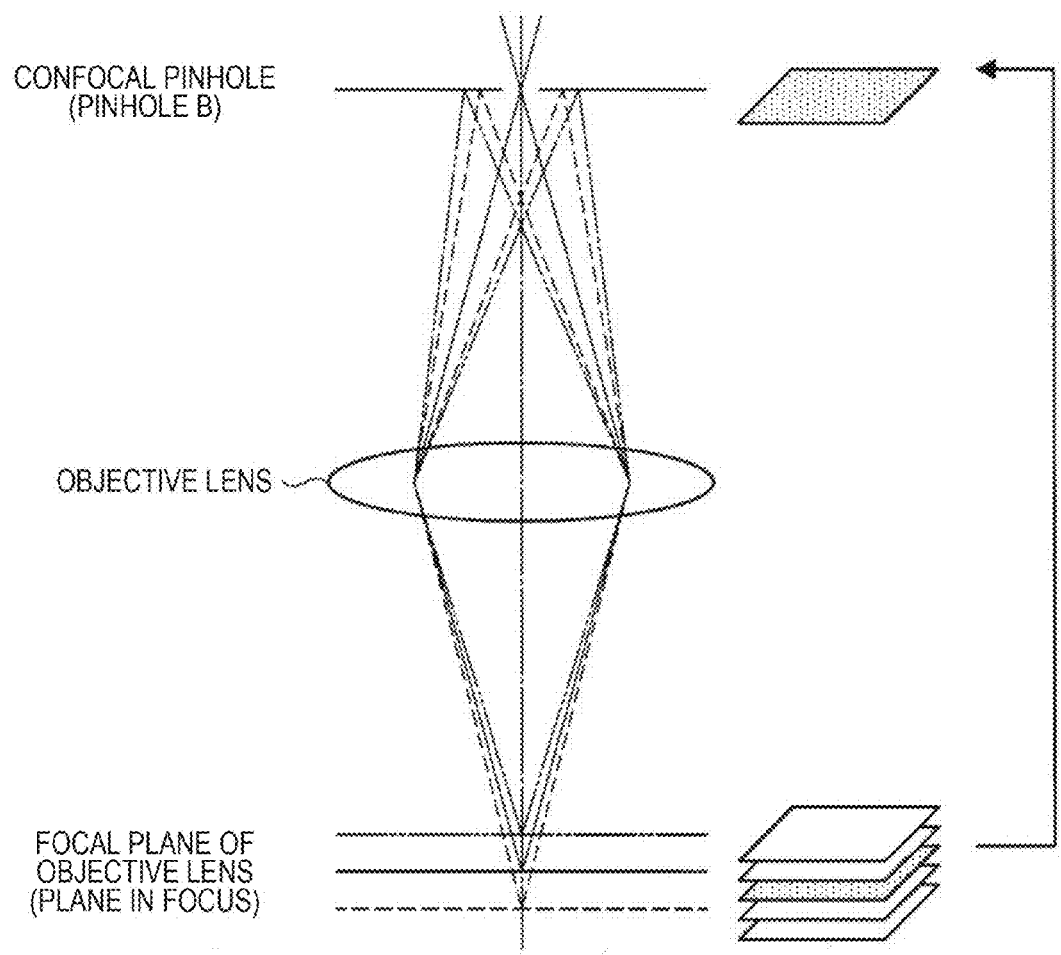
FIG. 4 is an illustrative diagram for describing the principle of the confocal microscope.

As an optical microscope which is used to observe fluorescence as above, there is a confocal microscope as shown in FIGS. 3 and 4. Hereinbelow, the principle of a confocal microscope will be briefly described with reference to FIGS. 3 and 4. FIGS. 3 and 4 are illustrative diagrams for describing the principle of a confocal microscope.

The confocal microscope shown in FIG. 3 is configured to use a laser beam as excitation light and guide the laser beam to a measurement sample (fluorescence sample), and to guide fluorescence generated on a focal plane of the measurement sample to a detector. The laser beam used herein as excitation light can be regarded as a point light source as the laser beam passes through a pinhole A, and the laser beam goes through a dichroic mirror and an objective lens, and then is projected on the fluorescence sample. In the fluorescence sample, fluorescence is generated by energy of the projected laser beam, and the emitted fluorescence is collected by the objective lens, and then guided in the direction of the detector by the dichroic mirror. Another pinhole B is installed in front of the detector, and the fluorescence that has passed through the pinhole B is detected by the detector such as a photomultiplier tube (PMT).

Here, a wavelength of the laser beam used as excitation light can be appropriately selected according to, for example, a type or the like of a fluorescent pigment used to die the measurement sample, and is not limited to a specific wavelength.

In the confocal fluorescence microscope as described above, the installation position of the pinhole A, the projection position of the point light source (the focal plane of the measurement sample), and the installation position of the pinhole B are in an optically conjugated relation, and the conjugated relation of the three points are said to be in a confocal relation.

At this time, the fluorescence emitted from a focal plane of the objective lens (a plane in focus) can be collected by the objective lens and pass through the confocal pinhole (the pinhole B of FIG. 3) as shown in FIG. 4, but it is not possible for fluorescence output from the portion which is out of focus to pass through the confocal pinhole. As a result, the confocal fluorescence microscope can obtain luminance information of only a portion of the measurement sample in focus. Thus, it is possible to construct a two-dimensional image (an optical cross-sectional image) of only the portion in focus by scanning a plane of the measurement sample (sample plane) in the longitudinal direction and the lateral direction. In addition, by repeating the scanning of the sample plane as described above while changing a focal position and cumulating fluorescence from the measurement sample which is in different depth positions (depth-wise positions), it is possible to obtain a set of optical cross-sectional images (a three-dimensional enlarged image group) at each depth position.

<<1.2.2. Regarding a Type of Microscope: Two-Photon Excitation Microscope>>

Figure 5:
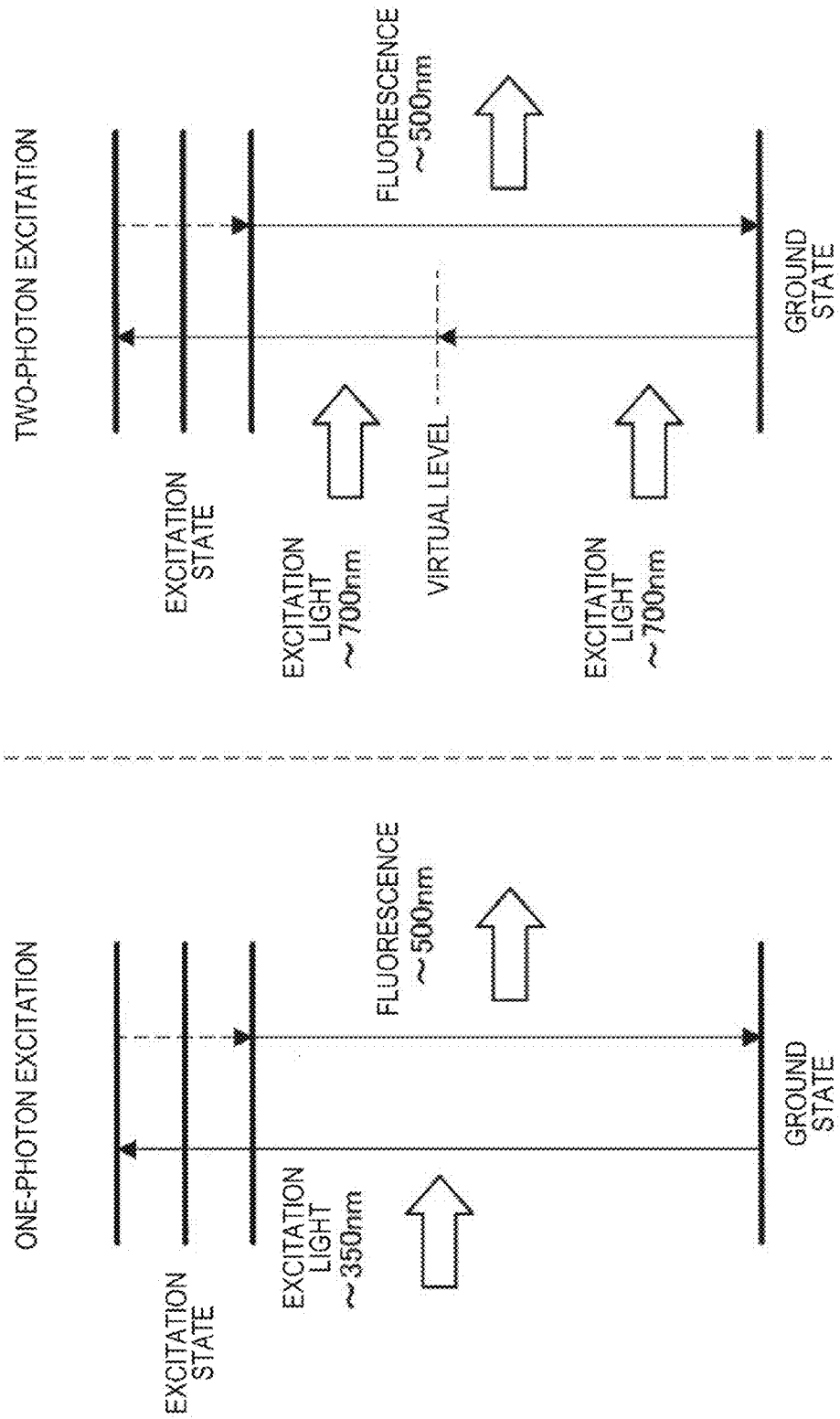
FIG. 5 is an illustrative diagram for describing the difference between fluorescence of one-photon excitation and fluorescence of two-photon excitation.

As another technology with which a three-dimensional image can be obtained, there is a two-photon excitation microscope. FIG. 5 is an illustrative diagram for describing the principle of two-photon excitation. The drawing on the left side of FIG. 5 is an illustrative diagram showing the principle of general fluorescence described above, in which, by causing molecules to be excited using excitation light having a certain wavelength (excitation light having a wavelength of 350 nm in the drawing), fluorescence having a wavelength longer than the excitation light (fluorescence having a wavelength of 500 nm) is output. Since the mechanism for generating fluorescence described above involves generating fluorescence when molecules are in an excited state due to, so to speak, an interaction between one photon and the molecules, it is called fluorescence generation through one-photon excitation.

On the other hand, there are cases in which, while molecules are excited by one photon to a virtual level, the molecules are further excited by one more photon, and when the molecules are thereby excited to be in an excited state and the molecules in the excited state transition to a ground state, fluorescence is generated as shown in the drawing on the right side of FIG. 5. Since the mechanism for generating fluorescence described above involves generating fluorescence by putting the molecules in the excited state through an interaction between the two photons and the molecules, it is called fluorescence generation through two-photon excitation. When the fluorescence generation through two-photon excitation is used, it is possible to generate fluorescence having a shorter wavelength than the excitation light (in the example of FIG. 5, fluorescence having a wavelength of 500 nm is generated using infrared light having a wavelength of 700 nm as excitation light).

In order to establish two-photon excitation, within an extremely short period of time of about $1.0 \times 10^{-16}$ seconds in which molecules that have collided with a first photon are excited to a virtual level, the molecules are required to collide with one more photon and then to transition to the excited singlet state, and thus a higher photon density is necessary and a laser light source that can output high peak power is used. In addition, since a discharged fluorescence signal is extremely weak in comparison with the process of one-photon excitation, an optical system which brings little loss and a detector having excellent sensitivity are required to be used.

Figure 6:
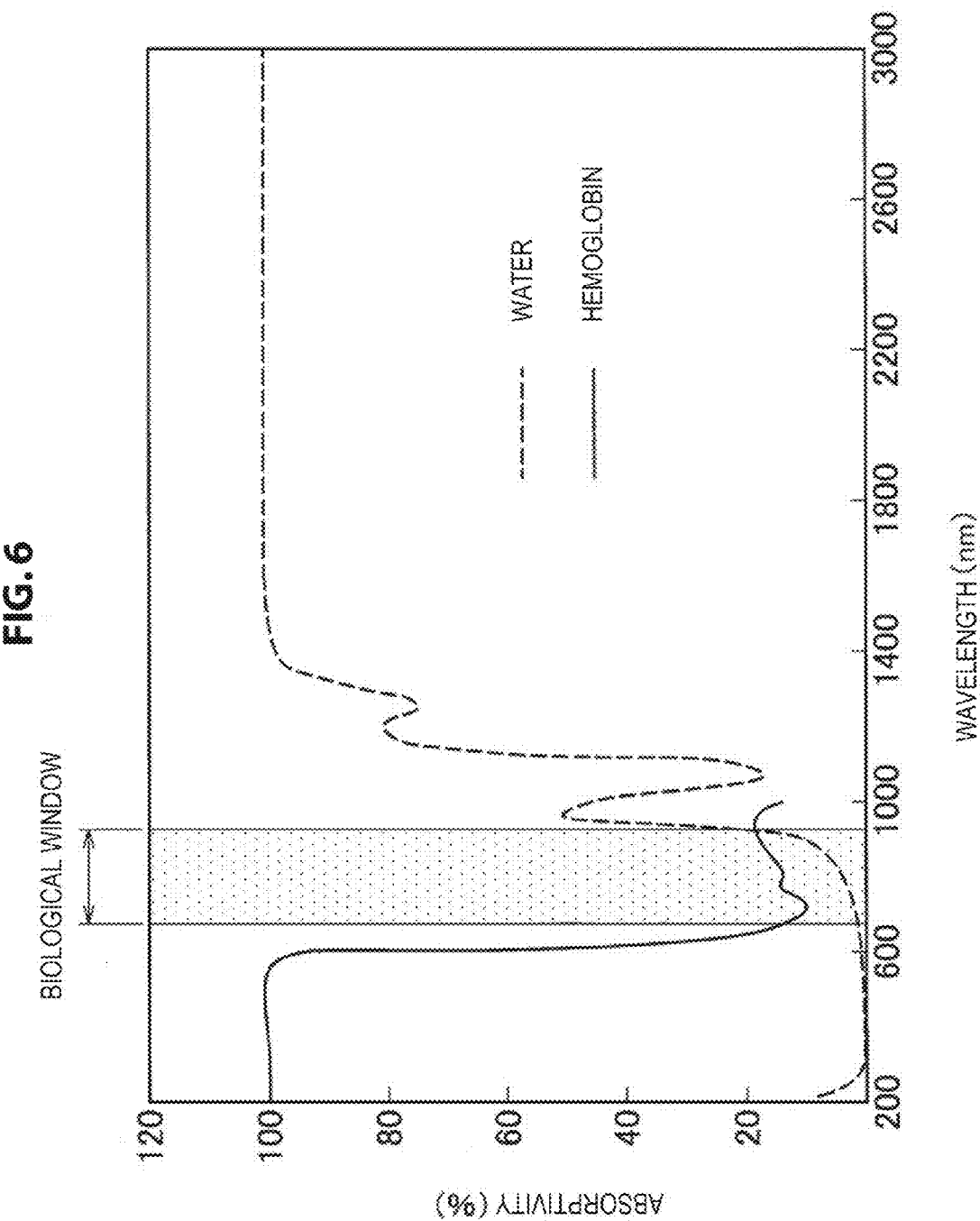
FIG. 6 is a graph for describing a light absorption characteristic of a biological tissue.

A major reason for which such a two-photon excitation fluorescence microscope is desired in spite of the problems is that a fluorescent wavelength in an infrared band of about 700 nm to 1000 nm that is used in two-photon excitation forms a wavelength band that is called a "biological window" through which fluorescence is transmitted by a biological tissue without being absorbed by water or hemoglobin as shown in FIG. 6. It is said that, while a confocal fluorescence microscope can perform observation of only a depth of about 100 μm, the two-photon excitation fluorescence microscope can perform observation up to a depth of 1000 μm (1 mm) due to a high transmission property of such excitation light.

Figure 7:
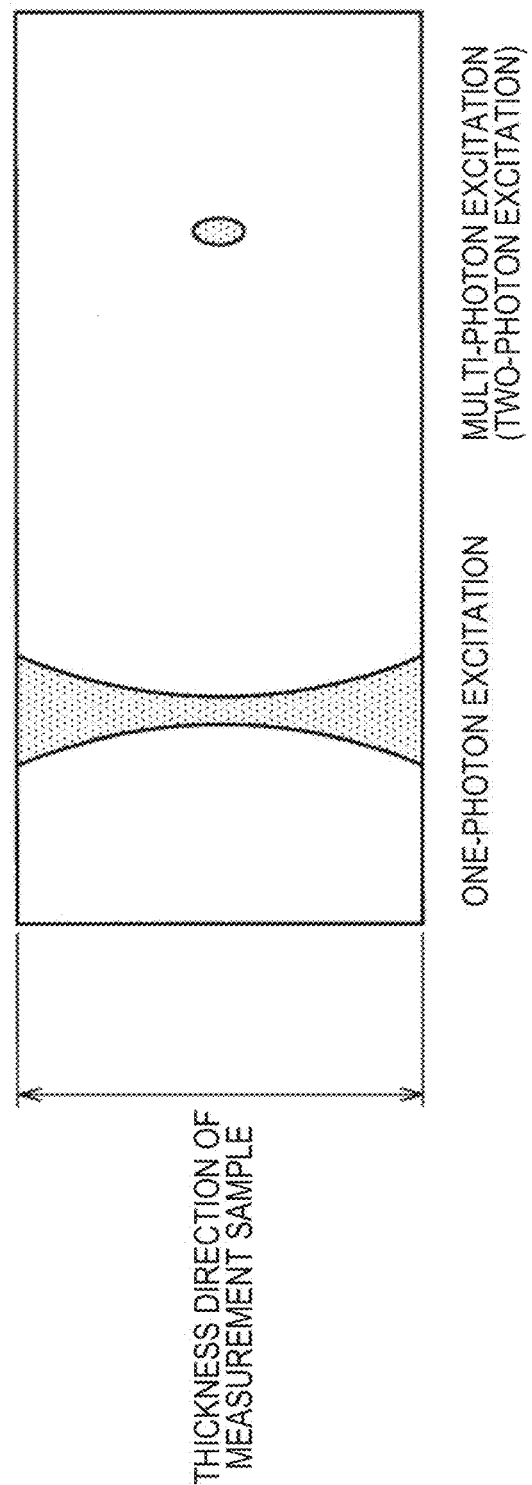
FIG. 7 is an illustrative diagram for describing a two-photon excitation fluorescence microscope.

In addition, as shown in FIG. 7, while molecules are excited over an entire thickness direction of a sample in addition to on a focal plane in one-photon excitation fluorescence microscope and fluorescence is emitted from the entire thickness direction, they are excited only in vicinity of a focal plane in two-photon excitation fluorescence microscope. For this reason, it is possible to observe a deeper portion of a sample brightly and to suppress damage caused by diminishment of fluorescence to the minimum even when scanning is repeatedly executed on different focal planes in the longitudinal direction and the lateral direction. In addition, since a phototoxic property can be suppressed to the minimum for the same reason, it is possible to observe a living cell located at a deep position of a sample for a long time.

In addition, since fluorescence emitted through excitation is derived from a microscopic area within a sample, the two-photon excitation fluorescence microscope can obtain fluorescence images if optical signals thereof are all detected. Accordingly, in the two-photon excitation fluorescence microscope, a detection optical system of the microscope can be simplified. In other words, since fluorescence is emitted only from a sample in the vicinity of a focal position in the process of two-photon excitation, it is not necessary to cut unnecessary signals using a pinhole as in a confocal fluorescence microscope, and it is better to dispose a detector in the vicinity of the sample and gather as many omnidirectionally dispersing fluorescence signals as possible.

<<1.2.3. Regarding a Scanning Method of a Microscope>>

Figure 8:
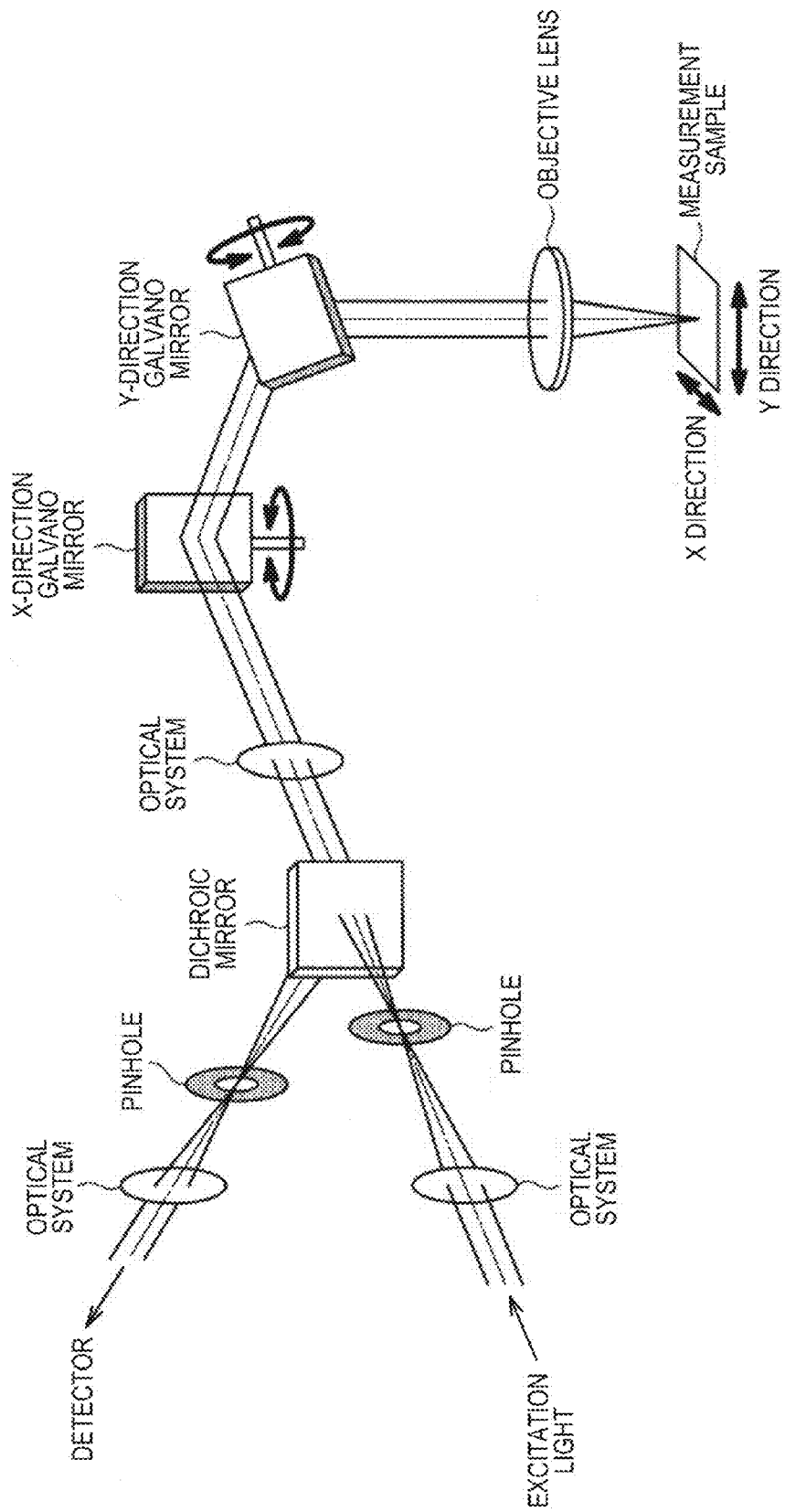
FIG. 8 is an illustrative diagram for describing a sample scanning method of a microscope.

Such a laser scanning microscope described above acquires two-dimensional images (optical cross-sectional images) by performing scanning of a measurement sample in an X direction and a Y direction (longitudinal direction and lateral direction) using two types of galvano mirrors in many cases. FIG. 8 shows a configuration example of a confocal fluorescence microscope that uses two types of galvano mirrors.

Excitation light emitted from a laser light source is transmitted through an optical system such as a lens and a pinhole provided at a conjugated position, and then transmitted by a dichroic mirror that transmits the excitation light and reflects fluorescence. The excitation light transmitted through the dichroic mirror is transmitted by another optical system such as a lens, and an X coordinate thereof is controlled by an X-direction galvano mirror that controls scanning of a measurement sample in the X direction, then a Y coordinate is controlled by a Y-direction galvano mirror that controls scanning thereof in the Y direction, and then the excitation light is collected at desired X-Y coordinates on the measurement sample by an objective lens.

Fluorescence emitted from the measurement sample is reflected by the Y-direction galvano mirror and the X-direction galvano mirror, takes the same route as the excitation light, and is then reflected by the dichroic mirror. The fluorescence reflected by the dichroic mirror is transmitted through a pinhole provided at a conjugated position, and then is guided to a detector such as a photomultiplier tube.

Here, each of the two galvano mirrors that are used to control the light collection position on the measurement sample has a rotation shaft connected thereto as schematically illustrated in FIG. 8. A rotation amount of the rotation shaft of each galvano mirror is controlled according to a magnitude of an input voltage, and thereby an angle that a mirror plane faces can be quickly and accurately changed.

1.3. Image Acquisition Device According to a Comparative Example

Figure 9:
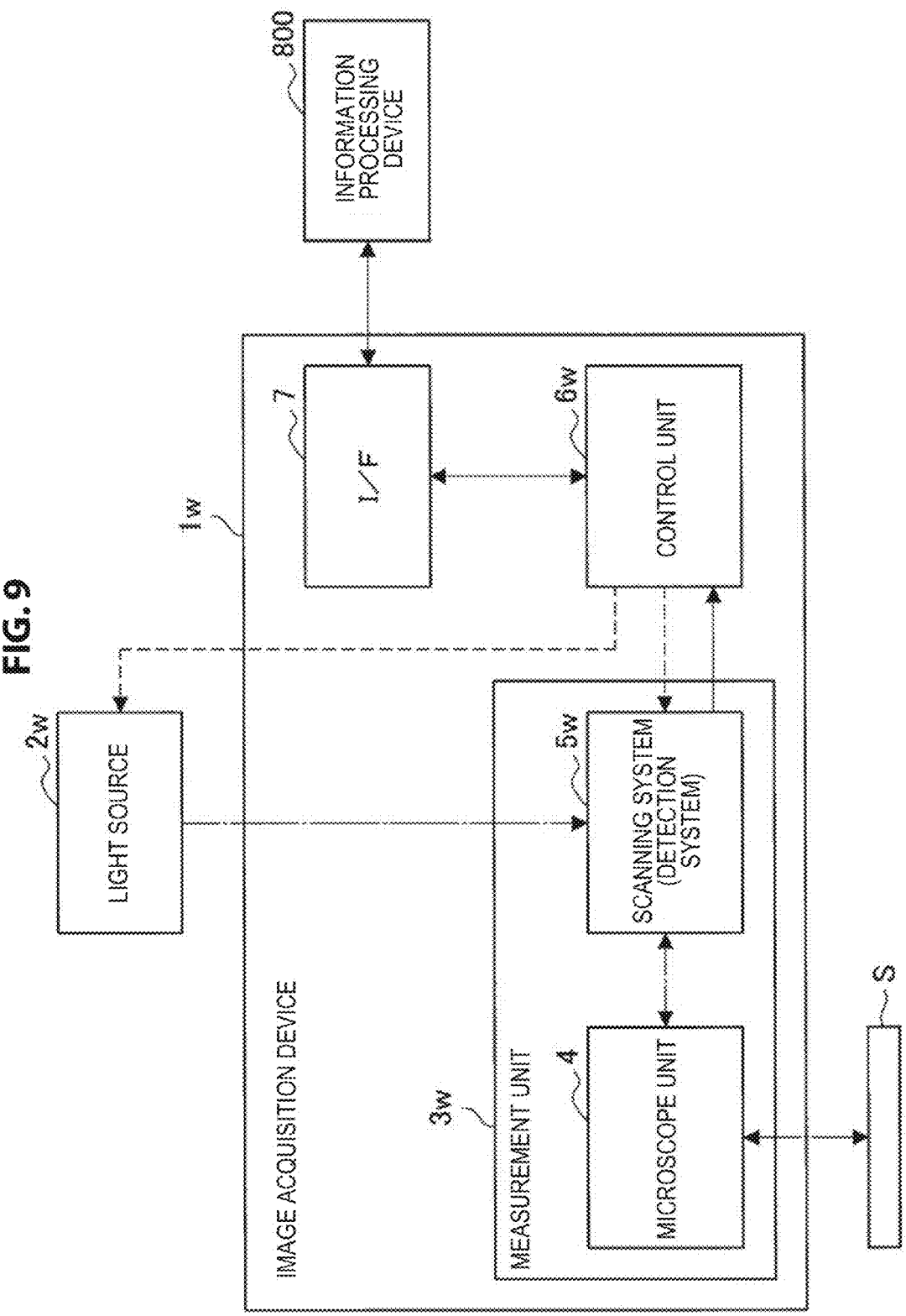
FIG. 9 is a system diagram showing an example of a schematic system configuration of an image acquisition device according to a comparative example.

Next, by describing a configuration of an image acquisition device of the related art as a comparative example while describing details of the image acquisition device 1 according to the present embodiment, a problem of the image acquisition device 1 according to the present embodiment will be clarified. For example, FIG. 9 is an illustrative diagram showing an example of a schematic configuration of an image acquisition device according to a comparative example. As the image acquisition device 1w according to the comparative example is shown in FIG. 9, a light source 2w is provided outside of the image acquisition device 1w.

<<1.3.1. Configuration of an Optical System>>

Herein, a configuration of the optical system of the image acquisition device 1w according to the comparative example will be described with reference to FIG. 10 focusing mainly on radiation of light from the light source 2w onto a sample S and detection of fluorescence generated from the sample S by being excited by the light.

Figure 10:
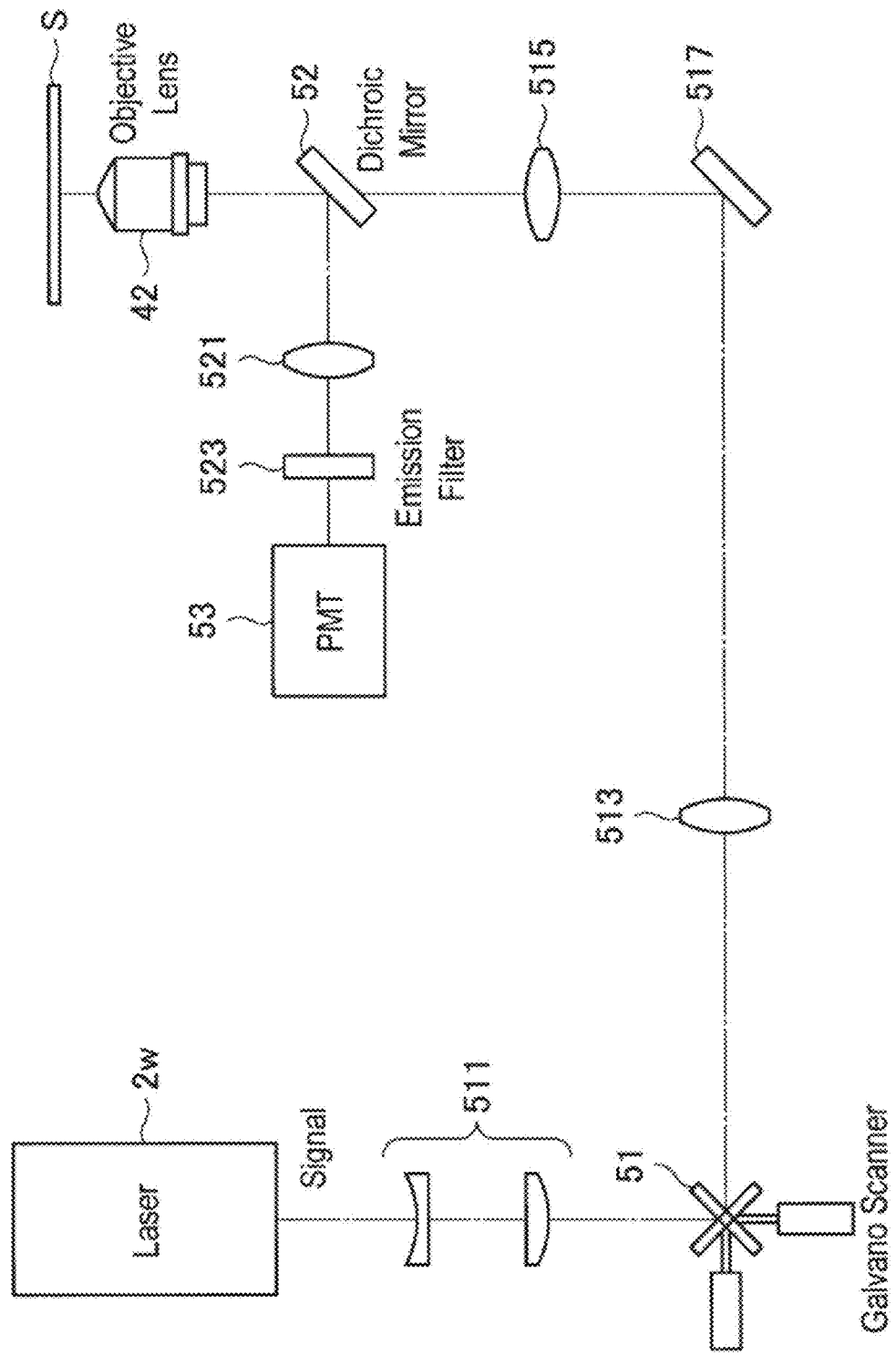
FIG. 10 is an illustrative diagram showing an example of a configuration of an optical system of the image acquisition device according to the comparative example.

As shown in FIG. 10, the optical system of the image acquisition device 1w according to the comparative example includes the light source 2w, a beam-forming lens 511, a galvano mirror 51, lenses 513 and 515, a mirror 517, a dichroic mirror 52, an objective lens 42, an image-forming lens 521, an emission filter 523, and a photodetector 53. Note that, in the example shown in FIG. 10, a PMT is used as the photodetector 53. Hereinafter, it is assumed that the PMT is used as the photodetector 53 and description of "PMT 53" means the "photodetector 53."

Excitation light (laser light) emitted from the light source 2w has a beam diameter enlarged by the beam-forming lens 511 as it is parallel light and then reaches the galvano mirror 51. The excitation light that has reached the galvano mirror 51 is reflected by the galvano mirror 51, and then guided to the dichroic mirror 52 through the lens 513, the mirror 517, and the lens 515. The lens 513, the mirror 517, and the lens 515 are an optical system for guiding the excitation light reflected by the galvano mirror 51 to the dichroic mirror 52.

The excitation light that has reached the dichroic mirror 52 is transmitted therethrough and then guided to the objective lens 42. The objective lens 42 collects the excitation light onto the sample S. Then, the objective lens 42 and the image-forming lens 521 enlarge an image of the sample S to a predetermined magnification, and the enlarged image is formed on a detection plane of the PMT 53.

When the excitation light is radiated to the sample S, some molecules of the sample S are excited by the excitation light and thereby emit fluorescence. The fluorescence is reflected by the dichroic mirror 52 via the objective lens 42, reaches the image-forming lens 521, collected by the image-forming lens 521, and then forms an image on the detection plane of the PMT 53 via the emission filter 523. The emission filter 523 transmits only colored light therethrough by, for example, absorbing light (natural light) other than the colored light enlarged by the objective lens 42. An image of the colored light that has lost the natural light is formed on the PMT 53.

<<1.3.2. Configuration of a Microscope Unit>>

Figure 11:
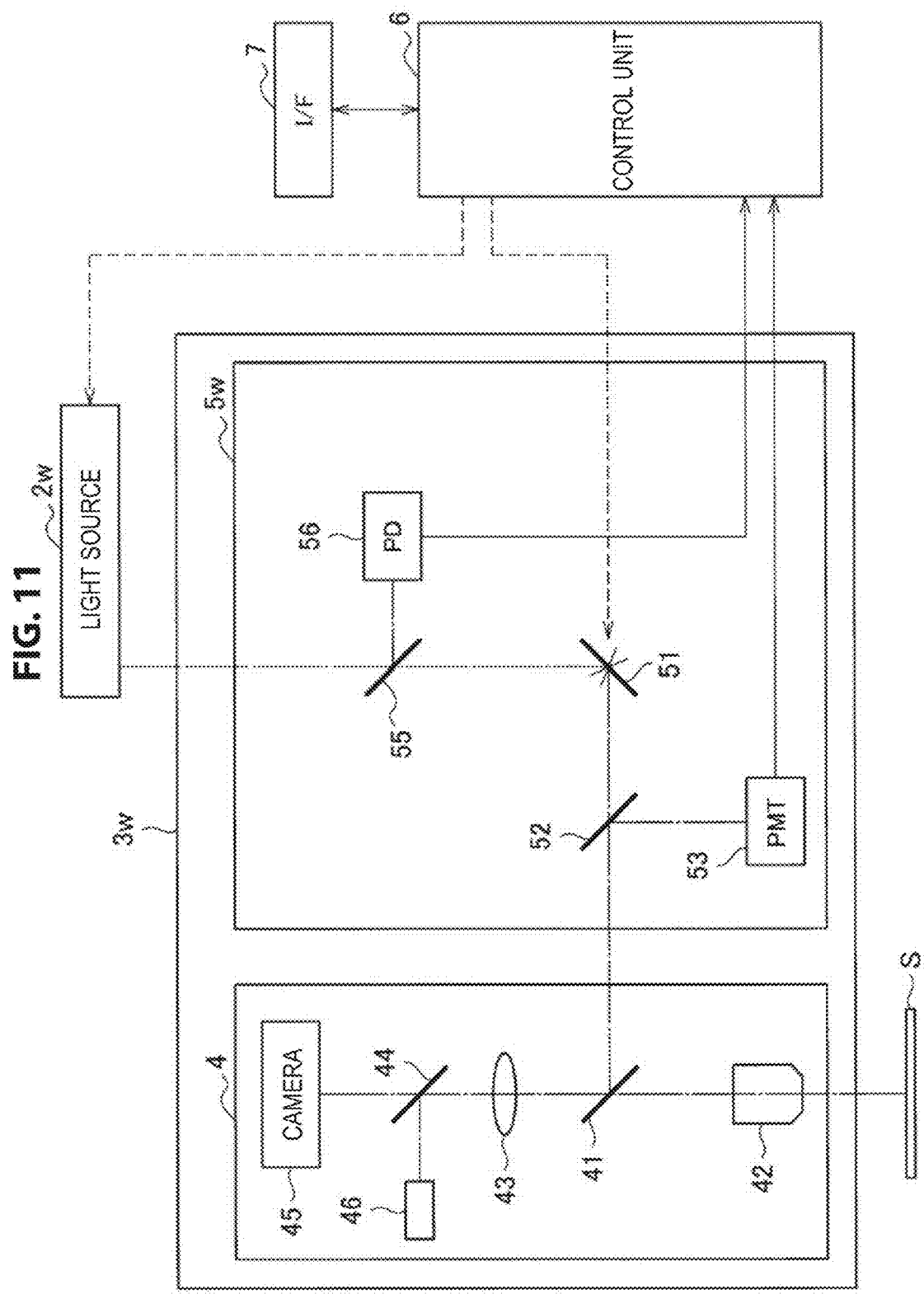
FIG. 11 is an illustrative diagram for describing an example of a configuration of a microscope unit.

Next, an example of a configuration of the microscope unit 4 will be described with reference to FIG. 11. FIG. 11 is an illustrative diagram for describing the example of the configuration of the microscope unit 4. As shown in FIG. 11, the microscope unit 4 includes non-polarized beam splitters 41 and 44, an objective lens 42, a filter 43, a camera 45, and an eyepiece 46. Note that, in the example shown in FIG. 11, each constituent element of a scanning system (detection system) 5w corresponds to that to which the same reference numeral is given in the optical system shown in FIG. 10. In addition, in the example shown in FIG. 11, a part of the configuration shown in FIG. 10 is omitted.

Excitation light (laser light) emitted from the light source 2w is guided to the non-polarized beam splitter 41 disposed in the microscope unit 4 via the scanning system (detection system) 5w. The non-polarized beam splitter 41 reflects the excitation light guided via the scanning system (detection system) 5w toward the objective lens 42. The objective lens 42 is equivalent to the objective lens 42 in the optical system shown in FIG. 10.

The objective lens 42 collects the excitation light on the sample S. Accordingly, some molecules of the sample S are excited by the excitation light and emit fluorescence. The fluorescence generated from the sample S is guided to the non-polarized beam splitter 41 via the objective lens 42. The non-polarized beam splitter 41 bifurcates the fluorescence guided via the objective lens 42 in both directions of the scanning system (detection system) 5w and the filter 43.

The filter 43 selectively transmits colored light that has been guided via the objective lens 42 and the non-polarized beam splitter 41 therethrough. As a specific example, an emission filter can be applied as the filter 43. In this case, the filter 43 absorbs light (natural light) other than the colored light, and transmits only the colored light therethrough. An image of the colored light that has lost the natural light is guided to the non-polarized beam splitter 44. The non-polarized beam splitter 44 bifurcates the image of the colored light that has been guided via the filter 43 in both directions of the camera 45 and the eyepiece 46. With this configuration, a user can observe an image of the sample guided via the eyepiece 46 or photograph the image of the sample using the camera 45.

In addition, the fluorescence guided toward the scanning system (detection system) 5w is reflected by the dichroic mirror 52 and guided to the PMT 53, thereby being detected by the PMT 53. Note that a process based on fluorescence detected by the PMT 53 will be described later as an operation of a control unit 6w.

<<1.3.3. Functional Configuration of an Image Acquisition Device>>

Next, a functional configuration of the image acquisition device 1w according to the comparative example will be described with reference to FIG. 12 particularly focusing on configurations of the control unit 6w and an I/F 7.

Figure 12:
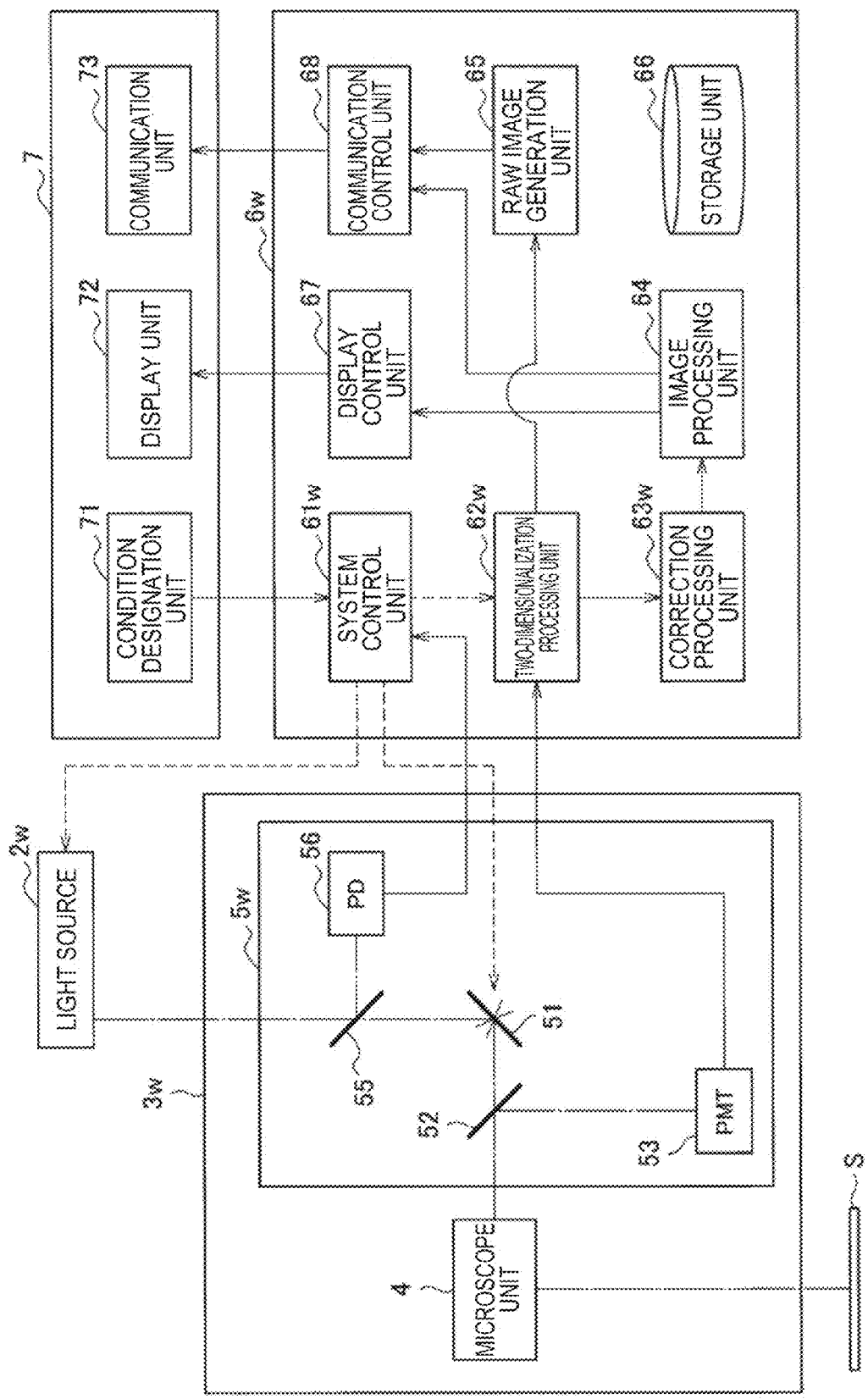
FIG. 12 is an illustrative diagram for describing an example of a functional configuration of the image acquisition device according to the comparative example.

As shown in FIG. 12, the image acquisition device 1w according to the comparative example is connected to the light source 2w outside of the device and causes excitation light emitted from the light source 2w to be radiated to the sample S via the scanning system (detection system) 5w and the microscope unit 4. At this time, the sample S is scanned by the excitation light as a system control unit 61w to be described later controls an operation of the galvano mirror 51.

Then, fluorescence generated from the sample S by the radiated excitation light is guided to the scanning system (detection system) 5w via the microscope unit 4, and then detected by the PMT 53 of the scanning system (detection system) 5w. The PMT 53 converts the detected fluorescence into an electric signal through photoelectric conversion at a sampling rate set in advance, and outputs the signal to the control unit 6w as data indicating an intensity of the fluorescence.

The control unit 6w includes the system control unit 61w, a two-dimensionalization processing unit 62w, a correction processing unit 63w, an image processing unit 64, a raw image generation unit 65, a storage unit 66, a display control unit 67, and a communication control unit 68. In addition, the I/F 7 includes a condition designation unit 71, a display unit 72, and a communication unit 73.

The system control unit 61w controls operations of the light source 2w and the galvano mirror 51 based on a measurement condition designated by a user via the condition designation unit 71. The condition designation unit 71 is an input I/F with which the user designates a condition for measurement and image acquisition (which may be collectively referred to hereinafter as a "measurement condition"). For example, the user can designate scanning conditions for output of the light source 2w and scanning of the sample S (for example, a range to be scanned or resolution of a generated image) as a measurement condition through the condition designation unit 71.

The system control unit 61w controls operations of the galvano mirror 51 based on the scanning condition designated by the user as the measurement condition, and then outputs control information indicating details of the control to the two-dimensionalization processing unit 62w to be described later.

The two-dimensionalization processing unit 62w sequentially acquires data indicating intensities of the fluorescence detected (measured) by the PMT 53 from the PMT 53 at a sampling rate set in advance. In addition, the two-dimensionalization processing unit 62w sequentially acquires the control information indicating the details of the control of the galvano mirror 51 from the system control unit 61w. Accordingly, the two-dimensionalization processing unit 62w can ascertain data at what position on the sample S the data indicating the intensities of the fluorescence acquired from the PMT 53 corresponds to based on the control information acquired from the system control unit 61w. In other words, the two-dimensionalization processing unit 62w performs two-dimensionalization on the data indicating the intensities of the fluorescence that have been sequentially acquired from the PMT 53 in series based on the control information acquired from the system control unit 61w, and thereby generates intensity distribution of the detected fluorescence.

The intensity distribution of the fluorescence generated by the two-dimensionalization processing unit 62w undergoes a correction process of, for example, removal of noise or the like by the correction processing unit 63w and then is output to the image processing unit 64. The image processing unit 64 generates image data by performing image processing such as a compression process on the correction-processed intensity distribution.

The image processing unit 64 outputs the generated image data to, for example, the display control unit 67. In addition, the image processing unit 64 may output the generated image data to the communication control unit 68. In addition, the image processing unit 64 may cause the generated image data to be stored in the storage unit 66.

The raw image generation unit 65 acquires the intensity distribution of the fluorescence from the two-dimensionalization processing unit 62w, and forms the intensity distribution of the fluorescence in a predetermined file format as image data (raw image) to generate a raw file. At this time, the raw image generation unit 65 may acquire information relating to the intensity distribution of the fluorescence such as an acquisition condition for the intensity distribution of the fluorescence (for example, a photographing condition such as a parameter at the time of photographing or a scanning condition) from the system control unit 61w and associate the acquired information as relevant information with the generated raw file. Note that the relevant information may be recorded in the raw file as accessory information of the raw file, or may be associated with the raw file as a separate file. Note that, hereinbelow, there are cases in which such aspects are collectively described simply as "associated."

The raw image generation unit 65 outputs the generated raw file to, for example, the communication control unit 68. In addition, the raw image generation unit 65 may cause the generated raw file to be stored in the storage unit 66.

The storage unit 66 is a storage unit for storing various kinds of control data used within the image acquisition device 1w and data generated within the image acquisition device 1w (for example, the image data or the raw file) therein. The storage unit 66 may be configured as, for example, a database. In addition, the storage unit 66 may be used as a storage area for storing data created temporarily to execute various kinds of processing, for example, image processing.

The display control unit 67 acquires the image data from the image processing unit 64 and causes the acquired image data to be displayed on the display unit 72. The display unit 72 is an output I/F, for example, a display for displaying information thereon. Thereby, the user can check the image of the sample S through the display unit 72.

In addition, the display control unit 67 may cause a user interface (U/I) for manipulating the image acquisition device 1w to be displayed on the display unit 72. Note that control data of the display control unit 67 for generating the U/I may be stored in, for example, the storage unit 66 in advance.

The communication control unit 68 controls operations of the communication unit 73 that performs communication with an external device such as the information processing device 800 so that the image acquisition device 1w transmits and receives data to and from the external device via a network. The communication control unit 68 acquires, for example, the image data or the raw file generated within the image acquisition device 1w and transmits the acquired data to the information processing device 800 via the network by controlling the communication unit 73. Accordingly, it is possible to process, for example, the generated image data or the raw file in the information processing device 800 that has a higher image processing capability than the image acquisition device 1w.

1.4. Problem of the Image Acquisition Device According to the Comparative Example With regard to the image acquisition device 1w according to the comparative example, the light source 2w is provided outside of (in other words, externally attached to) the image acquisition device 1w as described above, which tends to increase a size of a system that includes the light source 2w and the image acquisition device 1w. On the other hand, miniaturization of the image acquisition device 1 according to the present embodiment by mounting the light source 2 (in other words, a laser module) in the housing has been attempted.

Meanwhile, when the light source 2 is provided in the same housing as the measurement unit 3 and the control unit 6, the light source 2 is provided close to the measurement unit 3 and the control unit 6. For this reason, due to heat from the measurement unit 3 and the control unit 6, there are cases in which operations of the light source 2 become unstable, the intensity of laser light output from the light source 2 accordingly fluctuates, and accordingly, the fluctuation of the intensity appears as noise in a generated image.

Particularly, as the image acquisition device 1 according to the present embodiment, when an observation result of the microscope unit 4 (for example, two-photon excitation microscope) is made as an image, the image is generated by scanning the sample S, and thus a photographing rate depends on a control rate of the galvano mirror 51 that is used in the scanning or a detection rate of the PMT 53. Due to the configuration, the photographing rate is lower than that of an apparatus such as a so-called camera that generates images using an imaging device in many cases, and tends to decrease in proportion to an increase of an image size. For this reason, in the configuration in which excitation light emitted from the light source 2 is radiated to the sample S and an image is generated based on fluorescence from the sample S, there are many cases in which thermal fluctuation of the intensity of laser light emitted from the light source 2 appears as noise on an image.

1.5. Configuration of an Image Acquisition Device

<<1.5.1. Overview>>

In consideration of the problem described above, the image acquisition device 1 according to the present embodiment is intended to achieve miniaturization by mounting the light source 2 inside the device (in the same housing), to reduce noise accompanied by thermal fluctuation of laser light emitted from the light source 2, and thereby to be capable of acquiring a more vivid image.

To be specific, the image acquisition device 1 according to the present embodiment measures the intensity of laser light emitted from the light source 2, and based on intensity distribution of the measured laser light, executes at least any of control of the intensity of the laser light emitted from the light source 2 and correction of a generated image.

For example, the image acquisition device 1 according to the present embodiment corrects the generated image based on the intensity distribution of the measured laser light and thereby can reduce noise that is accompanied by thermal fluctuation of the laser light and appears on the image.

In addition, the image acquisition device 1 according to the present embodiment controls the intensity of the laser light based on the intensity distribution of the measured laser light and thereby can stabilize the laser light that has been unstable due to thermal fluctuation.

Hereinafter, with regard to the image acquisition device 1 according to the present embodiment, an example of a configuration of the light source 2 will be first described, and then an optical system and a functional configuration of the image acquisition device 1 according to the present embodiment will be described. Note that, since a configuration of the microscope unit 4 is the same as in the image acquisition device 1w according to the comparative example described above, detailed description thereof will be omitted.

<<1.5.2. Configuration of a Light Source>>

Figure 13A:
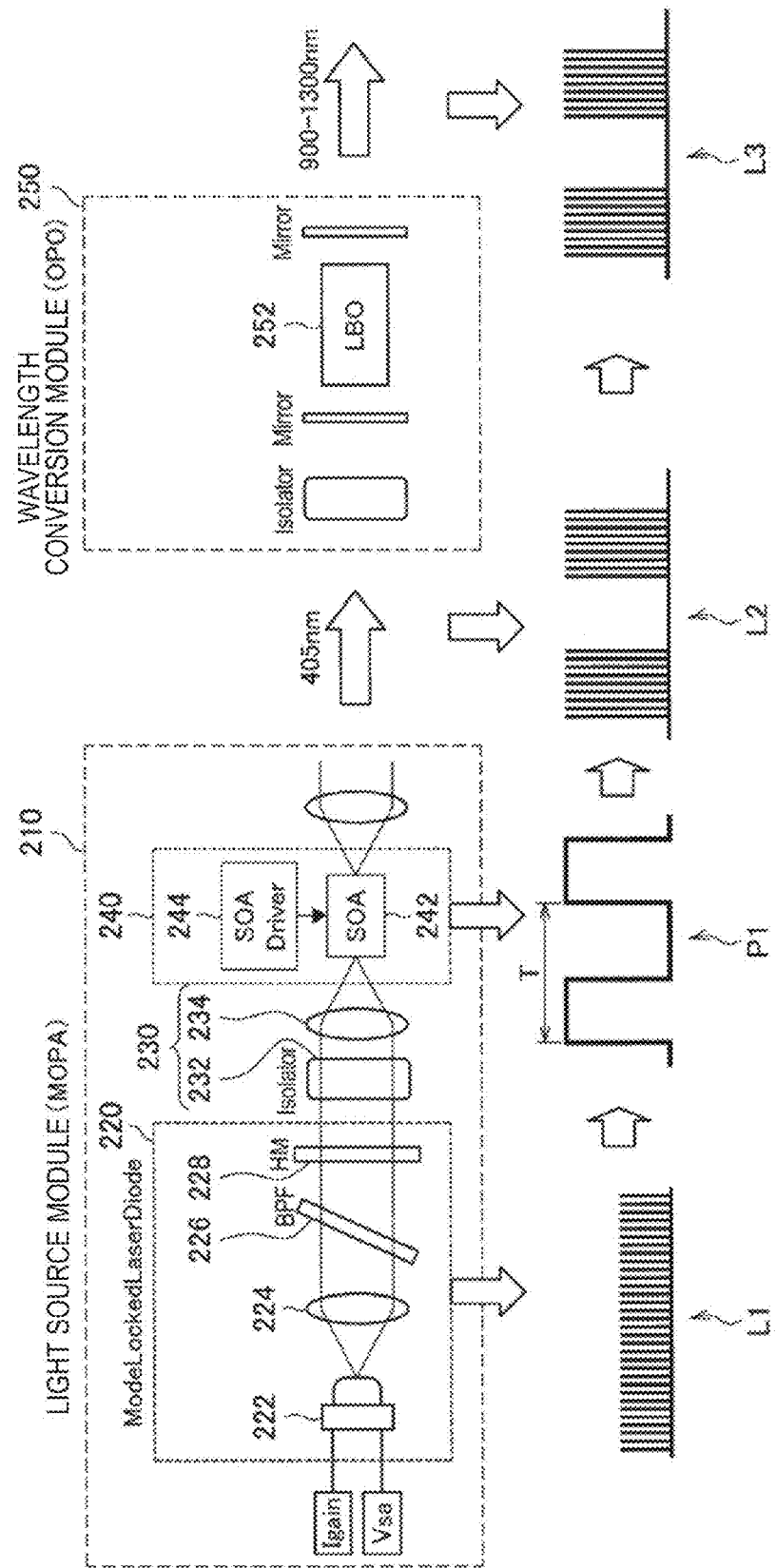
FIG. 13A is a schematic diagram showing a detailed configuration of a light source according to the embodiment.

First, an example of the configuration of the light source 2 used in the image acquisition device 1 according to the present embodiment will be described. The image acquisition device 1 according to the present embodiment uses, as the light source 2, a light source that includes, for example, an oscillating unit such as an optical parametric oscillator and is configured to be capable of changing a wavelength of emitted laser light by changing an oscillation condition of the oscillating unit. Hereinbelow, the example of the configuration of the light source 2 will be described with reference to FIG. 13A. FIG. 13A is a schematic diagram showing the configuration of the light source 2 in detail.

The light source 2 is constituted by an MOPA 210 in which a mode-locked oscillating laser is combined with a light amplifier and a wavelength conversion module (OPO) 250. The MOPA 210 has a mode-locked laser unit (mode-locked laser diode) 220, an optical isolator unit 230, and an optical amplifier unit (SOA unit) 240.

In addition, in the lower part of FIG. 13A, pulse waveforms L1, L2, and L3 of laser light output from the mode-locked laser unit 220, the optical amplifier unit 240, and the wavelength conversion module 250, respectively, and a pulse waveform P1 for intermittent drive to be described later are shown.

The mode-locked laser unit 220 is configured to include elements of a semiconductor laser 222, a lens 224 through which laser light emitted from the semiconductor laser 222 passes, a bandpass filter 226, and a mirror 228. The bandpass filter 226 has a function of transmitting light of a certain wavelength range therethrough and not allowing light out of the range to pass therethrough. In addition, an external resonator (spatial resonator) is formed between a mirror on a rear end face of the semiconductor laser 222 and the mirror 228, and a frequency of laser light emitted from the mode-locked laser unit 220 is decided based on a length of the path of the external resonator. Accordingly, it is possible to intentionally lock a specific frequency and a mode of the laser light.

The mode-locked laser unit 220 can be synchronized with a short pulse in a cycle longer than that of a normal semiconductor laser (for example, about 1 GHz) by having the external resonator. For this reason, laser light L1 output from the mode-locked laser unit 220 has low average power and a high peak, which leads to little damage to a biological tissue and thus photon efficiency increases.

The optical isolator unit 230 is disposed in the later stage of the mode-locked laser unit 220. The optical isolator unit 230 is configured to include an optical isolator 232 and a mirror 234. The optical isolator unit 230 has a function of preventing light reflected in an optical component or the like disposed in the later stage from being incident on the semiconductor laser 222.

The optical amplifier unit (SOA unit) 240 functions as an optical modulation unit that modulates the laser light emitted from the semiconductor laser 222 to be amplified, and is disposed in the later stage of the optical isolator unit 230. The laser light output from the mode-locked laser unit 220 is amplified by the optical amplifier unit 240 due to its relatively small power. The optical amplifier unit 240 is constituted by, a semiconductor optical amplifier (SOA), i.e., a semiconductor optical amplifying unit 242 and an SOA driver 244 that controls the semiconductor optical amplifying unit 242. The semiconductor optical amplifying unit 242 is a small and inexpensive optical amplifier, and can be used as an optical gate or an optical switch that turns on and off light. In the present embodiment, by turning-on and turning-off of the semiconductor optical amplifying unit 242, the laser light emitted from the semiconductor laser 222 is modulated.

The optical amplifier unit (SOA unit) 240 amplifies the laser light according to sizes of a control current (direct current). Further, by performing intermittent drive using the control current of the pulse waveform P1 shown in FIG. 13A at the time of amplification, the optical amplifier unit 240 turns on and off the laser light of the pulse waveform L1 in a predetermined cycle T to output intermittent laser light (of the pulse waveform L2). By generating pulse waveforms at a desired timing and cycle as above, it is possible to synchronize with a control signal of a system. As described above, it is possible to realize intermittent drive in the case of a MOPA-type light source by performing intermittent drive in the semiconductor optical amplifying unit 242 (or semiconductor optical amplifier which is abbreviated as SOA) in the later stage that amplifies the pulse of the oscillating unit in the front stage. In the MOPA-type light source, the optical amplifier unit 240 (semiconductor amplifying unit 242) functions as an intermittent light emitting unit.

Since the MLLD is used in the present embodiment, a frequency of the laser light output from the semiconductor laser 222 is 500 MHz to 1 GHz, for example, and a pulse width thereof is about 0.5 to 1.0 ps. As will be described later, by receiving injection of an oscillation synchronization signal from the oscillation synchronization signal injection unit 316, it is possible to synchronize a control signal of the system with an oscillation pulse output from the semiconductor laser 222 in addition to synchronization of intermittent drive by the SOA unit. Note that, when TiSa is used, an oscillation frequency of the laser light is about 40 MHz to 80 MHz, and a pulse width thereof is about 0.1 to 0.2 ps, however, laser light having a higher oscillation frequency can be output when the MLLD is used.

In the present embodiment, a wavelength of laser light output from the optical amplifier unit 240 is 405 nm, for example. Since the wavelength of 405 nm is a wavelength that undergoes absorption relatively easily, it is converted to a wavelength that brings an effect of two photons with high density when it reaches deep inside a biological tissue (about 900 nm to 1300 nm). For this reason, the laser light output from the optical amplifier unit 240 is input to the wavelength conversion module 250 provided in the later stage and the wavelength thereof is converted by an LBO 252 of the wavelength conversion module 250.

The LBO 252 of the wavelength conversion module 250 converts the input laser light (of the pulse waveform L2) so as to have two wavelengths, for example. Note that, in the converted laser light having the two wavelengths, one corresponds to signal light and the other corresponds to idler light. In the light source 2 according to the present embodiment, one laser light of the signal light and the idler light is output from the wavelength conversion module 250 to the outside and radiated on a target object (sample S).

Note that, in the example shown in FIG. 13A, the laser light having a longer wavelength (of the pulse waveform L3) out of the converted laser light having the two wavelengths is output from the wavelength conversion module 250 as the signal light, and radiated on the target object (sample S). In this case, the laser light having a shorter wavelength out of the converted laser light having the two wavelengths corresponds to the idler light.

In observation of a biological tissue using a laser microscope, however, it is effective to lower average power of the laser and to heighten peak power thereof in order to decrease damage to the target object. In addition, an operation of a laser chip that constitutes an MOPA-type light source using a semiconductor laser is considered to be limited by heating that is caused by a load of high electric power since the chip has a small size.

Since the light source 2 of the present embodiment intermittently operates by intermittently outputting laser light (of the pulse waveform L2), the average electric power is the same as when the intermittent operation is not performed, however, the peak when it emits light can be further heightened. In addition, by performing the intermittent operation, heating caused by a load of high electric power can also be suppressed.

In the present embodiment, the light source 2 is used as a light source for two-photon excitation, and thus the light source 2 causes a fluorescent substance to be excited by two photons. Particularly, a figure of merit of a microscope that uses a two-photon excitation light source is known as FOM (=(peak power)$^2$×pulse width×frequency=peak power×average power). According to the figure of merit, it is possible to increase output in proportion to the product of peak power and average power. Thus, in order to raise output by suppressing damage to a target object to the minimum in observation of a biological tissue using a laser microscope, it is effective to raise peak power by lowering average power. For this reason, in the present embodiment, the peak power is raised by performing an intermittent operation and thereby lowering a duty (duty=pulse width×frequency) ratio.

FIG. 13B is a characteristic diagram showing a state in which peak power of a laser has been raised through intermittent light emission. The upper part of FIG. 13B shows characteristics of one-photon excitation, and the characteristic on the upper-left side indicates peak power of continuous light emission, and the characteristic on the right side indicates peak power of intermittent light emission when the duty ratio is set to 50%. When the duty ratio of intermittent light emission is set to 50% as above, the intermittent light emission can output signal intensity double ($2 \times I_0$) a signal intensity ($I_0$) of the continuous light emission.

In addition, the middle part of FIG. 13B shows characteristics of two-photon excitation, the characteristic on the left side indicates peak power of continuous light emission, and the characteristic on the right side indicates peak power of intermittent light emission when the duty ratio is set to 50%. According to the figure of merit FOM, two-photon excitation has a high figure of merit that is equal to the square of the peak power. Thus, a signal intensity of two-photon excitation in intermittent light emission is four times ($=4 \times I_0^2$) a signal intensity of continuous light emission ($=I_0^2$). In addition, with regard to the average signal intensity of a pulse light emission point and a pulse non-light emission point, the average signal intensity of two-photon excitation is double ($=2 \times I_0^2$) the signal intensity of continuous light emission ($=I_0^2$). Thus, according to the present embodiment, by intermittently driving the light source 2 for two-photon excitation, it is possible to raise the peak power and the average signal intensity.

Characteristics in the lower part of FIG. 13B indicate signals having the characteristics in the middle part which have passed through a band-limited low-pass filter. Since the process using the band-limited low-pass filter is inserted before A-D conversion, when an on-off duty ratio is 50% (½), the signal amplitude before A-D conversion becomes ½, and as a result, intermittent light emission for two-photon excitation can obtain double the signal amplitude. In addition, when the on-off duty ratio is 1/n, if the peak power is multiplied by n, the signal amplitude obtained in the two-photon excitation is multiplied by n, and thus a small duty is desirable, however, since there is actually an upper limit on peak power obtained from the light source 2, it is preferable to select an appropriate value of a duty ratio that is equal to or smaller than 1.

<<1.5.3. Configuration of an Optical System>>

Figure 14:
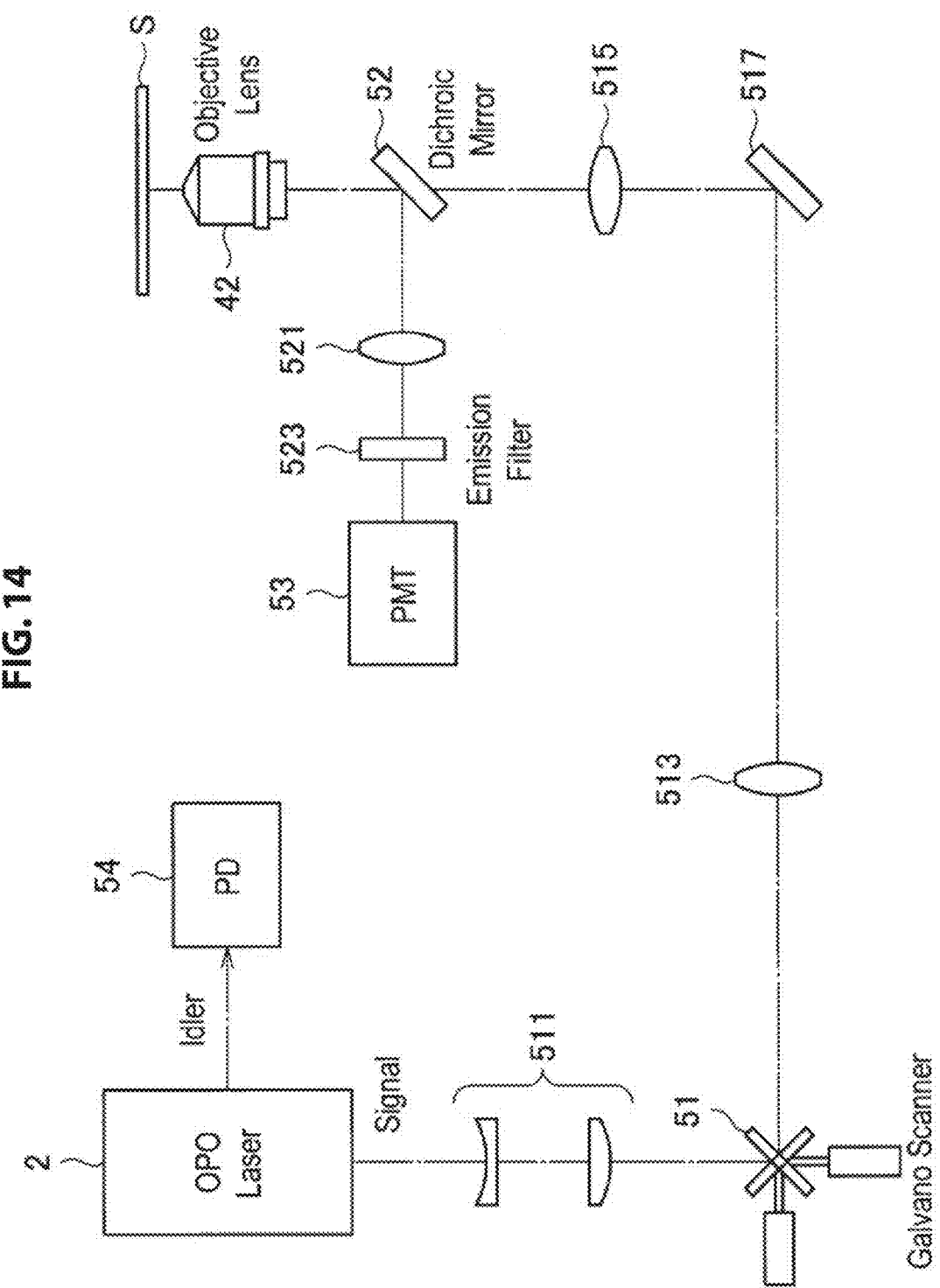
FIG. 14 is an illustrative diagram showing an example of a configuration of an optical system of the image acquisition device according to the first embodiment of the present disclosure.

Next, a configuration of an optical system of the image acquisition device 1 according to the present embodiment will be described with reference to FIG. 14 particularly focusing on different portions from the configuration of the optical system (refer to FIG. 10) of the image acquisition device 1w according to the comparative example described above.

As described above, in the image acquisition device 1 according to the present embodiment, the light source 2 includes the wavelength conversion module (OPO) 250, thereby converting an input laser light (pump light) into laser light having two wavelengths (in other words, signal light and idler light) and then outputs them. In the image acquisition device 1 according to the present embodiment, any one of the signal light and the idler light output from the light source 2 is radiated toward the sample S as excitation light. The example shown in FIG. 14 is configured such that the signal light is radiated toward the sample S as excitation light.

Note that the configuration in which excitation light is radiated toward the sample S is the same as the optical system of the image acquisition device 1w (refer to FIG. 10) according to the comparative example described above. In other words, the excitation light emitted from the light source 2 is guided to the objective lens 42 via the beam-forming lens 511, the galvano mirror 51, the lens 513, the mirror 517, the lens 515, and the dichroic mirror 52, and then collected toward the sample S by the objective lens 42.

In addition, when the sample S is irradiated with the excitation light, some molecules of the sample S are excited by the excitation light and thereby emit fluorescence, and the fluorescence forms an image on the detection plane of the PMT 53 via the objective lens 42, the dichroic mirror 52, the image-forming lens 521, and the emission filter 523. At this time, light other than colored light (natural light) that has been enlarged by the objective lens 42 is absorbed by the emission filter 523, (in other words, only the colored light is transmitted therethrough), and then an image of the colored light that has lost the natural light is formed on the PMT 53.

In addition, the image acquisition device 1 according to the present embodiment is provided with a PD (photodetector) 54 to detect an intensity of one beam that is different from the other beam that is used as excitation light between the signal light and the idler light. In the example shown in FIG. 14, the PD 54 measures an intensity of the idler light emitted from the light source 2.

<<1.5.4. Functional Configuration of an Image Acquisition Device>>

Next, an example of a functional configuration of the image acquisition device 1 according to the present embodiment will be described with reference to FIG. 15 particularly focusing on a configuration of the control unit 6. Note that, in the example shown in FIG. 15, each constituent element of the scanning system (detection system) 5 corresponds to the constituent element of the optical system shown in FIG. 14 to which the same reference numeral is given. In addition, some of the constituent elements shown in FIG. 14 are omitted in the example shown in FIG. 15.

Figure 15:
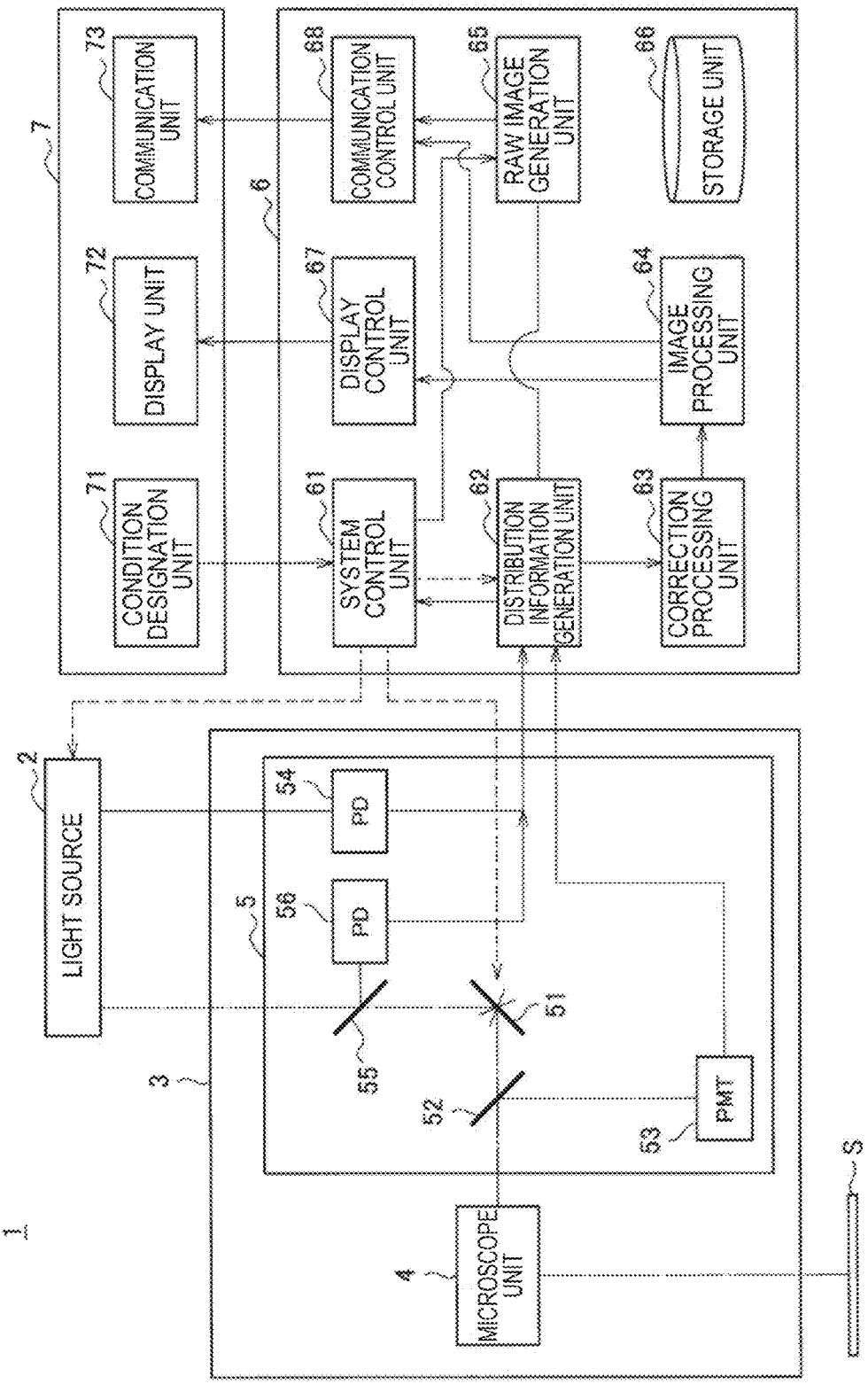
FIG. 15 is an illustrative diagram for describing an example of a functional configuration of the image acquisition device according to the embodiment.

As shown in FIG. 15, the image acquisition device 1 according to the present embodiment includes the light source 2 inside the device (inside its housing) to radiate excitation light emitted from the light source 2 to the sample S via the scanning system (detection system) 5 and the microscope unit 4. At this time, as a system control unit 61 controls an operation of the galvano mirror 51, the excitation light scans the top of the sample S. Note that, in order to facilitate understanding of description, description will be provided hereinafter on the assumption that, between the signal light and the idler light both emitted from the light source 2, the signal light is used as excitation light.

Fluorescence generated from the sample S by the radiated excitation light is guided to the scanning system (detection system) 5 via the microscope unit 4, and then detected by the PMT 53 of the scanning system (detection system) 5. The PMT 53 converts the detected fluorescence into an electric signal through photoelectric conversion at a sampling rate set in advance, and outputs the signal to the control unit 6 as data indicating an intensity of the fluorescence.

In addition, the scanning system (detection system) 5 of the image acquisition device 1 according to the present embodiment includes the PD 54, and the PD 54 measures an intensity of the idler light at a sampling rate set in advance. The PD 54 converts the intensity of the measured idler light into an electric signal and then outputs the signal as data indicating the intensity of the idler light to the control unit 6.

Note that, instead of the PD 54, a PD 56 that measures an intensity of the excitation light (signal light) may be provided. In this case, a beam splitter 55 may be provided on the optical path of the excitation light (signal light) radiated toward the sample S to bifurcate part of the excitation light (signal light) being guided toward the sample S toward the PD 56. Note that, hereinafter, the scanning system (detection system) 5 will be described on the assumption that the PD 54 is provided therein to measure the intensity of the idler light.

The control unit 6 includes the system control unit 61, a distribution information generation unit 62, a correction processing unit 63, the image processing unit 64, the raw image generation unit 65, the storage unit 66, the display control unit 67, and the communication control unit 68. In addition, the I/F 7 includes the condition designation unit 71, the display unit 72, and the communication unit 73. Note that, since operations of the storage unit 66, the display control unit 67, the communication control unit 68, the condition designation unit 71, the display unit 72, and the communication unit 73 are the same as the image acquisition device 1w according to the comparative example described above, detailed description thereof will be omitted.

The system control unit 61 controls operations of the light source 2 and the galvano mirror 51 based on a measurement condition designated by a user via the condition designation unit 71. The condition designation unit 71 is an input I/F with which the user designates a measurement condition for measurement and image acquisition. For example, the user can designate scanning conditions for output of the light source 2 and scanning of the sample S (for example, a range to be scanned or resolution of a generated image) as a measurement condition through the condition designation unit 71.

The system control unit 61 controls operations of the galvano mirror 51 based on a scanning condition designated by a user as a measurement condition, and causes control information that indicates the content of the control to be output to two-dimensionalization processing units 621 and 625 to be described later. The operations described so far are the same as those of the image acquisition device 1w according to the comparative example described above (refer to FIG. 12).

Note that the system control unit 61 may control operations of the light source 2 and the galvano mirror 51 based on the control information that indicates a measurement condition decided in advance. For example, when the sample S is already known, a wavelength and output of laser light output from the light source 2 may be controlled based on control information prepared in advance corresponding to the sample S. Note that such control information may be stored in, for example, the storage unit 66 in advance.

In addition, the system control unit 61 according to the present embodiment acquires data that indicates intensity distribution that is based on intensities of the idler light from the distribution information generation unit 62 to be described later, and controls operations of the light source 2 based on the acquired data.

Figure 16:
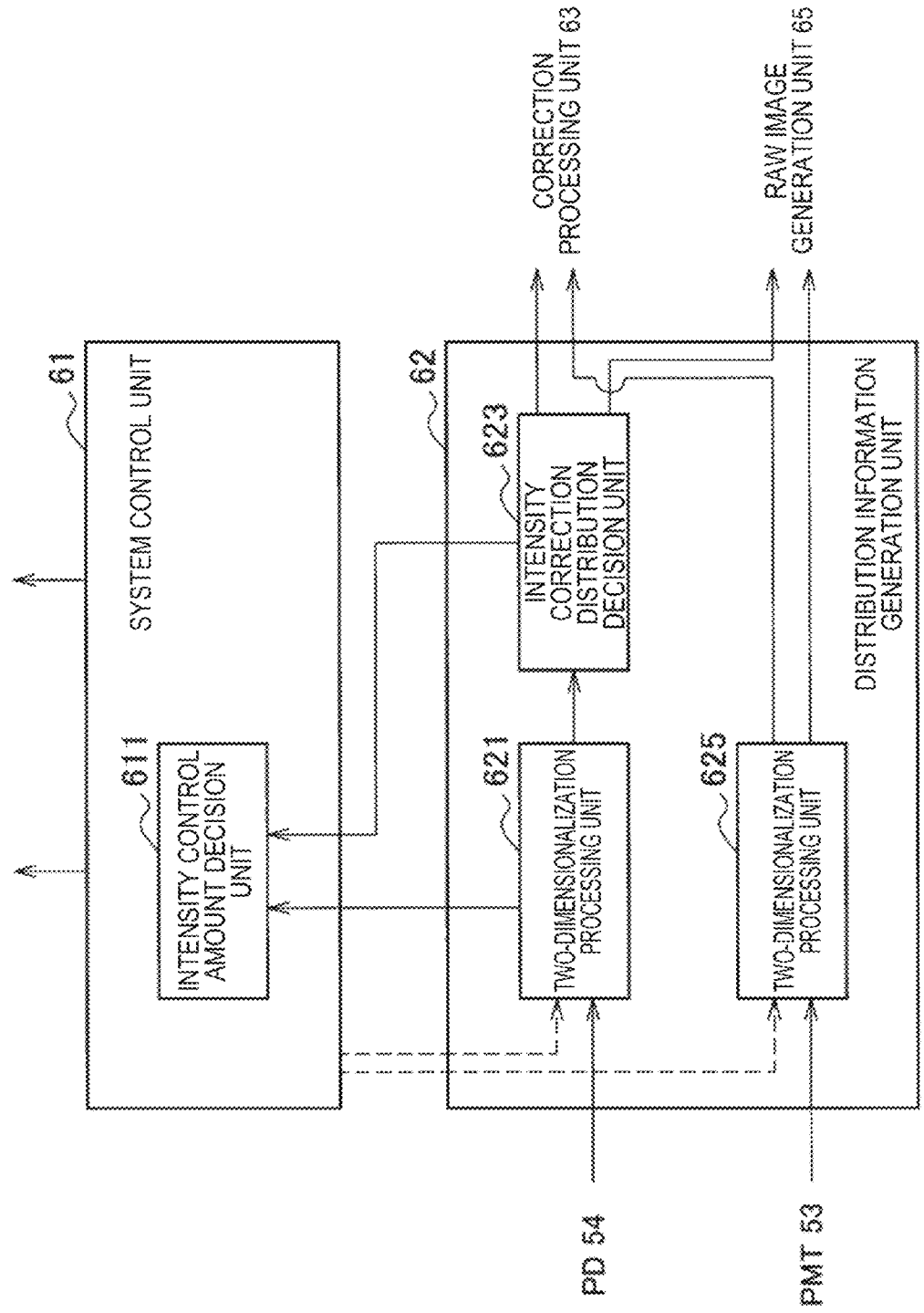
FIG. 16 is an illustrative diagram for describing detailed functional configurations of a distribution information generation unit and a system control unit according to the embodiment.

Herein, a more detailed configuration of the system control unit 61 will be described with reference to FIG. 16. FIG. 16 is an illustrative diagram for describing detailed functional configurations of the distribution information generation unit 62 and the system control unit 61 according to the present embodiment. As shown in FIG. 16, the system control unit 61 includes an intensity control amount decision unit 611.

The intensity control amount decision unit 611 acquires data that indicates intensity distribution that is based on intensities of the idler light measured by the PD 54 from the two-dimensionalization processing unit 621 of the distribution information generation unit 62 to be described later. In addition, the intensity control amount decision unit 611 is informed of a maximum gap of correction amounts from an intensity correction distribution decision unit 623 of the distribution information generation unit 62 to be described later. The intensity control amount decision unit 611 monitors states of the light source 2 (particularly, changes in the intensity of excitation light) based on the acquired data that indicates the intensity distribution of the idler light and the maximum gap of correction amounts.

In addition, the intensity control amount decision unit 611 generates control information for controlling the intensity of laser light (pump light) emitted from the light source 2 based on a monitoring result. The system control unit 61 controls the intensity of the laser light (pump light) emitted from the light source 2 based on the control information generated by the intensity control amount decision unit 611.

With the configuration described above, when, for example, an operation of the light source 2 is unstable (for example, when fluctuation of the intensity of the emitted laser light occurs), the system control unit 61 can control the intensity of the laser light (pump light) emitted from the light source 2 so that the light source 2 can stably operate. Note that details of the control of the light source 2 by the system control unit 61, in other words, intensity control of the laser light emitted from the light source 2, will be described later separately in "1.8. Details of intensity control of laser light."

Next, details of the distribution information generation unit 62 will be described with reference to FIGS. 15 and 16. As shown in FIG. 16, the distribution information generation unit 62 includes the two-dimensionalization processing unit 621, the intensity correction distribution decision unit 623, and another two-dimensionalization processing unit 625.

The two-dimensionalization processing unit 621 sequentially acquires the data that indicates the intensities of the idler light detected (measured) by the PD 54 at a sampling rate set in advance from the PD 54. In addition, the two-dimensionalization processing unit 621 sequentially acquires the control information that indicates the content of control of the galvano mirror 51 from the system control unit 61. Accordingly, the two-dimensionalization processing unit 621 can ascertain data at what position on the sample S which corresponds to the data indicating the intensities of the idler light acquired from the PD 54 based on the control information acquired from the system control unit 61. In other words, by performing two-dimensionalization on the data indicating the intensities of the idler light sequentially acquired from the PD 54 in series based on the control information acquired from the system control unit 61, the two-dimensionalization processing unit 621 generates intensity distribution of the detected idler light.

Figure 17:
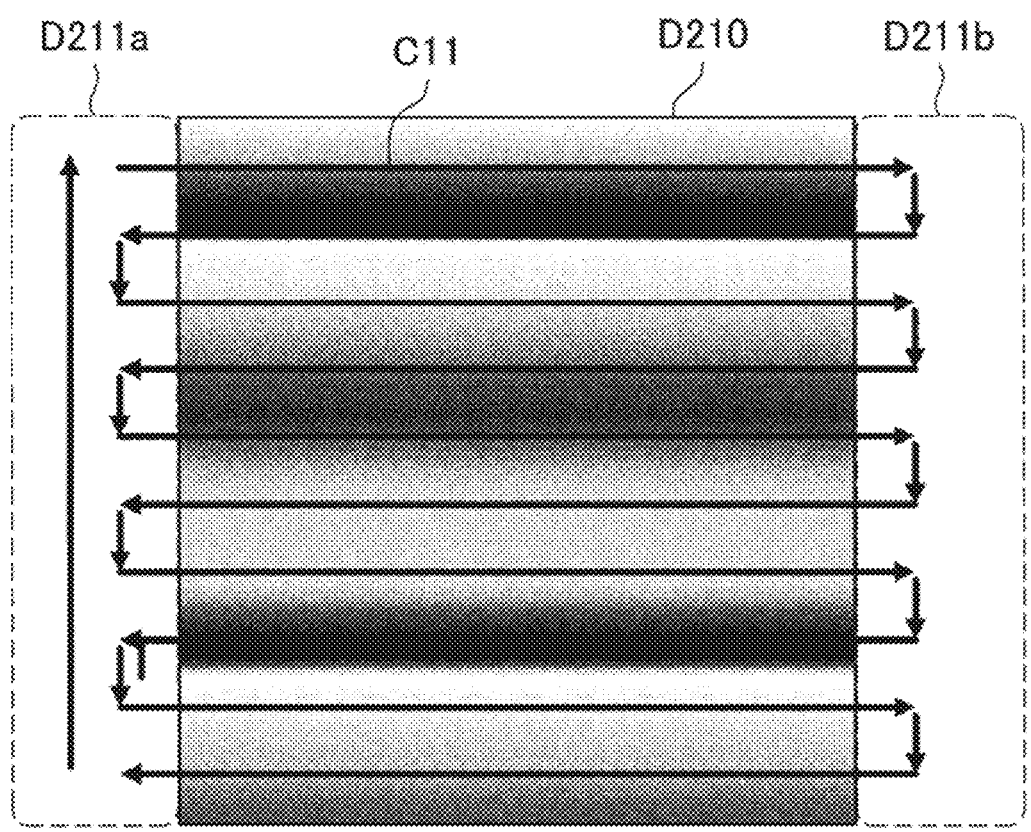
FIG. 17 is an illustrative diagram for describing an example of an operation of a two-dimensionalization processing unit according to the embodiment.

FIG. 17 will be referred to herein. FIG. 17 is an illustrative diagram for describing an example of an operation of the two-dimensionalization processing unit 621. In FIG. 17, reference numeral C11 schematically shows the content of control of the galvano mirror 51, i.e., the content of scanning of the top of the sample S using excitation light. The two-dimensionalization processing unit 621 performs two-dimensionalization on the data that indicates the intensities of the idler light sequentially acquired from the PD 54 in series based on the content of scanning indicated by control information to generate intensity distribution D21.

Note that there are cases in which the intensity of laser light (pump light) output from the light source 2 changes when it is affected by heating of each component (for example, the measurement unit 3 of the control unit 6) inside the image acquisition device 1 as described above. At that moment, along with the change in the intensity of the pump light, intensities of signal light and idler light also change in the same manner as the pump light. For this reason, the change of the intensity of the idler light is expressed as, for example, strength of an electric signal converted by the PD 54.

Note that, in the generated intensity distribution D21, regions D211a and D211b of the ends at which a scanning direction switches may be eliminated as unnecessary portions, and a remaining region D210 may be left as a valid portion. The elimination of the unnecessary portions D211a and D211b may be performed by, for example, the two-dimensionalization processing unit 621 or by the correction processing unit 63 to be described later. In addition, an operation of the two-dimensionalization processing unit 625 to be described later performed when it generates intensity distribution that is based on intensities of fluorescence detected by the PMT 53 is also the same as that of the two-dimensionalization processing unit 621 described with reference to FIG. 17.

The two-dimensionalization processing unit 621 outputs the data that indicates the generated intensity distribution of the idler light (which may be referred to hereinbelow simply as "intensity distribution of the idler light") to the intensity correction distribution decision unit 623 and the intensity control amount decision unit 611.

The intensity correction distribution decision unit 623 acquires the intensity distribution of the idler light from the two-dimensionalization processing unit 621. The intensity correction distribution decision unit 623 generates correction data for correcting intensity distribution of fluorescence by the correction processing unit 63 to be described later based on the acquired intensity distribution of the idler light.

In addition, the intensity correction distribution decision unit 623 may acquire the intensity distribution of the idler light in advance during a warm-up period, and then compute the maximum gap of correction amounts based on the intensity distribution of the idler light of the warm-up period. Note that the maximum gap of correction amounts computed as above indicates a maximum gap (margin) of a correction amount of intensity distribution of fluorescence and a control amount of the intensity of laser light (pump light) emitted from the light source 2 based on a temporal change in the number of photons caused by a change in the intensity of laser light emitted from the light source 2. For this reason, the intensity correction distribution decision unit 623 may inform the intensity control amount decision unit 611 of the computed maximum gap of correction amounts.

The intensity correction distribution decision unit 623 outputs the intensity distribution of the idler light to the raw image generation unit 65, and correction data generated based on the intensity distribution of the idler light to the correction processing unit 63.

The two-dimensionalization processing unit 625 sequentially acquires the data that indicates the intensities of the fluorescence detected (measured) by the PMT 53 at a sampling rate set in advance from the PMT 53. In addition, the two-dimensionalization processing unit 625 sequentially acquires the control information that indicates the content of control of the galvano mirror 51 from the system control unit 61. Accordingly, the two-dimensionalization processing unit 625 can ascertain data at what position on the sample S which corresponds to the data indicating the intensities of the fluorescence acquired from the PMT 53 based on the control information acquired from the system control unit 61. In other words, by performing two-dimensionalization on the data indicating the intensities of the fluorescence sequentially acquired from the PMT 53 in series based on the control information acquired from the system control unit 61, the two-dimensionalization processing unit 625 generates intensity distribution of the detected fluorescence.

The two-dimensionalization processing unit 625 outputs the generated data that indicates the intensity distribution of the fluorescence (which may be referred to hereinafter simply as "intensity distribution of the fluorescence") to the correction processing unit 63 and the raw image generation unit 65.

The correction processing unit 63 acquires the intensity distribution of the fluorescence from the two-dimensionalization processing unit 625. In addition, the correction processing unit 63 acquires the correction data generated based on the intensity distribution of the idler light from the intensity correction distribution decision unit 623.

Figure 18:
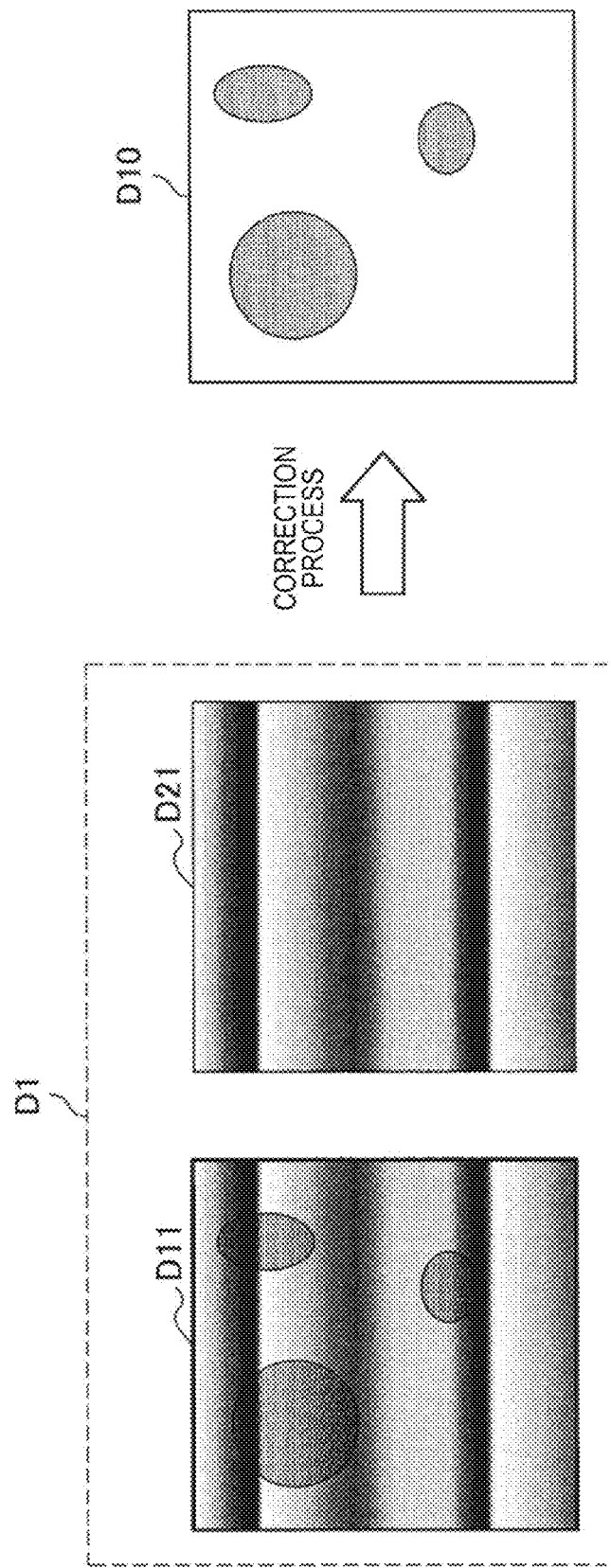
FIG. 18 is an illustrative diagram for describing an overview of a correction process according to the embodiment.

The correction processing unit 63 corrects the intensity distribution of the fluorescence based on the correction data. An overview of the correction by the correction processing unit 63 will be described herein with reference to FIG. 18. It is an illustrative diagram for describing the overview of the correction process according to the present embodiment. In FIG. 18, reference numeral D11 indicates schematic intensity distribution of the fluorescence generated by the two-dimensionalization processing unit 625. In addition, reference numeral D21 indicates schematic intensity distribution of the idler light generated by the two-dimensionalization processing unit 621. In addition, reference numeral D10 indicates intensity distribution of the fluorescence after the correction process (in other words, a raw image).

Note that, as described above, there are cases in which the intensity of laser light (pump light) output from the light source 2 changes when it is affected by heating of each component present inside the image acquisition device 1, and thus intensities of the signal light and idler light also change like the pump light. For this reason, the change in the intensity of the signal light appears as noise in the intensity distribution of the fluorescence, and likewise, the change in the intensity of the idler light appears as noise in the intensity distribution of the idler light. Meanwhile, the signal light and the idler light are output by converting the pump light by the wavelength conversion module (OPO) 250. For this reason, the intensity distribution of the signal light is syntonized with the intensity distribution of the idler light at all times. In other words, the intensity of the signal light and the intensity of the idler light are in a proportional relation at all times.

For that reason, using the feature described above, the correction processing unit 63 according to the present embodiment corrects noise that has appeared in the intensity distribution of the fluorescence due to the change in the intensity of the signal light with the correction data generated based on the intensity distribution of the idler light. The correction processing unit 63 outputs the intensity distribution of the fluorescence that has been corrected with the correction data to the image processing unit 64.

Note that details of the generation of the correction data by the intensity correction distribution decision unit 623 and the operation relating to the correction of the intensity distribution of the fluorescence by the correction processing unit 63 based on the correction data will be described later separately in "1.7. Details of a correction process"

The image processing unit 64 acquires the intensity distribution of the fluorescence corrected with the correction data. The image processing unit 64 generates image data by performing image processing such as a compression process on the corrected intensity distribution of the fluorescence.

The image processing unit 64 outputs the generated image data to, for example, the display control unit 67. In addition, the image processing unit 64 may output the generated image data to the communication control unit 68. In addition, the image processing unit 64 may cause the generated image data to be stored in the storage unit 66.

In addition, the correction process performed on the intensity distribution of the fluorescence D11 based on the correction data shown above may be performed by an external device, for example, the information processing device 800. For this reason, the raw image generation unit 65 according to the present embodiment may associate a raw file D1 generated as image data (a raw image) from the intensity distribution of the fluorescence D11 with the intensity distribution of the idler light D21.

As described above, by associating the raw file D1 with the intensity distribution of the idler light D21, an external device (for example, the information processing device 800) that has read the raw file D1 can correct noise accompanied by a change in the intensity of laser light like the correction processing unit 63.

The raw image generation unit 65 outputs the generated raw file to, for example, the communication control unit 68. In addition, the raw image generation unit 65 may cause the generated raw file to be stored in the storage unit 66.

Hereinabove, the configuration of the image acquisition device 1 according to the present embodiment has been described with reference to FIGS. 13A, 13B, and 14 to 18.

Next, more details of each configuration of the image acquisition device 1 according to the present embodiment will be described.

1.6. File Format of a Raw File

Figure 19:
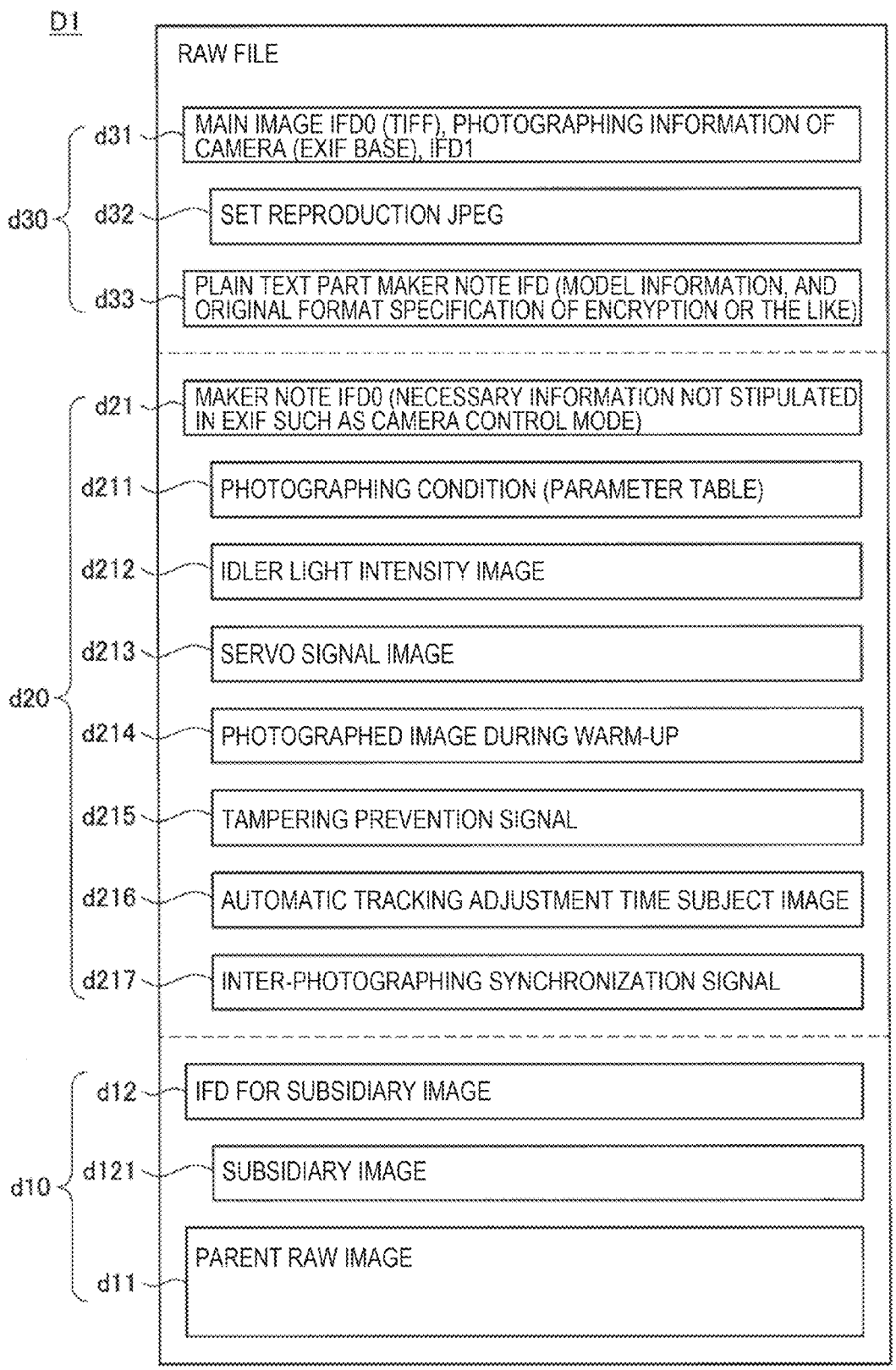
FIG. 19 is a diagram showing an example of a file format of a raw file according to the embodiment.

First, an example of a file format of the raw file D1 according to the present embodiment will be described with reference to FIG. 19. FIG. 19 is a diagram showing the example of the file format of the raw file D1 according to the present embodiment.

As shown in FIG. 19, the raw file D1 according to the present embodiment includes, for example, a data area d10, a basic control information area d30, and an extended area d20.

The data area d10 is an area for storing image data (actual data). As shown in FIG. 19, the data area d10 includes, for example, a parent raw image d11, an image file or director (IFD) for subsidiary images d12, and a subsidiary image d121. The parent raw image d11 indicates a raw image. The raw file D1 according to the present embodiment stores the intensity distribution of the fluorescence D11 as the parent raw image d11. Note that the number of pieces of the intensity distribution of the fluorescence D11 stored as the parent raw image d11 is not limited to one (one slice). For example, when a plurality of pieces of the intensity distribution of the fluorescence D11, which has been created by performing scanning in an X-Y direction (plane direction), are acquired in a Z direction (depth direction), the plurality of pieces of the intensity distribution of the fluorescence D11 may be stored in the raw file D1 as the parent raw image d11.

In addition, the data area d10 may set to be able to separately store image data that has undergone image processing or images such as data of enlarged or reduced images that have undergone image processing as subsidiary images. In this case, the IFD for subsidiary images d12 for storing such subsidiary images may be provided and the subsidiary image d121 may be stored in the IFD for subsidiary images d12. Note that the IFD for subsidiary images d12 is in charge of indicating a position (address) of the subsidiary image d121 in the raw file D1.

In addition, various kinds of information decided in advance are recorded as control information in the basic control information area d30. The basic control information area d30 includes, for example, a main image and photographing information IFD d31, set reproduction JPEG d32, and a plain text part maker note IFD d33. The main image and photographing information IFD d31 is an IFD for storing, for example, image data used in reproduction and photographing information (for example, meta information such as an exchangeable image file format (EXIF)).

The main image and photographing information IFD d31 stores, for example, image data used in reproduction of images (for example, data obtained after a compression process) as the set reproduction JPEG d32.

In addition, the plain text part maker note IFD d33 stores model information of the image acquisition device 1 and information indicating an encryption format or the like as control information. Note that such control information may be stored in, for example, the storage unit 66 in advance, read by the raw image generation unit 65 from the storage unit 66, and embedded in the raw file D1.

The extended area d20 includes a maker note IFD d21. The maker note IFD d21 is an IFD for storing information such as a camera control mode that is not stipulated in the EXIF, and also storing photographing information and control information intrinsic to the image acquisition device 1.

The maker note IFD d21 according to the present embodiment includes, for example, a photographing condition d211, an idler light intensity image d212, a servo signal image d213, a warm-up time photographed image d214, a tampering prevention signal d215, an automatic tracking adjustment time subject image d216, and an inter-photographing synchronization signal d217.

The photographing condition d211 is control information that indicates a condition that is not stipulated in the EXIF among photographing conditions at the time of acquiring a raw image (in other words, the intensity distribution of the fluorescence). The photographing condition d211 includes control information that indicates each condition in the form of, for example, a parameter table.

The idler light intensity image d212 indicates the intensity distribution of the idler light D21. Note that, when a plurality of pieces of the intensity distribution of the fluorescence D11 are recorded as the parent raw image d11, the intensity distribution of the idler light D21 corresponding to each of the plurality of pieces of the intensity distribution of the fluorescence D11 is recorded as the idler light intensity image d212. In addition, for the idler light intensity image d212, correction data computed based on the intensity distribution of the idler light D21 may be used instead of the intensity distribution of the idler light D21.

As described above, by storing the idler light intensity image d212 in the raw file D1, an external device (for example, the information processing device 800) that has read the raw file D1 can correct the parent raw image d11 like the correction processing unit 63 described above.

The servo signal image d213 is data obtained by performing two-dimensionalization on a servo signal that is used by the system control unit 61 to control the intensity of the laser light emitted from the light source 2 based on a scanning condition. By storing the servo signal image d213 in the raw file D1, it is possible to recognize what kind of control the external device (for example, the information processing device 800) that has read the raw file D1 has performed on the light source 2 at the time of acquiring the intensity distribution of the fluorescence (i.e., the raw image). For this reason, the external device can also appropriately change, for example, the content of image processing (a control parameter) performed on the intensity distribution of the fluorescence (i.e., the raw image) according to the content of the control recognized based on the servo signal image d213 in the raw file D1.

The warm-up time photographed image d214 is an image obtained by performing two-dimensionalization on the intensity distribution of the idler light or the intensity distribution of the fluorescence acquired at the warm-up time. By recording the warm-up time photographed image d214 in the raw file D1 in this manner, the external device (for example, the information processing device 800) that has read the raw file D1 can estimate a change in the intensity of the laser light during the warm-up period. Note that the warm-up time photographed image d214 may be recorded in the raw file D1 when photographing is started at least during the warm-up time, and may not be included in other cases. In addition, details of an operation performed when photographing is performed during the warm-up time will be described later separately in "1.9. Intensity control of laser light at a warm-up time."

The tampering prevention signal d215 is a signal (data) for detecting tampering when at least a part of data in the raw file D1 is tampered with. As a specific example of the tampering prevention signal d215, a sticky bit or the like is exemplified.

The automatic tracking adjustment time subject image d216 indicates an image acquired as a result of tracking, or enlargement or reduction when, for example, such tracking, or enlargement or reduction is performed. Note that, instead of the automatic tracking adjustment time subject image d216, information that indicates the content of control of tracking, or enlargement or reduction may be recorded.

The inter-photographing synchronization signal d217 is a signal that indicates each photographing timing at which each piece of the intensity distribution of the fluorescence D11 is acquired when a plurality of pieces of the intensity distribution of the fluorescence D11 are stored in the raw file D1 as the parent raw image d11. So far, the file format of the raw file D1 according to the present embodiment has been described with reference to FIG. 19. Note that the file format of the raw file D1 shown above is merely an example, and it is needless to say that all pieces of the information may not necessarily be included therein. In addition, it is not necessary to record the image data including the idler light intensity image d212, the servo signal image d213, and the warm-up time photographed image d214 as two-dimensionalized data as long as information necessary for reproducing the image data is recorded. It is needless to say that enumeration of data equivalent to each pixel of the image data may be recorded with control data that indicates a scanning condition (i.e., information for two-dimensionalizing enumeration of the data).

1.7. Details of a Correction Process

Figure 20:
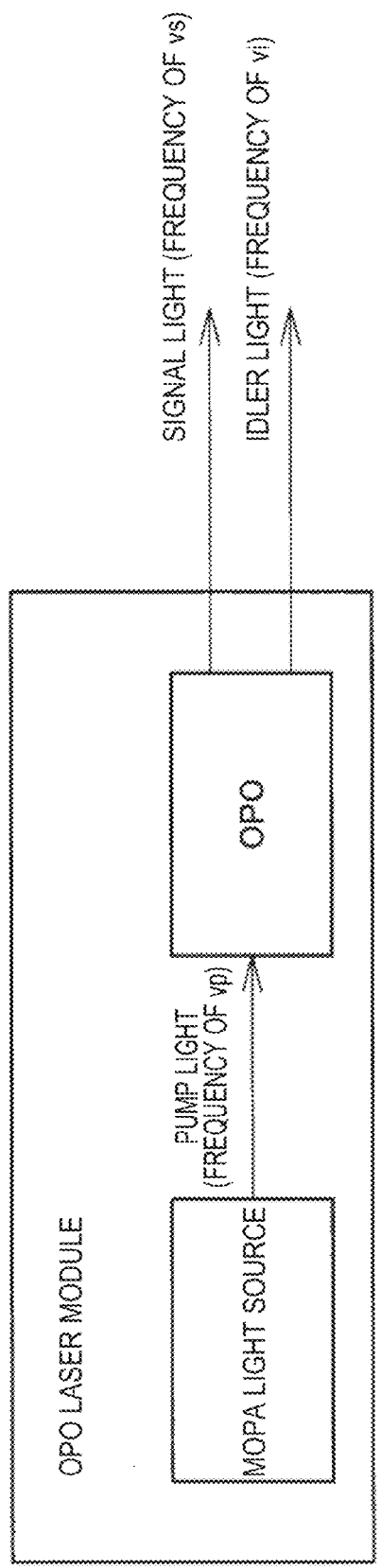
FIG. 20 is an illustrative diagram for describing the principle of correction of intensity distribution.
Figure 21:
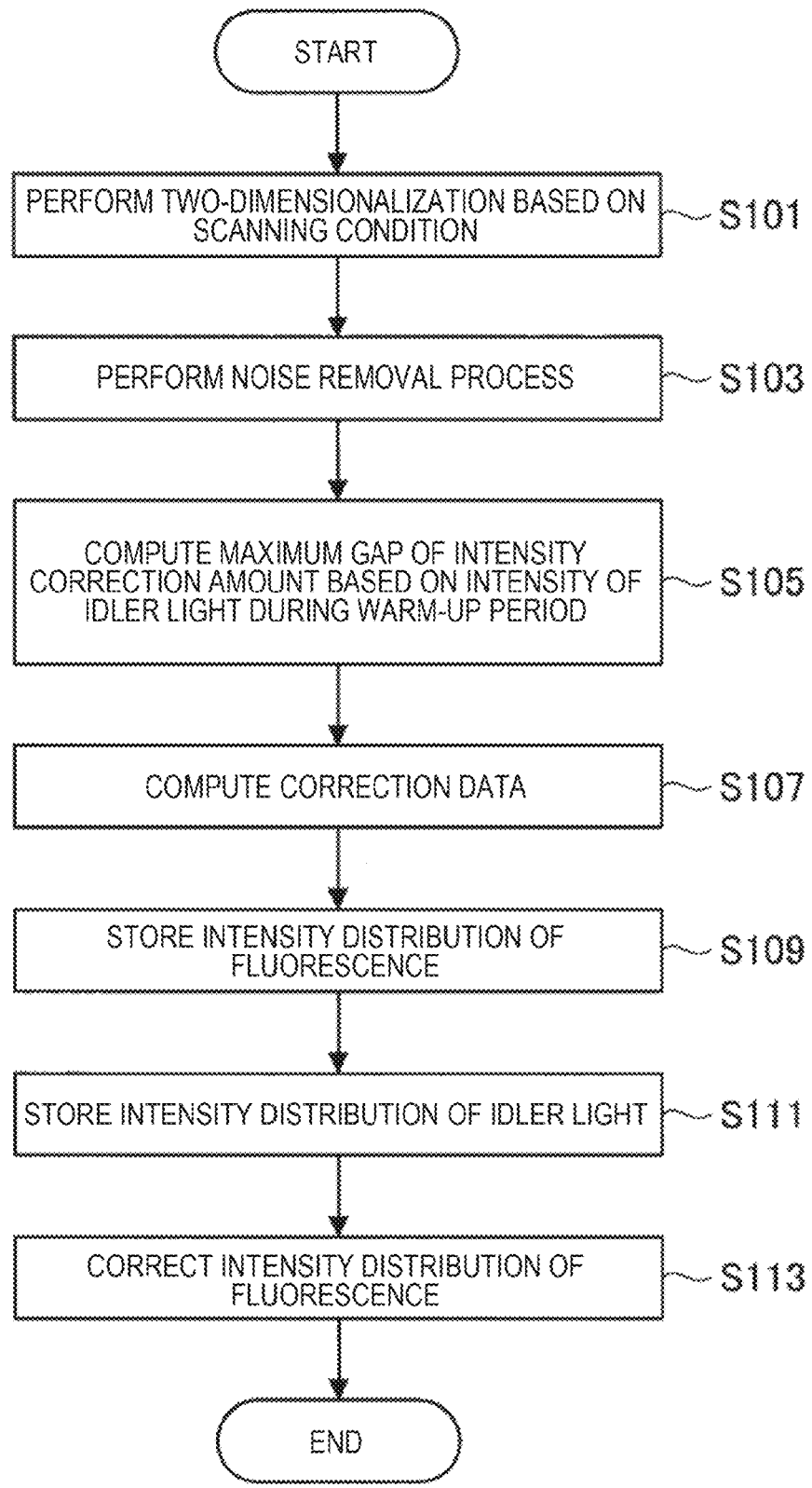
FIG. 21 is a flowchart for describing the flow of a process relating to correction of intensity distribution.

Next, operations relating to the generation of correction data based on the intensity distribution of the idler light and the correction of the intensity distribution of the fluorescence based on the correction data performed by the control unit 6 according to the present embodiment will be described in detail with reference to FIGS. 20 and 21.

<<1.7.1. Principle of Correction>>

First, the principle of the correction of the intensity distribution of the fluorescence in the image acquisition device 1 according to the present embodiment will be described with reference to FIG. 20. FIG. 20 is an illustrative diagram for describing the principle of the correction of the intensity distribution. As shown in FIG. 20, in the OPO laser module constituting the light source 2, a frequency of pump light output from the MOPA light source (with a fixed wavelength) is set to νp, a frequency of signal light to νs, and a frequency of idler light to νi.

Here, energy E per photon of light having a frequency ν is expressed by formula 1 shown below when a Planck multiplier is set to h, a speed of light to c, and a wavelength of light to λ.

$$E = h*c/\lambda = h\nu \quad \text{Formula 1}$$

Here, when a temporal change in the number of photons caused by a change in the intensity of a laser is set to n(t), the frequency of the pump light νp, the frequency of the signal light νs, and the frequency of the idler light νi satisfy the condition expressed by formula 2 below.

$$h*\nu s*n(t) = h*\nu p*n(t) - h*\nu i*n(t) \quad \text{Formula 2}$$

At this time, when excitation by signal light having energy of h*νs*n(t) occurs, a spatial fluorescence intensity PMTin(x, y, z) of fluorescence generated at the coordinates (x, y, z) on the sample S is shown in formula 3 below.

$$PMTin(x,y,z) = h*\nu s*n(t)*S(c/\nu s)*Q(x,y,z) \quad \text{Formula 3}$$

Note that S(c/νs) in formula 3 shown above indicates an absorption light emission efficiency, and Q(x, y, z) indicates spatial fluorescence concentration distribution of an observation target (i.e., the sample S).

As shown in formula 3, the temporal change in the number of photons n(t) accompanied by a change in the intensity of laser light generally remains in the spatial fluorescence intensity PMTin(x, y, z).

With respect to the above, the control unit 6 according to the present embodiment estimates the temporal change in the number of photons n(t) accompanied by the change in the intensity of laser light based on the intensity distribution of the idler light detected by the PD 54.

Specifically, since an intensity PDin(x, y, z) of idler light when it scans the coordinates (x, y, z) on the sample S changes as that of signal light according to the change in the intensity of pump light, it is expressed by formula 4 shown below.

$$PDin(x,y,z) = h*\nu i*n(t) \quad \text{Formula 4}$$

The control unit 6 computes the temporal change n(t) based on formula 4 shown above, and thereby corrects the spatial fluorescence intensity PMTin(x, y, z) shown in formula 3 based on the computed temporal change n(t). Note that when a spatial fluorescence intensity after correction is set to PMTin'(x, y, z), PMTin'(x, y, z) shown in formula 5 below expresses the spatial fluorescence intensity.

$$PMTin'(x, y, z) = PMTin(x, y, z) * (h*\nu i)/PDin(x, y, z) \quad \text{Formula 5}$$
$$= h*\nu s*S(c/\nu s)*Q(x, y, z)$$

Note that, in formula 5 shown above, (h*νi)/PDin(x, y, z) corresponds to correction data. In other words, the intensity correction distribution decision unit 623 computes the correction data based on the intensity PDin(x, y, z) of each set of coordinates (x, y, z) indicated by the acquired intensity distribution of the idler light.

<<1.7.2. Flow of an Operation Relating to Correction>>

Next, the flow of the operation relating to the generation of the correction data based on the intensity distribution of the idler light and the correction of the intensity distribution of the fluorescence based on the correction data will be described with reference to FIG. 21. FIG. 21 is a flowchart for describing the flow of a process relating to the correction of the intensity distribution. Note that description will be provided herein focusing on a process at the time of observation of the sample S for which warm-up has been finished and the intensity distribution of the idler light is assumed to be acquired in advance during the warm-up period as a pre-stage of the observation of the sample S.

(Step S101)

The two-dimensionalization processing unit 621 of the distribution information generation unit 62 sequentially acquires data indicating the intensities of the idler light detected (measured) by the PD 54 from the PD 54 at a sampling rate set in advance. In addition, the two-dimensionalization processing unit 621 sequentially acquires control information indicating control content of the galvano mirror 51 from the system control unit 61. The two-dimensionalization processing unit 621 performs two-dimensionalization on the data indicating the intensities of the idler data sequentially acquired from the PD 54 in series based on the control information acquired from the system control unit 61, and thereby generates the intensity distribution of the detected idler light. Note that the two-dimensionalization processing unit 621 at that time may discard an unnecessary portion in the intensity distribution of the idler light and set only a valid portion as the intensity distribution of the idler light. The two-dimensionalization processing unit 621 outputs the generated intensity distribution of the idler light to the intensity correction distribution decision unit 623 and the intensity control amount decision unit 611.

In addition, the two-dimensionalization processing unit 625 of the distribution information generation unit 62 sequentially acquires data indicating intensities of fluorescence detected (measured) by the PMT 53 from the PMT 53 at a sampling rate set in advance. In addition, the two-dimensionalization processing unit 625 sequentially acquires control information indicating the control content of the galvano mirror 51 from the system control unit 61. The two-dimensionalization processing unit 625 performs two-dimensionalization on the data indicating the intensities of the fluorescence sequentially acquired from the PMT 53 in series based on the control information acquired from the system control unit 61, and thereby generates the intensity distribution of the detected fluorescence. Note that the two-dimensionalization processing unit 625 at that time may discard an unnecessary portion of the intensity distribution of the fluorescence and set only a valid portion as the intensity distribution of the fluorescence. The two-dimensionalization processing unit 625 outputs the generated intensity distribution of the fluorescence to the correction processing unit 63 and the raw image generation unit 65.

(Step S103)

Note that the distribution information generation unit 62 may perform a noise removal process on each of the intensity distribution of the idler light and the intensity distribution of the fluorescence which are generated by the two-dimensionalization processing unit 621 and the two-dimensionalization processing unit 625. Implementation of the noise removal processing on each of the intensity distribution of the idler light and the intensity distribution of the fluorescence will be described separately as a "fourth embodiment."

(Step S105)

The intensity correction distribution decision unit 623 acquires the maximum value and the mean of the intensities of the idler light based on the intensity distribution of the idler light during the warm-up period acquired in advance, and then computes a maximum gap of correction amounts based on the maximum value and the mean. The intensity correction distribution decision unit 623 informs the intensity control amount decision unit 611 of the computed maximum gap of the correction amounts.

Accordingly, the intensity control amount decision unit 611 can estimate a temporal change in the number of photons caused by a change in the intensity of laser light emitted from the light source 2, and decide a maximum gap (margin) of a control amount of the intensity of the laser light (pump light). Note that details of the intensity control of the laser light (pump light) will be described later separately in "1.8. Details of intensity control of laser light."

(Step S107)

In addition, the intensity correction distribution decision unit 623 generates the correction data for correcting the intensity distribution of the fluorescence based on the intensity distribution of the idler light acquired from the two-dimensionalization processing unit 621 during observation of the sample S. Specifically, the intensity correction distribution decision unit 623 generates the correction data based on $(h*vi)/PDin(x, y, z)$ when an intensity of the idler light on the coordinates $(x, y, z)$ on the sample S is set to $PDin(x, y, z)$. Note that h indicates a Planck constant and vi indicates a frequency of the idler light. The intensity correction distribution decision unit 623 outputs the intensity distribution of the idler light to the raw image generation unit 65 and outputs the correction data generated based on the intensity distribution of the idler light to the correction processing unit 63.

(Step S109)

The raw image generation unit 65 generates a raw file by forming the intensity distribution of the fluorescence which has been acquired from the two-dimensionalization processing unit 625 being used in a predetermined file format as image data (a raw image). At this time, the raw image generation unit 65 may generate a raw file using a series of a plurality of pieces of the intensity distribution of the fluorescence which are acquired in the Z direction (depth direction) as image data.

(Step S111)

In addition, the raw image generation unit 65 associates the generated raw file with the intensity distribution of the idler light acquired from the intensity correction distribution decision unit 623. Note that, when a series of the plurality of pieces of the intensity distribution of the fluorescence acquired in the Z direction (depth direction) are recorded as image data in the raw file, the raw image generation unit 65 also associates the raw file with the intensity distribution of the idler light corresponding to each of the series of the intensity distribution of the fluorescence.

As described above, by associating the raw file with the intensity distribution of the idler light, an external device (for example, the information processing device 800) which has read the raw file D1 can correct noise accompanied by the change in the intensity of the laser light which has appeared in the intensity distribution of the fluorescence.

The raw image generation unit 65 outputs the generated raw file to, for example, the communication control unit 68. In addition, the raw image generation unit 65 may cause the generated raw file to be stored in the storage unit 66.

(Step S113)

The correction processing unit 63 acquires the intensity distribution of the fluorescence from the two-dimensionalization processing unit 625. In addition, the correction processing unit 63 acquires the correction data generated based on the intensity distribution of the idler light from the intensity correction distribution decision unit 623. The correction processing unit 63 corrects the intensity distribution of the fluorescence with the correction data based on formula 5 described above.

With this configuration, the image acquisition device 1 according to the present embodiment can correct noise appearing in the intensity distribution of the fluorescence based on the change in the intensity of the signal light with the correction data generated based on the intensity distribution of the idler light.

1.8. Details of Intensity Control of Laser Light

<<1.8.1. Principle of Intensity Control>>

Figure 22:
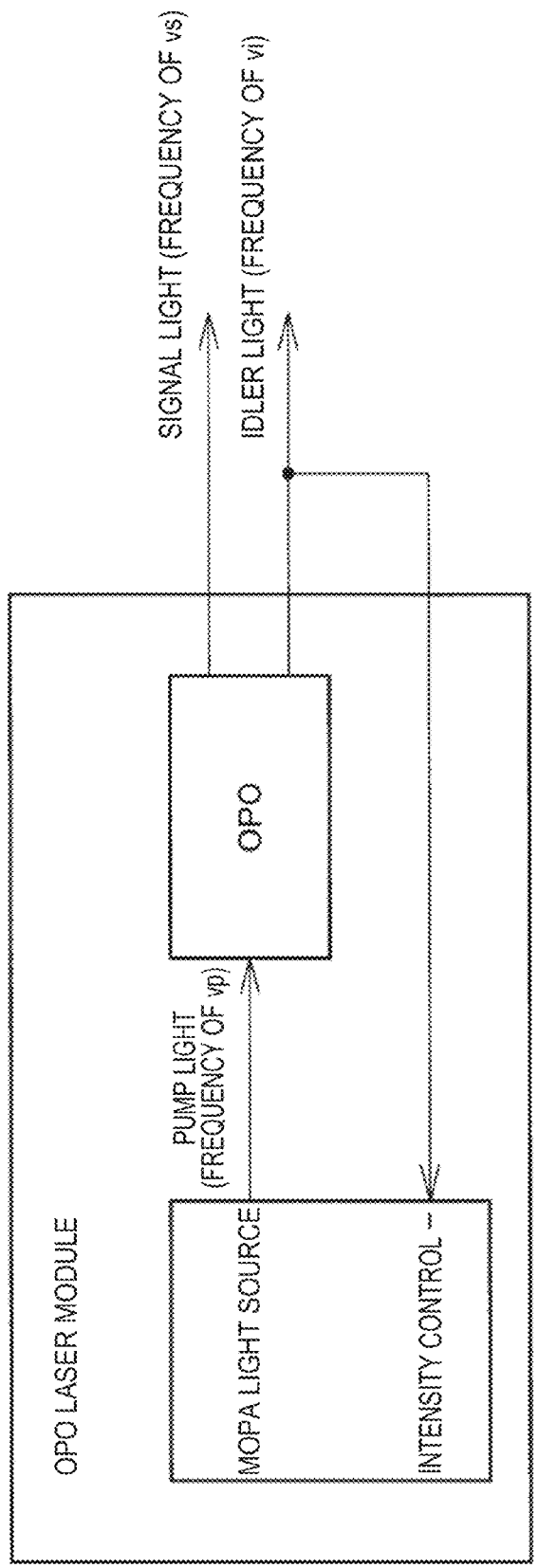
FIG. 22 is an illustrative diagram for describing the principle of intensity control of emitted light from a light source.
Figure 23:
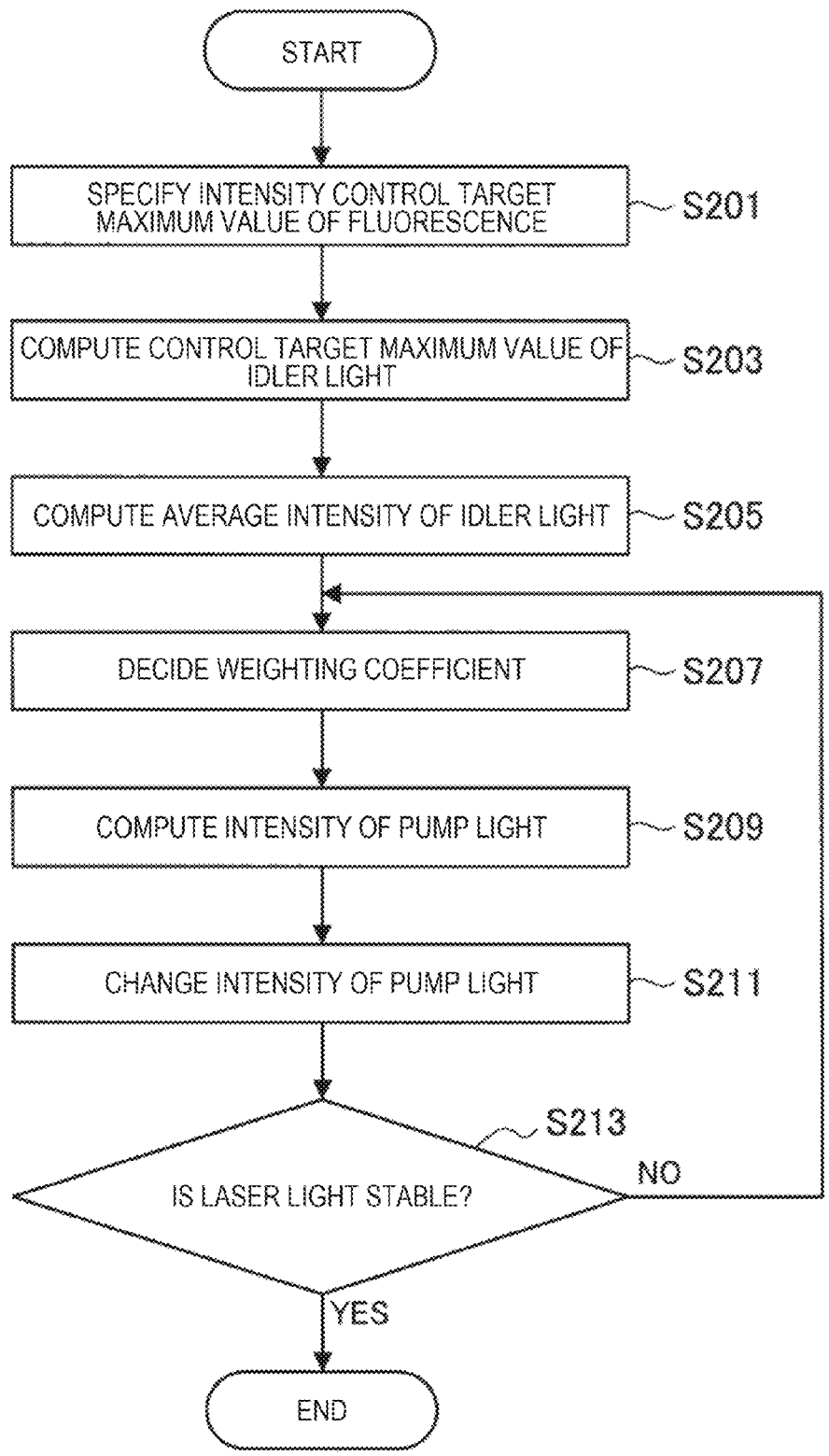
FIG. 23 is a flowchart for describing the flow of a process relating to intensity control of emitted light from the light source.

Next, details of a process relating to control of the intensity of laser light (pump light) output from the light source 2 by the control unit 6 according to the present embodiment will be described with reference to FIGS. 22 and 23.

First, the principle of the intensity control of laser light in the image acquisition device 1 according to the present embodiment will be described with reference to FIG. 22. FIG. 22 is an illustrative diagram for describing the principle of the intensity control of emitted light from the light source 2. As shown in FIG. 22, in the OPO laser module constituting the light source 2, a frequency of pump light output from the MOPA light source (with a fixed wavelength) is set to $vp$, a frequency of signal light to $vs$, and a frequency of idler light to $vi$.

For example, in the configuration in which the light source 2w is provided outside the image acquisition device 1w as in the image acquisition device 1w according to the comparative example described above, there are many cases in which fine control over the light source 2w is difficult to perform. In such a case, for example, the spatial fluorescence intensity PMTin (x, y, z) is designed to be a maximum spatial fluorescence intensity PMTin_max(x, y, z) expressed in formula 6 shown below by anticipating the temporal change in the number of photons n(t) accompanied by a change in the intensity of the output laser light.

$$PMTin\_max(x,y,z) h^* vs^* n\_max(t)^* S(c/vs)^* Q\_max(x,y,z) \quad \text{Formula 6}$$

Note that, in formula 6 shown in above, n_max(t) indicates the maximum value of the temporal change n(t) in the number of photons, and Q_max(x, y, z) indicates the maximum value of spatial fluorescence concentration distribution of an observation target (i.e., the sample S).

In other words, when fine control over the light source 2w is difficult to perform as in the image acquisition device 1w according to the comparative example, the designing is performed by anticipating the maximum value of the temporal change n(t), and thus it is difficult to use the entire dynamic range of the spatial fluorescence concentration distribution Q(x, y, z).

With respect to that, the control unit 6 according to the present embodiment monitors the change in the intensity of the laser light based on the intensity distribution of the idler light detected by the PD 54 and accordingly controls the intensity of the laser light following the change in the intensity of the laser light.

Specifically, with respect to the change in the intensity of the laser light, when a sufficiently large but mild change amount in a photographing time is set to nl(t) and a change in the photographing time is set to nh(t), the control unit 6 separates to establish a relation of n(t)=nl(t)+nh(t). For this reason, the control unit 6 applies intensity control that has latency tl that is sufficiently short with respect to the photographing time by applying negative feedback in proportion to the intensity of idler light to nl(t). The spatial fluorescence intensity PMTin(x, y, z) at that time is expressed using formula 7 shown below.

$$PMTin(x, y, z) = h * vs * n(t)/nl(t + tl) * \quad \text{Formula 7}$$
$$S(c/vs) * Q(x, y, z)$$
$$= h * vs * (nl(t) + nh(t))/nl(t + tl) *$$
$$S(c/vs) * Q(x, y, z)$$

In formula 7 shown above, when tl is sufficiently short with respect to a change of nl, formula 7 described above can approximate formula 8 shown below.

$$PMTin(x,y,z) \approx h^* vs^* (1+nh(t)/nl(t))^* S(c/vs)^* Q(x,y,z) \quad \text{Formula 8}$$

In addition, when the correction process described above is also used, formula 8 shown above can approximate formula 9 shown below since formula 8 is regarded as satisfying nh<<nl.

$$PMTin(x,y,z) \approx h^* vs^* S(c/vs)^* Q(x,y,z) \quad \text{Formula 9}$$

In other words, since the spatial fluorescence intensity PMTin(x, y, z) is expressed by formula 10 shown below, it is not necessary to consider the temporal change in the number of photons n(t) accompanied by a change in the intensity of laser light, and substantially the entire dynamic range can be used.

$$PMTin\_max(x,y,z)=h^* vs^* S(c/vs)^* Q\_max(x,y,z) \quad \text{Formula 10}$$

<<1.8.2. Flow of an Operation Relating to Intensity Control>>

Next, the flow of an operation relating to the intensity control of the laser light (pump light) output from the light source 2 will be described with reference to FIG. 23. FIG. 23 is a flowchart for describing the flow of the process relating to the intensity control of emitted light from the light source.

(Step S201)

First, an individual difference of a laser light source (for example, the semiconductor laser 222 of the mode-locked laser unit 220) used as the light source 2 is adjusted before the start of measurement to be in a reference state decided in advance based on a control parameter of the laser light source. Note that the adjustment is based on the individual difference of the laser light source and is different from adjustment of an intensity of laser light accompanied by thermal fluctuation.

Next, the intensity control amount decision unit 611 of the system control unit 61 acquires a maximum gap of correction amounts based on the intensity distribution of the idler light during the warm-up period (i.e., the maximum value/mean of the intensity of the idler light during the warm-up period) from the intensity correction distribution decision unit 623 of the distribution information generation unit 62. The intensity control amount decision unit 611 decides a maximum value n_max of an intensity control target of the laser light (pump light) based on the acquired maximum gap of the correction amounts. As a specific example, when the acquired maximum gap of the correction amounts is 2, the intensity control amount decision unit 611 decides the maximum value n_max of the intensity control target so as to use the range of the reciprocal of the maximum gap of the correction amounts, i.e., ½ of the dynamic range of the intensity of the laser light (pump light).

(Step S203)

The intensity control amount decision unit 611 computes a control target maximum value PDin_max of the intensity of the idler light based on the decided maximum value n_max of the intensity control target using formula 11 shown below. Note that, in formula 11 shown below, h indicates a Planck constant and vi indicates a frequency of the idler light.

$$PDin\_max=h^* vi^* n\_max \quad \text{Formula 11}$$

(Step S205)

In addition, the intensity control amount decision unit 611 computes the average PDin_ave of the intensity of the idler light based on the intensity distribution for one photographing time acquired recently (for example, the previous photographing time) of the intensity distribution of the idler light from the two-dimensionalization processing unit 621 out of the distribution information generation unit 62.

(Step S207)

Next, the intensity control amount decision unit 611 evaluates stability of the laser light using pattern matching over a plurality of pieces (for example, two photographing times) of the intensity distribution of the idler light acquired recently, and decides a weighting coefficient W in the range of 0<W≤1. Note that W=1 corresponds to a case in which laser light is stable, and when the coefficient W is lower, the laser light is in a more unstable state.

As a specific example, the intensity control amount decision unit 611 compares a plurality of pieces of the intensity distribution of the idler light to each other using pattern matching, then makes the differences thereof into numerical values, and compares the differences to a predetermined threshold value, thereby evaluating stability of the laser light. In this case, when the computed difference is equal to or smaller than the threshold value, the intensity control amount decision unit 611 determines the laser light to be stable and then sets W=1. In addition, when the computed difference exceeds the threshold value, the intensity control amount decision unit 611 determines the laser light to be in an unstable state, and sets the coefficient W to be a value decided in advance in the range of 0<W<1.

In addition, as another example, the intensity control amount decision unit 611 may dynamically decide the coefficient W in the range of 0<W≤1 based on the differences computed according to the comparison of the pieces of the intensity distribution of the idler light. Specifically, the intensity control amount decision unit 611 may set W to be a value closer to 0 when the computed differences are great (in other words, in an unstable case), and may set W to be a value closer to 1 when the computed differences are small (in other words, in a comparatively stable case).

(Step S209)

After the coefficient W is decided, the intensity control amount decision unit 611 computes the intensity of the laser light emitted from the light source 2 after control based on a conditional formula of intensity after control=intensity before control*(PDin_max+1)/(PDin_ave+1)*W.

(Step S211)

The system control unit 61 controls the light source 2 so that the intensity of the laser light (pump light) emitted from the light source 2 based on the intensity after control computed by the intensity control amount decision unit 611 is controlled. At this time, it is desirable for the system control unit 61 to perform feedback control so that the intensity of the laser light is controlled in units of photographing times (in other words, within photographing for one piece of the intensity distribution of the fluorescence).

(Step S213)

As the system control unit 61 controls the intensity of the laser light, the intensity control amount decision unit 611 determines whether or not the laser light is stable based on the intensity distribution of the idler light emitted from the light source 2 after the intensity of the laser light (pump light) is controlled.

As described above, the system control unit 61 gradually determines whether or not the laser light is stable, then decides the weighting coefficient W based on the determination result, and executes control of the intensity of the laser light (pump light) emitted from the light source 2.

Note that the system control unit 61 may continuously execute the series of operations described above during the period in which the light source 2 emits the laser light, or may periodically (intermittently) execute it at predetermined timings.

When the series of operations described above is periodically executed at each predetermined timing, it is better for the system control unit 61 to determine whether or not the series of operations is to be stopped in Step S213. To be specific, the system control unit 61 repeats the series of operations relating to Steps S207 to S211 (in other words, monitoring of the laser light and the feedback process based on the monitoring result) until the laser light becomes stable (No in Step S213). Then, when the laser light becomes stable (Yes in Step S213), the system control unit 61 may stop the series of operations relating to the control of the intensity of the laser light (pump light).

With this configuration, the image acquisition device 1 according to the present embodiment can stably operate the light source 2 by controlling the intensity of the laser light emitted from the light source 2 even when an operation of the light source 2 becomes unstable due to heating from mounted equipment (for example, the measurement unit 3 or the control unit 6).

1.9. Intensity Control of Laser Light at a Warm-Up Time

Next, intensity control of laser light at a warm-up time will be described. The intensity of laser light output from a laser module mostly depends on temperature as described above. For this reason, when a laser module is used as the light source 2, it is used after performing warm-up in most cases in order to stabilize the intensity of output laser light.

On the other hand, a long period of time is necessary to warm up the laser module in most cases, and there are cases in which the time taken for warm-up shortens a work time relating to observation of the sample S. Thus, the image acquisition device 1 according to the present embodiment enables observation of the sample S by controlling the intensity of laser light to stabilize the laser light even in a state in which the intensity of the laser light is unstable such as during warm-up.

Figure 24:
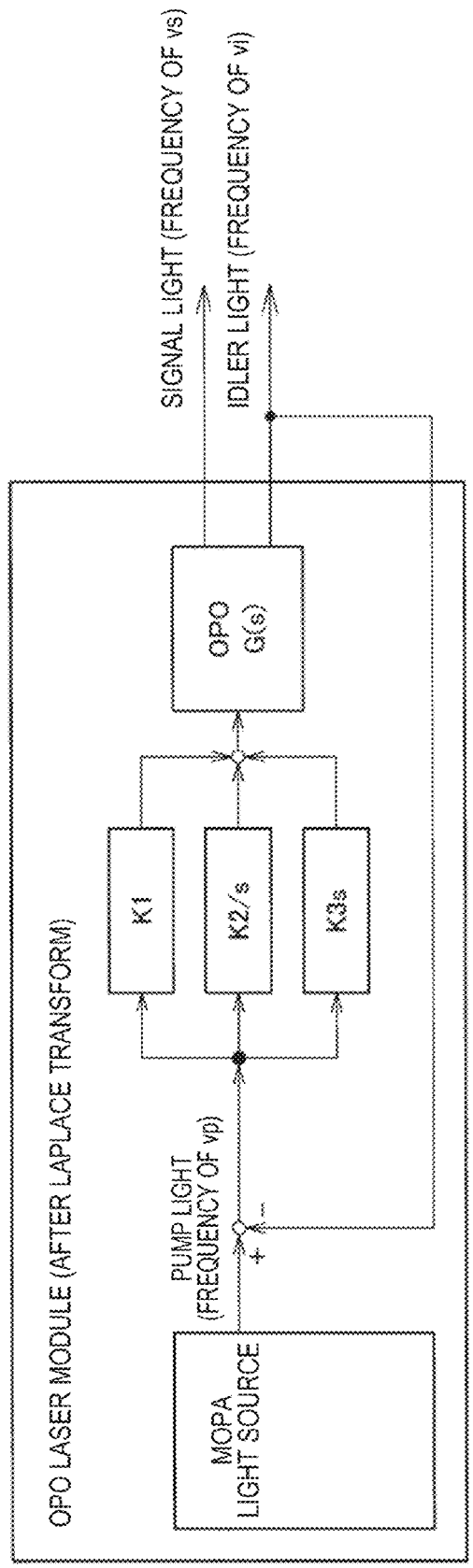
FIG. 24 is an illustrative diagram for describing the principle of intensity control of light emitted from the light source upon warm-up.

Hereinbelow, an example of intensity control of laser light at the time of warm-up of the image acquisition device 1 according to the present embodiment will be described with reference to FIG. 24. FIG. 24 is an illustrative diagram for describing the principle of intensity control of light emitted from the light source 2 at the time of warm-up. The example shown in FIG. 24 is a drawing showing that feedback control at the time of warm-up is transformed into a time response through a Laplace transform by the control unit 6 according to the present embodiment.

In the configuration described above based on FIG. 22, feedback control based on a so-called proportional component K1 and integral component K2/s, i.e., PI control, is used. When, however, the intensity of laser light is unstable as in a warm-up period, there are cases in which readiness is lacking only with the feedback control (i.e., PI control) based on the proportional component K1 and integral component K2/s.

Particularly, during the warm-up period, the latency tl is not regarded as being sufficiently short with respect to a change amount nl(t) that is sufficiently large but mild in a photographing time in the conditional formula of the spatial fluorescence intensity PMTin(x, y, z) shown as formula 7 described above. For this reason, there is a case in which a change amount having periodicity is apparent in, for example, a change in the intensity of laser light emitted from the light source 2.

Thus, the image acquisition device 1 according to the present embodiment sets the feedback control to be PID control by adding control based on a differential component K3s thereto and thereby improves readiness.

Specifically, the control unit 6 of the image acquisition device 1 calculates and accumulates transfer functions G(s) of the wavelength conversion module (OPO) 250 of the warm-up period and then computes the differential component K3s through predicting calculation based on the accumulated transfer functions G(s). Note that the control unit 6 may calculate an input to the wavelength conversion module (OPO) 250 that is based on, for example, control information for controlling the intensity of the laser light emitted from the light source 2 and thereby compute the transfer functions G(s) having the intensity of the detected idler light as an output.

Then, the image acquisition device 1 controls the intensity of the laser light emitted from the light source 2 based on the computed differential component K3s, thereby suppressing the amount of the change with periodicity from appearing.

As a specific example, the image acquisition device 1 may predict periodicity of the change in the intensity of the laser light based on the accumulated transfer functions G(s) of the OPO, and apply feedback control having a reverse phase to the predicted periodicity, thereby suppressing a change with periodicity.

With this configuration, the image acquisition device 1 according to the present embodiment can improve readiness relating to the intensity control of the laser light emitted from the light source 2 even in the state in which the intensity of the laser light emitted from the light source 2 is unstable as in the warm-up period. For this reason, according to the image acquisition device 1, observation of the sample S can be started even in a state in which, for example, the warm-up period has not ended (in which the intensity of the emitted laser light is unstable).

Note that, when observation is started before the end of the warm-up period, there are cases in which an amount of control based on the differential component K3s is greater than an amount of a periodic change of the emitted laser light and influence of control using the differential component K3s remains as noise. For this reason, when observation is started before the end of the warm-up period, the image acquisition device 1 may acquire intensity distribution of fluorescence and intensity distribution of idler light in advance using a known sample such as a fluorescent bead before the observation is started. In this case, the image acquisition device 1 may associate the intensity distribution of fluorescence and the intensity distribution of idler light which have already been acquired before observation with a raw file created based on an observation result of the sample S as a photographed image of the warm-up time (refer to FIG. 19).

With this configuration, an external device (for example, the information processing device 800) that has acquired the raw file can infer a change in the intensity of the laser light based on the photographed image of the warm-up time associated with the raw file. For this reason, even when the influence of control using the differential component K3s remains as noise in the observation result (i.e., the intensity distribution of the fluorescence) of the raw file, the external device can correct the noise by supposing the change in the intensity of the laser light.

As described above, according to the image acquisition device 1 of the present embodiment, even in the state in which the warm-up period has not ended (in which the intensity of the emitted laser light is unstable), observation of the sample S can be started. For this reason, according to the image acquisition device 1 of the present embodiment, since a period in which observation is not possible due to warm-up is shortened, it is resultantly possible to shorten an observation time of the sample S.

1.10. Operation of an Information Processing Device

Figure 25:
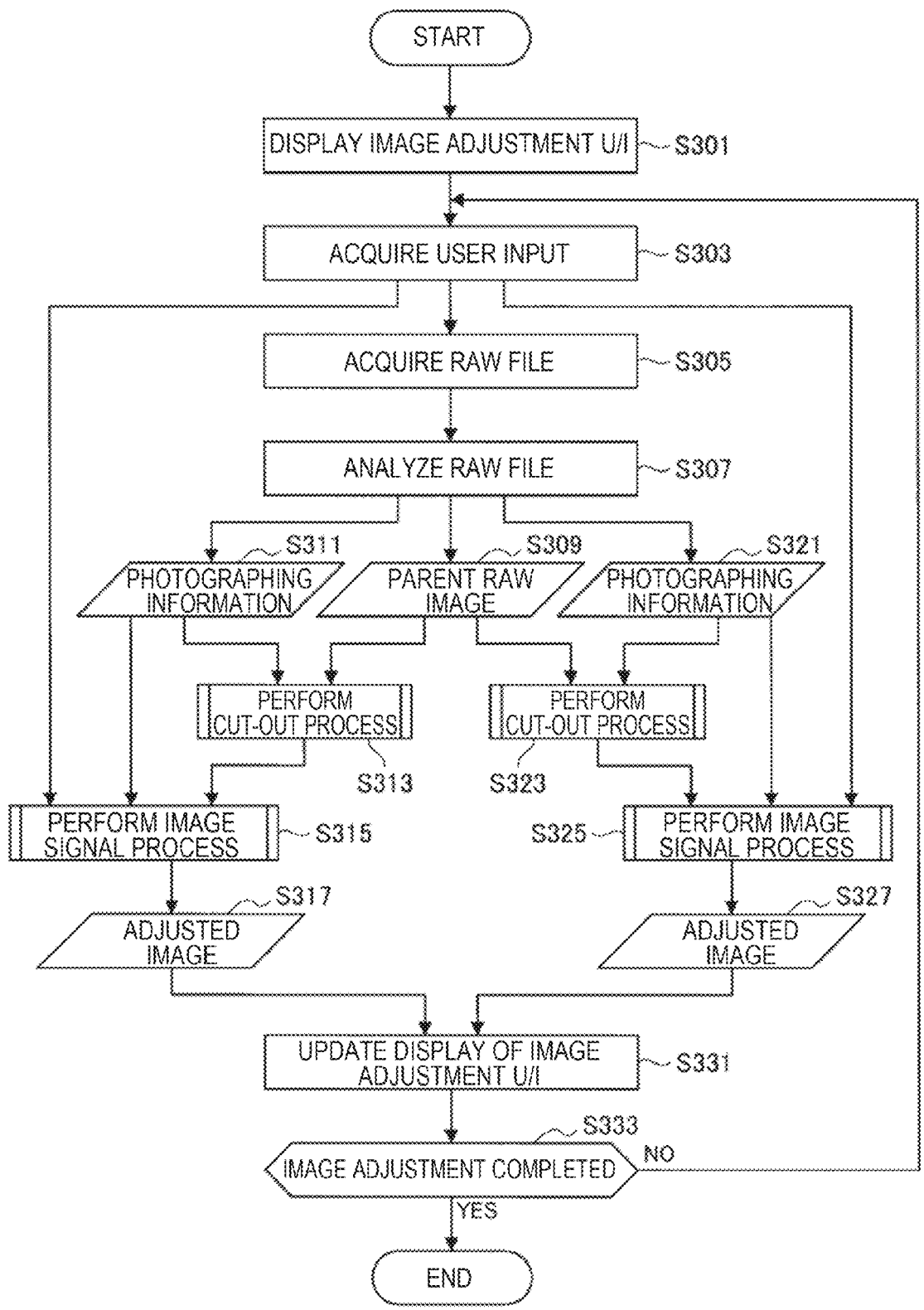
FIG. 25 is a flowchart showing the flow of a series of processes relating to image display of an information processing device according to the embodiment.
Figure 26:
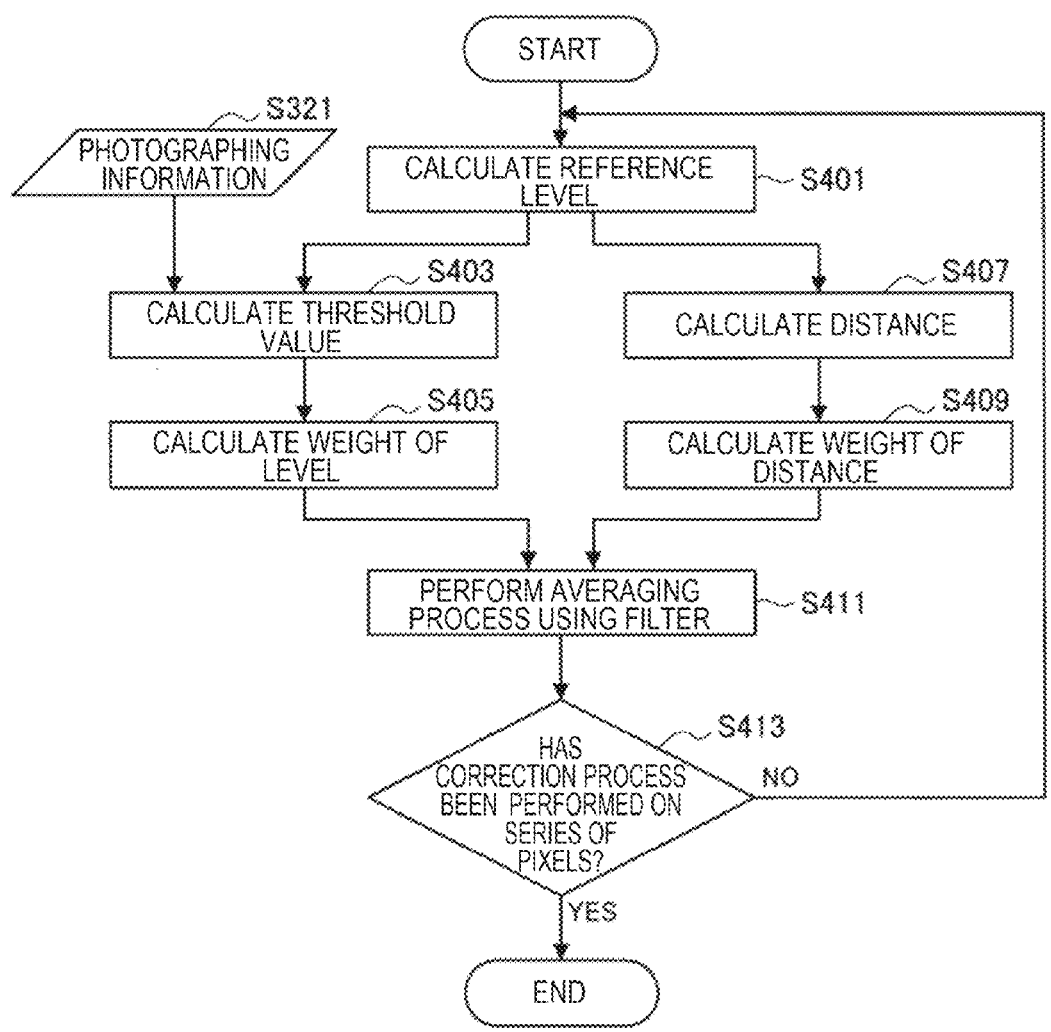
FIG. 26 is a flowchart showing an example of a process relating to noise correction of the information processing device according to the embodiment.

Next, an example of a process in which the information processing device 800 generates an image of the sample S based on the raw file D1 acquired from the image acquisition device 1 and performs image processing on the generated image and then presents the image to a user will be described with reference to FIGS. 25 and 26. FIG. 25 is a flowchart showing the flow of a series of processes relating to image display of the information processing device 800 according to the present embodiment. In addition, FIG. 26 is a flowchart showing an example of a process relating to noise correction of the information processing device 800 according to the present embodiment. First, FIG. 25 will be referred to.

(Step S301)

First, the information processing device 800 presents a U/I (which is described hereinafter as an "image adjustment U/I) for designating the raw file D1 that is a target for image correction and display, the content of image processing performed on the designated raw file D1, and a parameter of the processing to a user through, for example, a display device.

(Step S303)

In addition, the information processing device 800 specifies information designated by the user through the presented image adjustment U/I, for example, the raw file D1 to be processed, the content of the image processing, and the processing parameter based on manipulation content of the user (for example, manipulation content using a manipulation device).

(Step S305)

The information processing device 800 acquires the raw file D1 to be processed based on the designation of the user. Note that the raw file D1 may be acquired from the image acquisition device 1 in advance and then stored in a storage device or the like, or acquired from the image acquisition device 1 after establishing communication with the image acquisition device 1.

(Step S307) The information processing device 800 analyzes the acquired raw file D1 based on the file format of the raw file D1, and then extracts information recorded in the raw file D1. Accordingly, the information processing device 800 extracts, for example, a parent raw image S309 recorded in the raw file D1 and pieces of photographing information S311 and S321 indicating conditions at the time of photographing of the parent raw image S309. The pieces of the extracted photographing information S311 and S321 as described above include, for example, the intensity distribution of the idler light described above. Note that it is needless to say that, when the raw file D1 to be processed has already been analyzed, the information processing device 800 may not execute a process relating to analysis of the raw file D1 again.

The information processing device 800 generates an image of the sample S based on the parent raw image S309 and the pieces of the photographing information S311 and S321 which are extracted from the raw file D1, and then performs image processing on the generated image and presents the image to the user. Note that, as an example of the image processing, a process relating to noise correction is exemplified. Thus, hereinbelow, the process relating to correction of noise accompanied by a change in the intensity of laser light described above will be described as Steps S313 and S315 and another process relating to noise correction of which noise is different from that accompanied by a change in the intensity of the laser light will be described as Steps S323 and S325.

(Step S313)

First, details of the process relating to the correction of noise accompanied by a change in the intensity of the laser light will be described. In this case, the information processing device 800 first cuts out an image of an area to be processed from the extracted parent raw image S309 and sets the partial image corresponding to the cut-out area as a process target.

Note that the area to be processed may be acquired by, for example, the information processing device 800 for itself based on a user input.

In addition, as another example, the image acquisition device 1 may receive designation of an area to be observed as a user input at the time of photographing the parent raw image S309 and record control information that indicates the area in the raw file D1 as the photographing information S311. In this case, the information processing device 800 may recognize the area to be processed based on the control information recorded as the photographing information S311 from the raw file D1.

Of course, it is needless to say that the parent raw image S309 may be set as a process target without performing the cut-out process. Note that, in processes thereafter, the cut-out partial image and the parent raw image S309 itself may be described simply as the "parent raw image S309" without particular discrimination.

(Step S315)

The information processing device 800 corrects noise accompanied by a change in the intensity of the laser light appearing on the parent raw image S309 using the intensity distribution of the idler light extracted as the photographing information S311. Details of the present correction process are the same as those of the process performed by the image acquisition device 1 described above computing the correction data based on the intensity distribution of the idler light and correcting the intensity distribution of the fluorescence based on the correction data.

Note that the information processing device 800 may also be configured to be capable of adjusting the details of the correction process based on a parameter of the correction process designated as a user input. As a specific example, the information processing device 800 may be set to be capable of adjusting an amount of application of the correction process to the parent raw image S309 using the intensity distribution of the idler light based on the user input.

Thus, the information processing device 800 corrects noise accompanied by the change in the intensity of the laser light appearing on the parent raw image S309 and thereby generates an adjusted image S317.

(Step S323)

Next, another process relating to noise correction of which noise is different from that accompanied by the change in the intensity of the laser light will be described exemplifying a case in which noise correction is performed based on an $\epsilon$ filter. First, the information processing device 800 cuts out an image of an area to be processed from the extracted parent raw image S309 and sets a partial image corresponding to the cut-out image as a process target. The process is the same as that relating to Step S313 described above.

(Step S323)

Next, the information processing device 800 corrects the parent raw image S309 based on the extracted photographing information S321.

Here, details of the process relating to the correction will be described with reference to FIG. 26. FIG. 26 is a flowchart showing an example of the process relating to the noise correction of the information processing device 800 according to the present embodiment.

(Step S401)

First, the information processing device 800 specifies pixels that will be a reference of processing from the parent raw image S309 and computes a level of the pixel (pixel value) as a reference level.

(Step S403)

Next, the information processing device 800 calculates threshold values for weighting each of pixels serving as process targets. At that time, the information processing device 800 sets the threshold values for each pixel of which an intensity of idler light radically changes in comparison to those of peripheral pixels to be higher than that of other pixels using the intensity distribution of the idler light extracted as the photographing information S311.

(Step S405)

After the threshold values are computed for each of the pixels serving as process targets, the information processing device 800 performs weighting on the level for each pixel serving as a process target based on the computed reference level and the threshold values computed for each of the pixels serving as process targets.

(Step S407)

In addition, the information processing device 800 computes the distance from a pixel serving as a reference to each pixel serving as a process target.

(Step S409)

The information processing device 800 performs weighting on the distance to each pixel serving as a process target based on the distance computed for each pixel serving as a process target.

(Step S411)

The information processing device 800 performs an averaging process by applying the $\epsilon$ filter based on the weight on the level and the weight on the distance computed for each pixel serving as a process target.

(Step S413)

Thus, the information processing device 800 executes the series of operations described above while the noise correction process is being performed on the series of pixels serving as process targets (No in Step S413). Then, the information processing device 800 performs the noise correction process on the series of pixels (Yes in Step S413), thereby generating the adjusted image S327.

(Step S331)

Herein, FIG. 25 will be referred to again. When at least any one of adjusted images S317 and S327 is generated, the information processing device 800 presents the generated adjusted images in a predetermined region on the image adjustment U/I, and updates display of the image adjustment U/I. Accordingly, the user can check the generated adjusted image through the image adjustment U/I. At this time, the information processing device 800 may cause the generated adjusted image in a predetermined storage unit (for example, a storage such as a hard disk).

(Step S333)

The information processing device 800 continues the series of processes relating to adjustment of the image and presentation of the adjusted image described above until the user instructs an end of the image adjustment (No in Step S333). At this time, the information processing device 800 may further execute a process relating to adjustment of the image on the generated adjusted image based on the instruction from the user.

When the user instructs the end of the image adjustment (Yes in Step S333), the information processing device 800 terminates the series of processes relating to the image adjustment and presentation of the adjusted image described above.

Hereinabove, the example of the process relating to the noise correction of the information processing device 800 according to the present embodiment has been described with reference to FIGS. 25 and 26. By associating the raw file D1 with relevant information such as the intensity distribution of idler light as described above, even such an external device as the information processing device 800 can correct noise based on a change in the intensity of laser light like the image acquisition device 1.

1.11. Conclusion

As described so far, when signal light is set as excitation light, the image acquisition device 1 according to the present embodiment corrects the intensity distribution of fluorescence that is based on the excitation light using the intensity distribution of idler light. With this configuration, even in a situation in which the intensity of laser light changes, for example, the image acquisition device 1 according to the present embodiment can correct noise accompanied by the change in the intensity of the laser light and thereby obtain a vivid image.

In addition, the image acquisition device 1 according to the present embodiment monitors the intensity of the excitation light emitted from the light source 2 based on the intensity distribution of the idler light, and controls the intensity of the laser light (pump light) emitted from the light source 2 based on the monitoring result. With this configuration, even in a situation in which the intensity of laser light changes, for example, the image acquisition device 1 according to the present embodiment can control such that the intensity of the laser light is stable.

Since the image acquisition device 1 according to the present embodiment can have the light source 2 mounted in the same housing due to the characteristic described above, the image acquisition device 1 can be miniaturized.

In addition, in the configuration in which a light source is provided outside like the image acquisition device 1w according to the comparative example, a laser module that is used as the light source is provided by, for example, an original equipment manufacturer (OEM) or the like, the internal structure thereof is made into a black box, and thus there are many cases in which detailed control is difficult. For this reason, the image acquisition device 1w according to the comparative example is used with a low output in order to stably operate the laser module in many cases, and thus there are cases in which performance of the laser module is not sufficiently utilized.

On the other hand, the image acquisition device 1 according to the present embodiment controls the intensity of laser light and corrects noise accompanied by a change in the intensity of the laser light as shown above. For this reason, the image acquisition device 1 according to the present embodiment can obtain a vivid image even when a laser module is used with its output raised, and thus performance of the laser module can be sufficiently utilized.

2. Second Embodiment

2.1. Overview of an Image Acquisition Device

Next, an image acquisition device according to a second embodiment will be described. First, a problem of the image acquisition device according to the present embodiment will be clarified.

An image acquisition device that uses the same light source as the fluorescence microscope mostly uses a laser light source with a fixed wavelength which can emit light with an excitation wavelength decided in advance depending on, for example, a fluorochrome to be used.

However, there are cases in which a fluorescence base substance in a sample fades with elapse of time, and in such a case, an excitation wavelength changes, and thus it is necessary to change the wavelength of excitation light output from a laser light source. When such a situation is dealt with by employing a configuration of using a laser light source with a fixed wavelength, it is necessary to provide a plurality of kinds of laser light sources, which results in an increase in a size of a device, which seriously hinders user convenience, and a price of the device tends to increase.

In addition, the excitation wavelength of the fluorescence base substance in the sample changes according to a degree of fading, and thus, in a configuration in which a plurality of laser light sources with fixed wavelengths are provided, there are cases in which a user has to specify a laser light source which excites the fluorescence base substance by appropriately switching laser light sources in use, which results in deterioration of convenience. In addition, in the configuration in which a plurality of kinds of laser light sources are switched to be used, even if fluorescence from a sample in which fading has progressed can be excited, an image with high contrast is not necessarily obtained.

Therefore, the present disclosure proposes a novel and improved image acquisition device and image acquisition method which enable an image with a high contrast to be obtained using an easier method even in a situation in which an excitation wavelength of a sample changes.

Specifically, the image acquisition device according to the present embodiment uses a laser module that can change a wavelength of output laser light (excitation light) as a light source and controls the wavelength of the laser light based on intensity distribution of observed fluorescence. Accordingly, the image acquisition device according to the present embodiment can acquire an image with high contrast without requiring an observer (user) to perform a troublesome task such as, for example, controlling an operation of the light source 2 while checking observation results or switching the light source 2 itself.

Hereinbelow, with regard to the image acquisition device according to the present embodiment, a configuration of an optical system will be first described and then a functional configuration of the image acquisition device will be described. Note that the image acquisition device according to the present embodiment may be described as an "image acquisition device 1a" hereinbelow in order to be distinguished from the image acquisition device 1 according to the first embodiment.

2.2. Configuration of the Image Acquisition Device

<<2.2.1. Configuration of an Optical System>>

Figure 27:
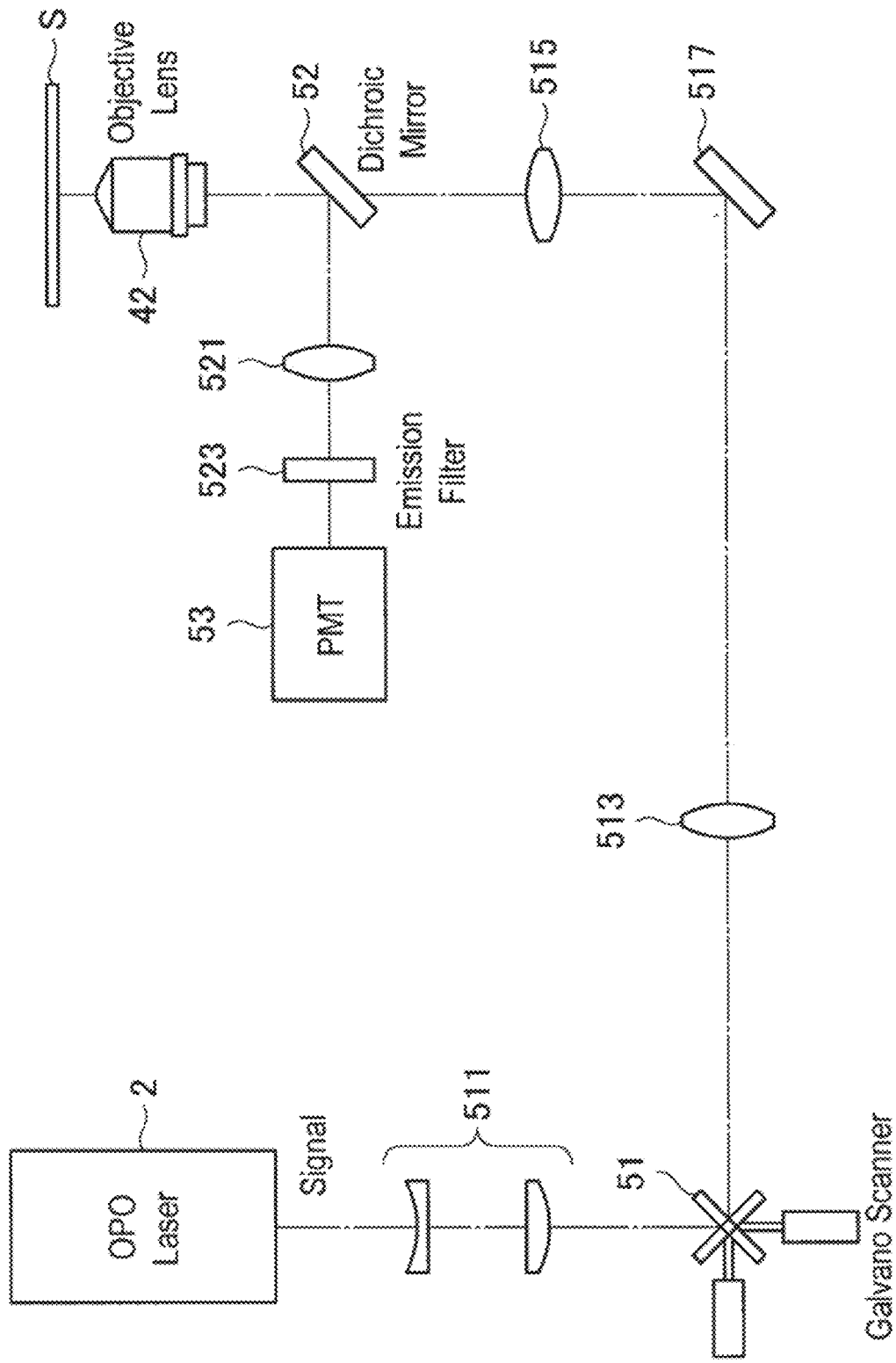
FIG. 27 is an illustrative diagram showing an example of a configuration of an optical system of an image acquisition device according to a second embodiment of the present disclosure.

First, the configuration of the optical system of the image acquisition device 1a according to the present embodiment will be described with reference to FIG. 27 particularly focusing on different parts from the configuration of the optical system (refer to FIG. 14) of the image acquisition device 1 according to the first embodiment described above. Note that description will be provided herein on the assumption that signal light is radiated toward the sample S as excitation light as in the first embodiment described above.

The image acquisition device 1a according to the present embodiment controls a wavelength of laser light (pump light) emitted from the light source 2 based on an intensity of fluorescence (colored light) detected by the PMT 53. For this reason, it is not necessary to provide the PD 54 for detecting an intensity of idler light unlike in the image acquisition device 1 according to the first embodiment described above.

Note that the configuration in which excitation light is radiated toward the sample S is the same as the optical system of the image acquisition device 1w (refer to FIG. 10) according to the comparative example described above and the optical system of the image acquisition device 1 (refer to FIG. 14) according to the first embodiment. In other words, the excitation light emitted from the light source 2 is guided to the objective lens 42 via the beam-forming lens 511, the galvano mirror 51, the lens 513, the mirror 517, the lens 515, and the dichroic mirror 52, and then collected toward the sample S by the objective lens 42.

In addition, when the sample S is irradiated with the excitation light, some molecules of the sample S are excited by the excitation light and thereby emit fluorescence, and the fluorescence forms an image on the detection plane of the PMT 53 via the objective lens 42, the dichroic mirror 52, the image-forming lens 521, and the emission filter 523. At this time, light other than colored light (natural light) that has been enlarged by the objective lens 42 is absorbed by the emission filter 523, (in other words, only the colored light is transmitted therethrough), and then an image of the colored light that has lost the natural light is formed on the PMT 53.

<<2.2.2. Functional Configuration of the Image Acquisition Device>>

Figure 28:
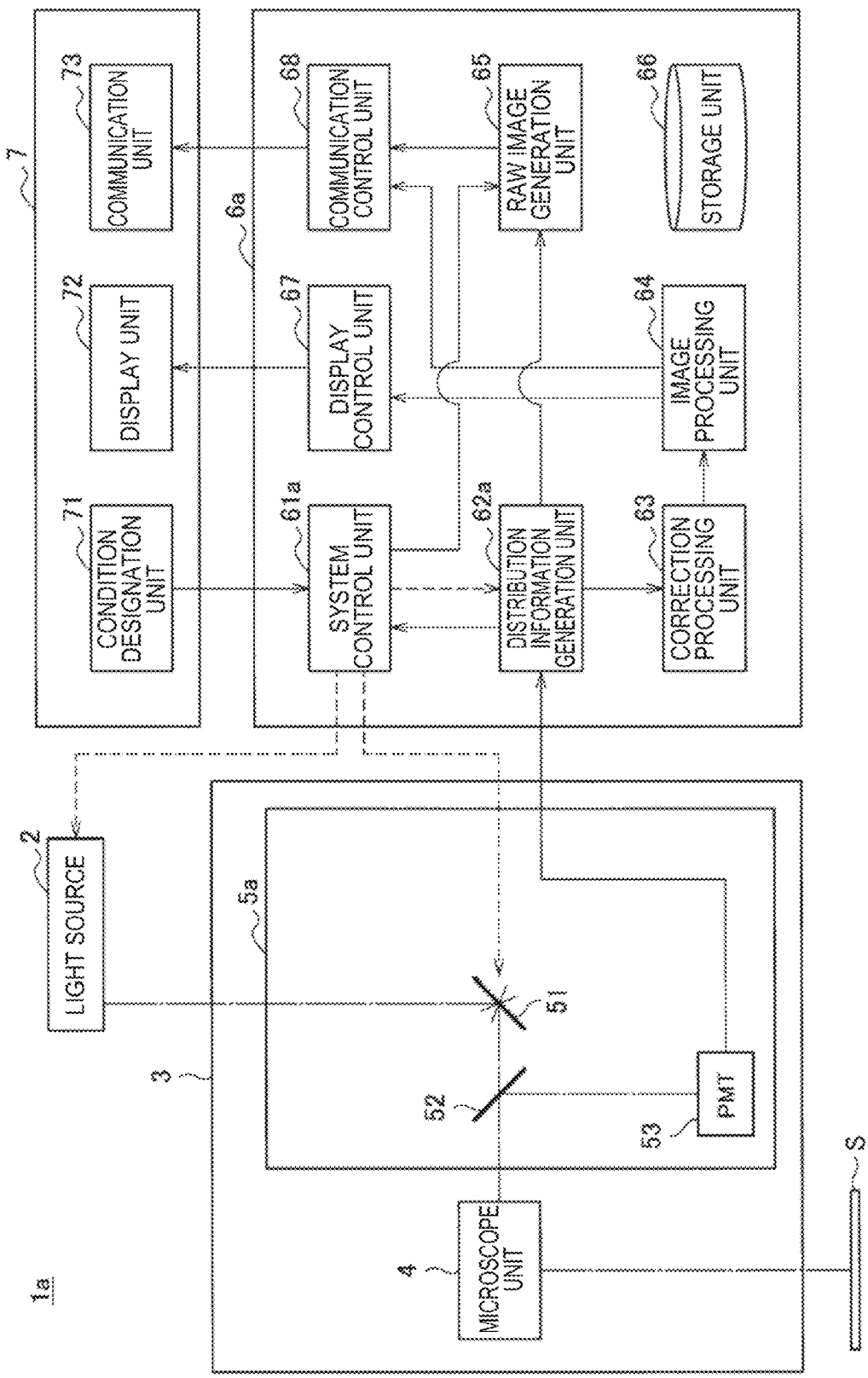
FIG. 28 is an illustrative diagram for describing an example of a functional configuration of the image acquisition device according to the embodiment.

Next, an example of the functional configuration of the image acquisition device 1a according to the present embodiment will be described with reference to FIG. 28. As shown in FIG. 28, the image acquisition device 1a according to the present embodiment includes the light source 2, the measurement unit 3, a control unit 6a, and the I/F 7. In addition, the measurement unit 3 includes the microscope unit 4 and a scanning system (detection system) 5a. Note that the configurations of the light source 2, the microscope unit 4, and the I/F 7 are the same as those of the image acquisition device 1 according to the first embodiment described above. For this reason, description will be provided hereinbelow focusing particularly on the configurations of the scanning system (detection system) 5a and the control unit 6a which are different from the image acquisition device 1 according to the first embodiment. Note that, in the example shown in FIG. 28, each constituent element of the scanning system (detection system) 5a corresponds to that to which the same reference numeral is given in the optical system shown in FIG. 27. In addition, some of the constituent elements shown in FIG. 27 are omitted in the example shown in FIG. 28.

As shown in FIG. 28, the scanning system (detection system) 5a according to the present embodiment is different from the scanning system (detection system) 5 according to the first embodiment described above (refer to FIG. 15) in that it is not necessary for the former to include the PD 54 for measuring idler light. Note that other configurations thereof are the same as the scanning system (detection system) 5 according to the first embodiment described above.

In other words, excitation light emitted from the light source 2 is radiated to the sample S via the scanning system (detection system) 5a and the microscope unit 4. In addition, fluorescence generated from the sample S due to the radiated excitation light is guided to the scanning system (detection system) 5a via the microscope unit 4 and then detected by the PMT 53 of the scanning system (detection system) 5a. The PMT 53 converts the detected fluorescence into an electric signal through photoelectric conversion at a sampling rate set in advance, and then outputs the signal to the control unit 6a as data indicating an intensity of the fluorescence.

The control unit 6a includes a system control unit 61a, a distribution information generation unit 62a, the correction processing unit 63, the image processing unit 64, the raw image generation unit 65, the storage unit 66, the display control unit 67, and the communication control unit 68. Note particularly that the control unit 6a according to the present embodiment has the system control unit 61a and the distribution information generation unit 62a with different configurations from the control unit 6 according to the first embodiment described above (refer to FIGS. 15 and 16).

Figure 29:
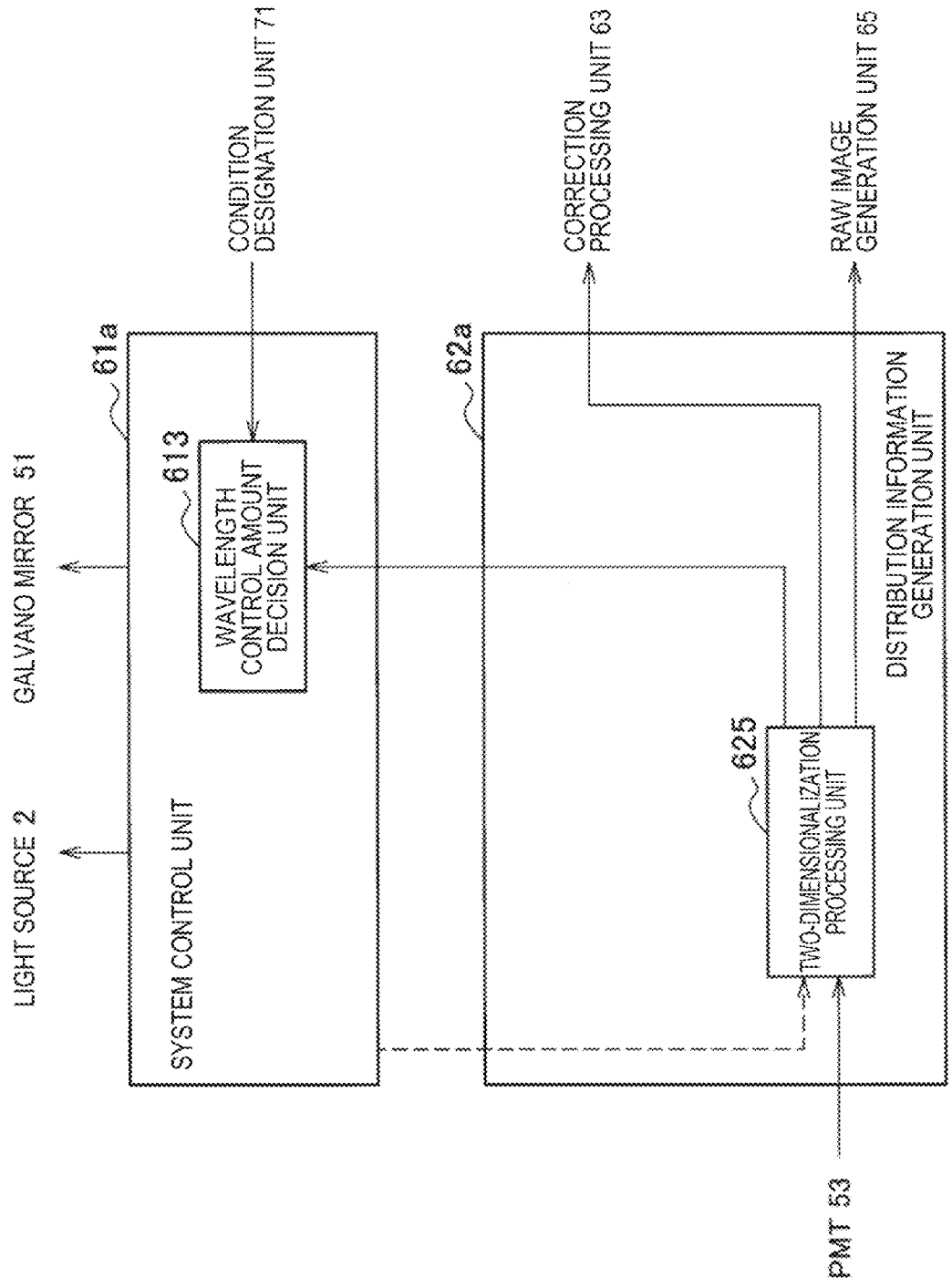
FIG. 29 is an illustrative diagram for describing a detailed functional configuration of a distribution information generation unit and a system control unit according to the embodiment.

Herein, detailed configurations of the system control unit 61a and the distribution information generation unit 62a will be described with reference to FIG. 29. As shown in FIG. 29, the distribution information generation unit 62a includes a two-dimensionalization processing unit 625. In addition, the system control unit 61a includes the wavelength control amount decision unit 613.

The two-dimensionalization processing unit 625 sequentially acquires the data that indicates the intensities of the fluorescence detected (measured) by the PMT 53 at a sampling rate set in advance from the PMT 53. In addition, the two-dimensionalization processing unit 625 sequentially acquires the control information that indicates the content of control of the galvano mirror 51 from the system control unit 61. By performing two-dimensionalization on the data indicating the intensities of the fluorescence sequentially acquired from the PMT 53 in series based on the control information acquired from the system control unit 61, the two-dimensionalization processing unit 625 generates intensity distribution of the detected fluorescence.

The two-dimensionalization processing unit 625 outputs the generated intensity distribution of the fluorescence to the wavelength control amount decision unit 613, the correction processing unit 63, and the raw image generation unit 65.

Note that the intensity distribution of the fluorescence output from the two-dimensionalization processing unit 625 undergoes a correction process such as removal of noise by the correction processing unit 63 and then is output to the image processing unit 64. The image processing unit 64 performs image processing such as a compression process on the intensity distribution that has undergone the correction process, thereby generating image data. The generated image data is output to, for example, the display control unit 67, and then displayed on the display unit 72 by the display control unit 67. Accordingly, a user can check an image of the sample S through the display unit 72.

The wavelength control amount decision unit 613 acquires the generated intensity distribution of the fluorescence from the two-dimensionalization processing unit 625, and decides a control amount of the wavelength (frequency) of the laser light (excitation light) emitted from the light source 2 so as to improve contrast of the intensity distribution of the fluorescence. When the control amount of the wavelength of the laser light is decided by the wavelength control amount decision unit 613, the system control unit 61 controls the wavelength of the laser light emitted from the light source 2 based on the control amount.

When the wavelength of the laser light emitted from the light source 2 is controlled, the two-dimensionalization processing unit 625 acquires the intensity distribution of the fluorescence that is based on the laser light after the control, and outputs the acquired intensity distribution of the fluorescence to the wavelength control amount decision unit 613. The wavelength control amount decision unit 613 evaluates the intensity distribution of the fluorescence that has been acquired again, and then computes a control amount of the wavelength of the laser light so as to improve contrast of the intensity distribution of the fluorescence.

By repeating the above operation, the system control unit 61a and the wavelength control amount decision unit 613 controls the wavelength of the laser light emitted from the light source 2 so that, for example, the contrast of the intensity distribution of the fluorescence is maximized.

Note that the wavelength control amount decision unit 613 may decide a control amount of the wavelength of the laser light by evaluating contrast targeting an area of the acquired intensity distribution of the fluorescence designated by the user as an observation target.

In that case, the display control unit 67 may display image data created based on the intensity distribution of the fluorescence and a U/I for designating an area of the image data on the display unit 72. Accordingly, the user can designate an area that is an observation target with respect to the image displayed on the display unit 72 through the condition designation unit 71.

Figure 30:
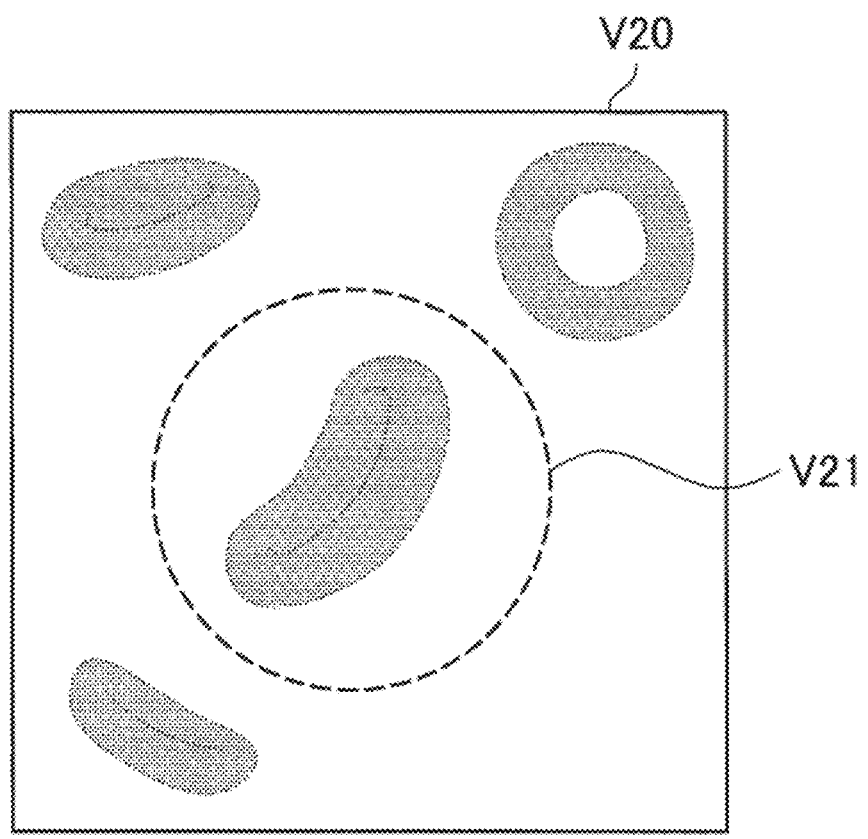
FIG. 30 is a diagram for describing an example of a designation method of an observation target.

For example, FIG. 30 is a diagram for describing an example of a designation method of an observation target. In FIG. 30, reference numeral V20 indicates an image displayed on the display unit 72, and reference numeral V21 schematically indicates an area designated as an observation target by the user. Note that the shape of the area V21 is not necessarily limited to the circular shape as shown in FIG. 30 as long as at least a partial region of the image V20 can be designated. For example, the shape of the area V21 may be a rectangular shape, or an arbitrary shape designated by the user. The wavelength control amount decision unit 613 acquires information indicating the area V21 of the image designated by the user through the condition designation unit 71 with regard to the image V20 of the sample S displayed on the display unit 72 from the condition designation unit 71. Note that a coordinate system of the image V20 corresponds to a coordinate system of the intensity distribution of the fluorescence. For this reason, the wavelength control amount decision unit 613 recognizes an area on the intensity distribution of the fluorescence which corresponds to the area V21 designated for the image V20 by the user based on the information indicating the area V21 acquired from the condition designation unit 71.

Note that, when the information indicating the area V21 designated as an observation target by the user is acquired, the wavelength control amount decision unit 613 may decide a control amount of the wavelength of the laser light so as to improve contrast targeting the area V21 on the intensity distribution of the fluorescence.

In addition, the system control unit 61a may be set to be capable of controlling (adjusting) the wavelength of the laser light based on designation from the user. As a specific example, the system control unit 61a may be set to be capable of receiving designation from the user with respect to whether or not further adjustment is necessary for an image that has been created based on the intensity distribution of the fluorescence after the wavelength control and determining whether or not the wavelength of the laser light should be further controlled based on the designation.

In that case, for example, the display control unit 67 presents the image data created based on the intensity distribution of the fluorescence after the wavelength control to the user through the display unit 72, and the system control unit 61a acquires designation of the user that indicates whether or not further adjustment is necessary from the condition designation unit 71.

When the system control unit 61a receives the designation of the user which indicates that further adjustment is necessary, the system control unit may cause the wavelength control amount decision unit 613 to compute a control amount of the wavelength of the laser light again. In addition, in that case, the system control unit 61a may control the wavelength control amount decision unit 613 so as to control a condition relating to the computation of the control amount of the wavelength of the laser light (for example, a parameter such as a threshold value relating to determination of contrast).

In addition, as another example, the system control unit 61a may be operated so that the user can directly or indirectly designate a wavelength of laser light. As a specific example, the system control unit 61a may receive designation from the user relating to adjustment of contrast (for example, heightening or lowering of contrast or designating an adjustment amount) and thereby control a wavelength of laser light based on the designated adjustment content of contrast.

The system control unit 61a can automatically control a wavelength of laser light so as to improve contrast of the intensity distribution of fluorescence as described above, and can control the wavelength of the laser light based on an instruction from the user. With this configuration, for example, the system control unit 61a can be operated so that, after the wavelength of the laser light is automatically controlled so as to maximize contrast of the intensity distribution of fluorescence, the wavelength of the laser light is finely adjusted based on the instruction from the user.

Note that details of decision of a control amount of a wavelength of laser light and wavelength control of the laser light based on the control amount will be described later separately in "2.5. Details of wavelength control."

The raw image generation unit 65 may acquire the intensity distribution of the fluorescence from the two-dimensionalization processing unit 625 and then generate a raw file by forming the intensity distribution of the fluorescence in a predetermined file format as image data (a raw image). In this case, the raw image generation unit 65 may acquire information relating to the intensity distribution of the fluorescence such as an acquisition condition of the intensity distribution of the fluorescence (for example, a photographing condition or a scanning condition such as a parameter at the time of photographing) from the system control unit 61a and associate the acquired information with the generated raw file as relevant information.

Particularly, the raw image generation unit 65 according to the present embodiment may associate the information indicating the area V21 in the image V20 designated by the user or an image in the area V21 with the raw file as relevant information as shown in, for example, FIG. 30.

In addition, the raw image generation unit 65 may associate control information indicating the control amount of a wavelength (frequency) of the laser light (excitation light) decided by the wavelength control amount decision unit 613 with the raw file as relevant information. By associating the control information indicating the control amount of a wavelength of the laser light with the raw file as relevant information in this manner, an external device, for example, the information processing device 800, can recognize a degree of fading of the sample based on the control amount.

Note that the raw image generation unit 65 may associate each of the control information decided based on the automatic adjustment by the system control unit 61a and control information changed based on an instruction of the user with the raw file as relevant information. In addition, the raw image generation unit 65 may associate an image based on the intensity distribution of the fluorescence acquired based on each condition (for example, an image that has undergone image processing such as compression) with the raw file together with the control information. In this manner, the raw image generation unit 65 may associate the control information indicating the control amount of the wavelength of the laser light and the image acquired based on the laser light controlled according to the control amount with the raw file for each of a plurality of conditions.

Hereinabove, the configuration of the image acquisition device 1a according to the present embodiment has been described with reference to FIGS. 20 to 30. Next, more details of each configuration of the image acquisition device 1a according to the present embodiment will be described.

2.3. File Format of a Raw File

Figure 31:
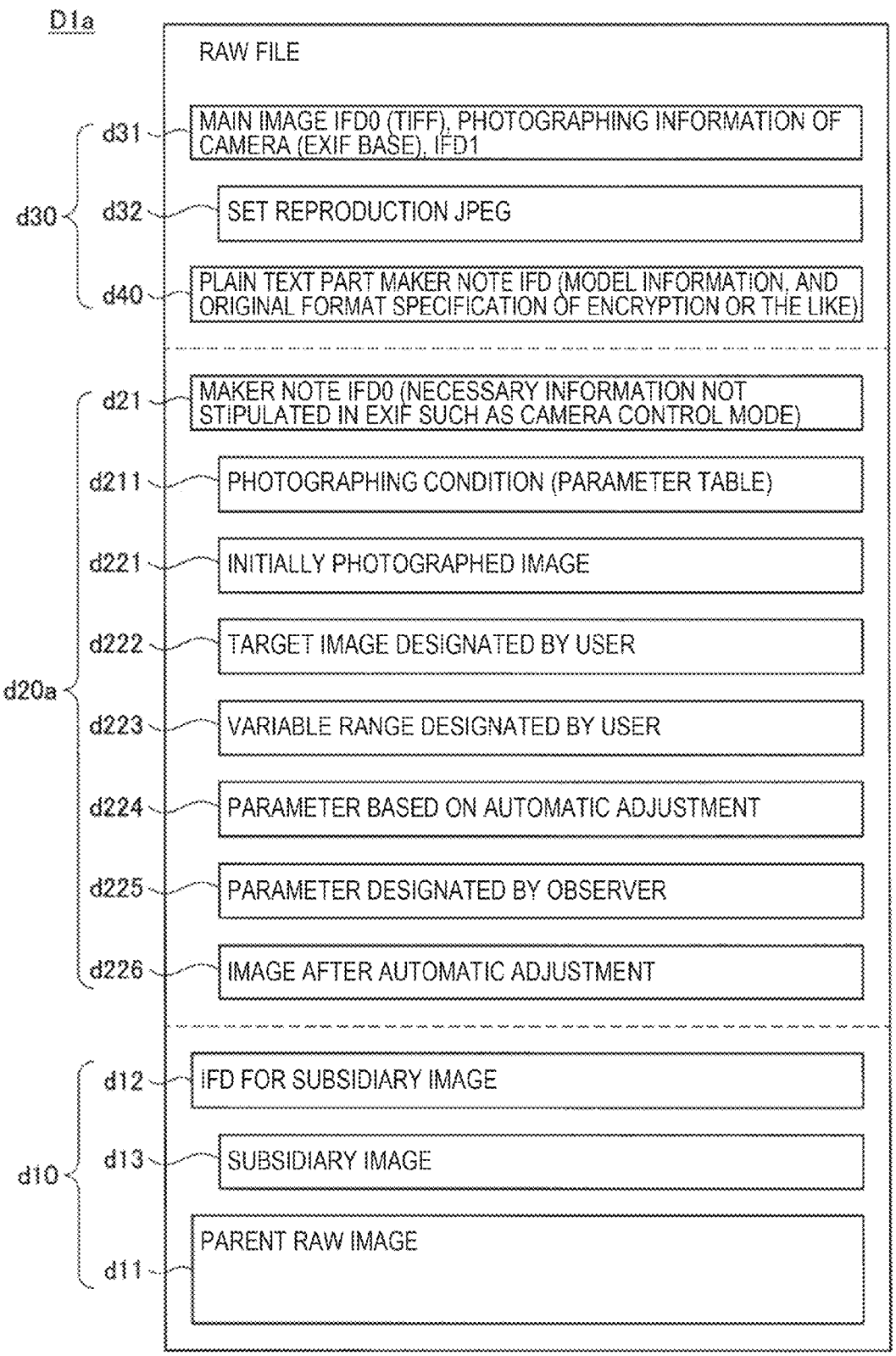
FIG. 31 is a diagram showing an example of a file format of a raw file according to the embodiment.

First, an example of a file format of the raw file D1a according to the present embodiment will be described with reference to FIG. 31. FIG. 31 is a diagram showing the example of the file format of the raw file D1a according to the present embodiment.

As shown in FIG. 31, the raw file D1a according to the present embodiment includes, for example, the data area d10, the basic control information area d30, and an extended area d20a. Note that, since configurations of the data area d10 and the basic control information area d30 are the same as those of the raw file D1 according to the first embodiment (refer to FIG. 19), detailed description thereof will be omitted.

The extended area d20a includes a maker note IFD d21 as shown in FIG. 31. The maker note IFD d21 is an IFD for storing information such as a camera control mode that is not stipulated in the EXIF, and also storing photographing information and control information intrinsic to the image acquisition device 1a.

The maker note IFD d21 according to the present embodiment includes, for example, the photographing condition d211, an initially photographed image d221, a target image designated by a user d222, a variable range designated by a user d223, a parameter based on automatic adjustment d224, a parameter designated by an observer d225, and an image after automatic adjustment d226. Note that the photographing condition d211 is the same as that of the raw file D1 according to the first embodiment described above.

The initially photographed image d221 is an image based on the intensity distribution of the fluorescence acquired before the system control unit 61a controls a wavelength based on the control amount decided by the wavelength control amount decision unit 613. In other words, the initially photographed image d221 indicates an image that is based on the intensity distribution of the fluorescence which has acquired laser light having a wavelength decided in advance (i.e., with an initial setting) according to the sample S serving as an observation target as excitation light.

The target image designated by a user d222 indicates an image of a portion corresponding to an area designated by a user as an observation target cut out of a captured image. In the example shown in FIG. 30, for example, the target image designated by a user d222 is equivalent to the image of the portion denoted by the area V21 cut out from the image V20.

In addition, the variable range designated by a user d223 is information indicating an area designated by the user as an observation target in the captured image. In the example shown in FIG. 31, for example, the variable range designated by a user d223 is equivalent to control information indicating the area V21. Note that the control information indicating the area can be expressed using, for example, coordinates or a vector of the captured image.

The parameter based on automatic adjustment d224 indicates a parameter decided by the system control unit 61a at the time of automatic adjustment such as a wavelength of laser light emitted from the light source 2 decided by the system control unit 61a through the automatic adjustment. As a specific example, the parameter based on automatic adjustment d224 indicates each parameter (for example, a wavelength of laser light) of when the adjustment is performed so as to maximize contrast of a captured image. Note that the parameter based on automatic adjustment d224 may include the image that is based on the intensity distribution of the fluorescence (for example, an image that has undergone image processing such as compression) acquired according to control of the light source 2 based on the parameter decided by the system control unit 61a through the automatic adjustment.

The parameter designated by an observer d225 indicates a parameter decided by the system control unit 61a based on designation from the user. The parameter designated by an observer d225 may include the image that is based on the intensity distribution of the fluorescence (for example, an image that has undergone image processing such as compression) acquired according to control of the light source 2 based on the parameter decided through designation from the user.

As described above, by recording relevant information indicating control of a wavelength (frequency) of laser light (excitation light) (i.e., the parameter based on automatic adjustment d224 and the parameter designated by an observer d225) in the raw file D1a, an external device, for example, the information processing device 800, can recognize a degree of fading of the sample based on the relevant information. In addition, by recording the images that are based on the intensity distribution of the fluorescence acquired according to control of the light source 2 based on the parameters, the external device such as the information processing device 800 can present the images according to each condition to the user together with acquisition conditions (i.e., the parameters) of the images.

The image after automatic adjustment d226 indicates an image based on the intensity distribution of the fluorescence acquired according to control of the light source 2 based on a finally decided parameter. Note that the image after automatic adjustment d226 may be an image cut out based on the variable range designated by a user d223.

Hereinabove, the file format of the raw file D1a according to the present embodiment has been described with reference to FIG. 31. Note that the file format of the raw file D1a shown above is merely an example, and it is needless to say that all kinds of information may not necessarily be included therein.

2.4. Flow of Operations of the Image Acquisition Device

Figure 32:
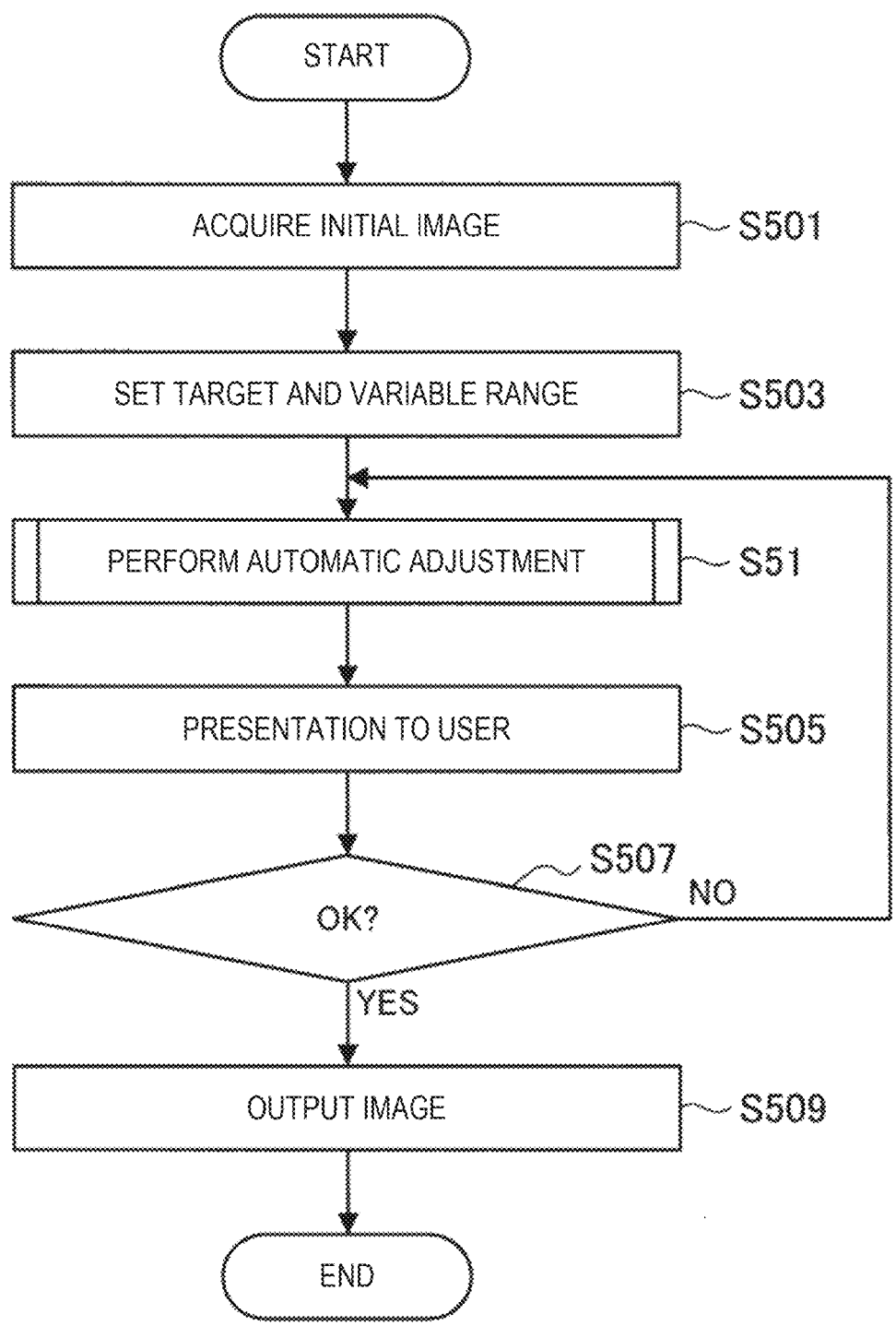
FIG. 32 is a flowchart showing an example of the flow of a series of operations of the image acquisition device according to the embodiment.

Next, the flow of a series of operations of the image acquisition device 1a according to the present embodiment will be described with reference to FIG. 32. FIG. 32 is a flowchart showing an example of the flow of the series of operations of the image acquisition device 1a according to the present embodiment.

(Step S501)

First, the control unit 6a of the image acquisition device 1a controls a wavelength of excitation light emitted from the light source 2 (in other words, controls the wavelength based on an initial setting) according to the sample S that is a measurement target. The excitation light emitted from the light source 2 based on the control of the wavelength by the control unit 6a is guided to the sample S by the measurement unit 3 (i.e., the scanning system (detection system) 5a and the microscope unit 4). Then, the measurement unit 3 scans the top of the sample S using the excitation light emitted from the light source 2, and detects fluorescence emitted from the sample S. The measurement unit 3 outputs a result of detecting the fluorescence to the control unit 6a.

The control unit 6a generates intensity distribution of the fluorescence based on the detection result of the fluorescence acquired from the measurement unit 3, and performs predetermined image processing (for example, a noise removal process and a compression process) on the intensity distribution of the fluorescence, thereby generating image data. Then, it is better for the control unit 6a to display a U/I for designating an area of the image data on the display unit 72 along with the generated image data. Accordingly, a user can designate an area to be observed for the image displayed on the display unit 72 through the condition designation unit 71.

(Step S503)

The control unit 6a receives designation of the area to be observed of the image data through the condition designation unit 71 based on a user input. Note that the area designated by the user is equivalent to a variable range and an object in the area (a part of the sample S) is set to be a target.

(Step S51)

The control unit 6a controls the wavelength of the excitation light emitted from the light source 2 for an image in the area designated based on the user input so that an object in the image is clearly displayed (for example, contrast of the area is maximized). Note that details thereof will be described later separately in "2.5. Details of wavelength control."

(Step S505)

The control unit 6a acquires the intensity distribution of the fluorescence based on the excitation light after the wavelength control while controlling the wavelength of the excitation light emitted from the light source 2, and then generates image data based on the acquired intensity distribution of the fluorescence. Then, the control unit 6a causes the generated image data to be displayed on the display unit 72. Accordingly, the user can check an image that has been adjusted based on the control of the wavelength of the excitation light emitted from the light source 2.

(Step S507)

Note that the image acquisition device 1a according to the present embodiment may receive an instruction from the user with respect to whether or not further adjustment is necessary for the adjusted image. In this case, when the user instructs that further adjustment is necessary (No in Step S507), for example, the image acquisition device 1a changes a condition (for example, a parameter such as a threshold value relating to determination of contrast) and controls the wavelength of the excitation light again.

(Step S509)

When the instruction that further adjustment is not necessary for the adjusted image is given by the user (Yes in Step S507), the image acquisition device 1a according to the present embodiment generates the raw file D1 based on the intensity distribution of the fluorescence acquired based on the excitation light of that time point.

So far, the flow of the series of operations of the image acquisition device 1a according to the present embodiment has been described with reference to FIG. 32. Note that the series of operations of the image acquisition device 1a described above is merely an example, and a flow thereof is not necessarily limited to that of the operations described above. As a specific example, the image acquisition device 1a may be operated so that the user can directly or indirectly designate a wavelength of the excitation light.

2.5. Details of Wavelength Control

<<2.5.1. Principle of Wavelength Control: A Case in which a Sample is Observed Using a Plurality of Observation Wavelengths>>

Next, details of an operation relating to wavelength control of laser light emitted from the light source 2 by the control unit 6a according to the present embodiment will be described with reference to FIGS. 33 to 36. Note that, in this description, the principle of wavelength control of the image acquisition device 1a according to the present embodiment will be described with reference to FIGS. 33 to 35 exemplifying a case in which a composition of a sample is identified using a plurality of (for example, two) observation wavelengths. In addition, a case in which a composition of a sample is measured using a single observation wavelength will be described later separately in "2.5.2. An aspect of wavelength control: a case in which a sample is observed using a single observation wavelength."

Figure 33:
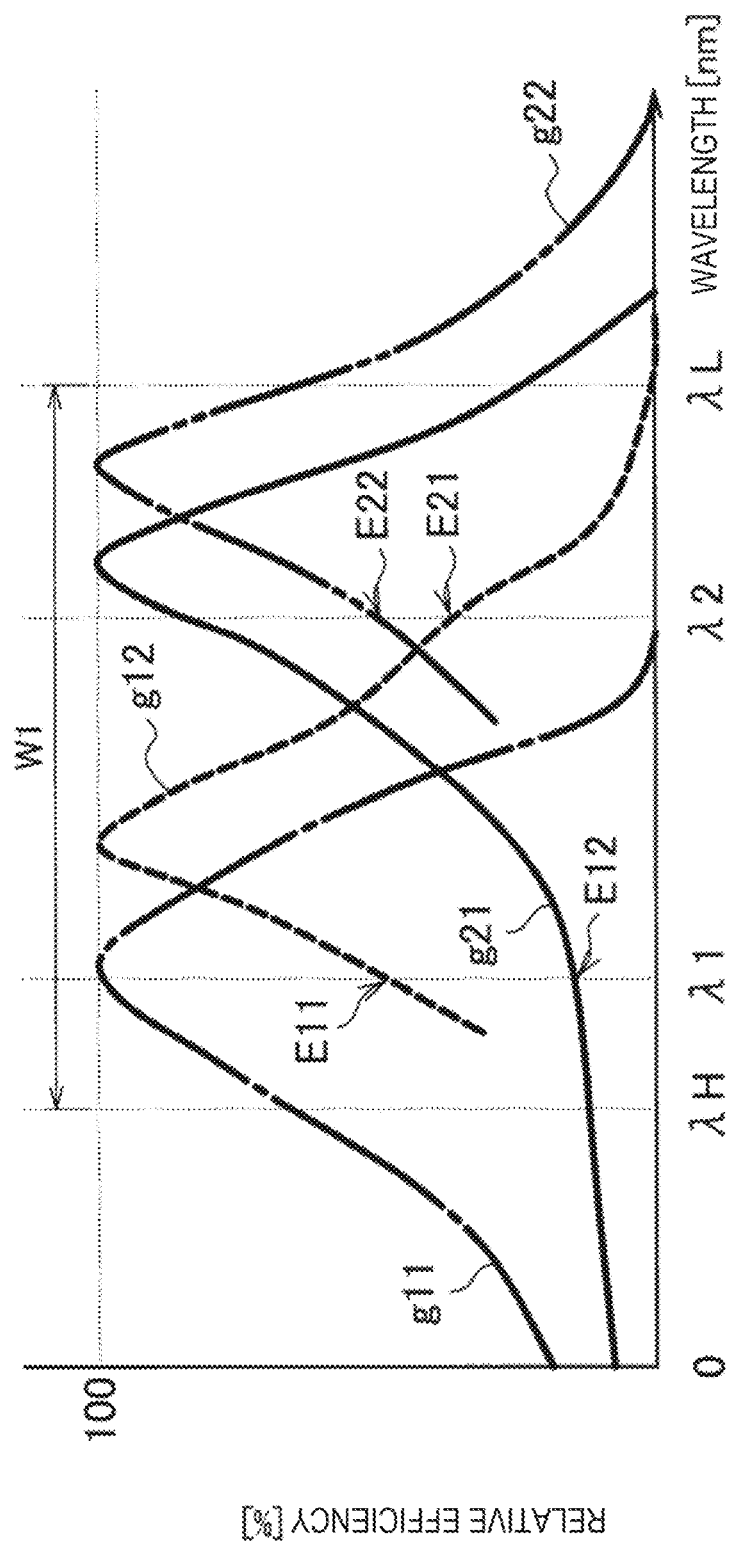
FIG. 33 is an illustrative diagram for describing the principle of wavelength control of laser light emitted from the light source.

First, FIG. 33 is referred to. FIG. 33 is an illustrative diagram for describing the principle of wavelength control of laser light emitted from the light source 2, showing an example of a relation between wavelengths of laser light output from the light source 2, and excitation spectrums and fluorescence spectrums of fluorochromes included in the sample S. Note that description will be provided hereinbelow by setting two different kinds of fluorochromes F1 and F2 included in the sample S as observation targets and the wavelengths of excitation light that cause the fluorochromes F1 and F2 to emit light (which may be referred to hereinbelow as "light emission wavelengths") to $\lambda 1$ and $\lambda 2$ respectively.

In FIG. 33, the horizontal axis represents wavelength [nm] and the vertical axis represents relative efficiency [%]. In addition, reference numeral g11 represents the excitation spectrum of the fluorochrome F1, and reference numeral g12 represents the fluorescence spectrum of the fluorochrome F1. In addition, reference numeral g21 represents the excitation spectrum of the fluorochrome F2, and reference numeral g22 represents the fluorescence spectrum of the fluorochrome F2.

In addition, fluorescence relative efficiencies of the fluorochromes F1 and F2 at the light emission wavelength $\lambda 1$ obtained using fluorescence wavelength distribution (i.e., fluorescence spectrum) g12 are set to $E11=E(\lambda 1, F1)$ and $E12=E(\lambda 1, F2)$. In addition, fluorescence relative efficiencies of the fluorochromes F1 and F2 at the light emission wavelength $\lambda 2$ obtained using fluorescence wavelength distribution (i.e., fluorescence spectrum) g22 are set to $E21=E(\lambda 2, F1)$ and $E22=E(\lambda 2, F2)$.

In addition, the light source 2 is set to be configured such that a wavelength of the output laser light is controllable per wavelength $\lambda s$ within a band W1 defined between wavelengths $\lambda H$ to $\lambda L$.

Figure 34:
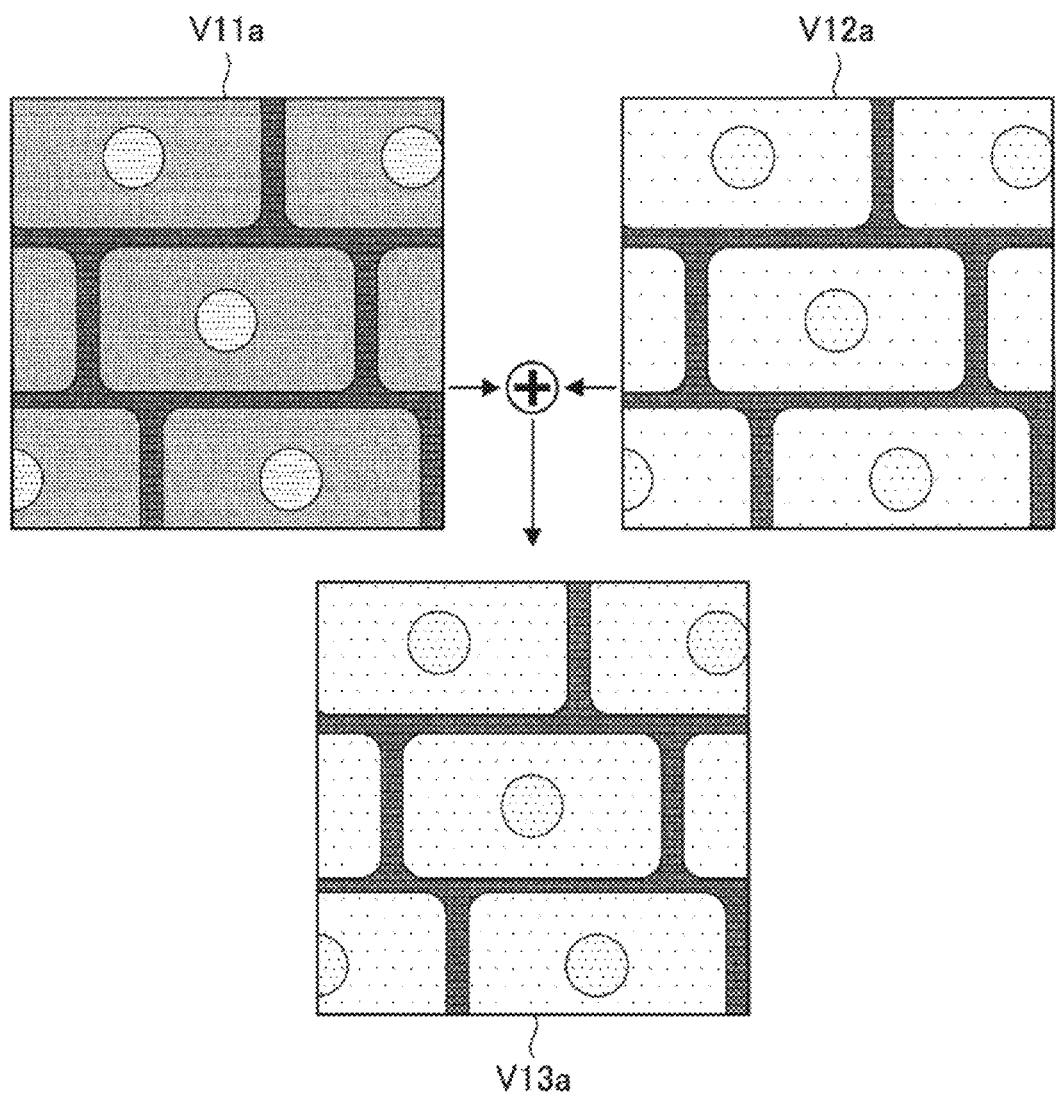
FIG. 34 is an illustrative diagram for describing the principle of wavelength control of laser light emitted from the light source.

The control unit 6a of the image acquisition device 1a according to the present embodiment generates an identification image of two colors by combining intensity distributions of the fluorescence acquired at each of the light emission wavelengths $\lambda 1$ and $\lambda 2$. FIG. 34 is, for example, an illustrative diagram for describing the principle of wavelength control of the laser light emitted from the light source, showing an example of the identification image of two colors generated by combining intensity distributions of the fluorescence acquired at each of the light emission wavelengths $\lambda 1$ and $\lambda 2$.

In FIG. 34, reference numeral V11a represents the intensity distribution of the fluorescence at the light emission wavelength $\lambda 1$, and reference numeral V12a represents the intensity distribution of the fluorescence at the light emission wavelength $\lambda 2$. In addition, reference numeral V13a represents an example of the identification image of two colors obtained by combining the intensity distributions of the fluorescence V11a and V12a.

As shown in FIG. 34, when the intensity distributions of the fluorescence V11a and V12a acquired respectively at the light emission wavelengths $\lambda 1$ and $\lambda 2$ are combined, the obtained identification image V13a does not necessarily have a high contrast.

Thus, the control unit 6a (specifically, the system control unit 61a) of the image acquisition device 1a according to the present embodiment controls the light emission wavelengths λ1 and λ2 to maximize, for example, the contrast of the identification image V13a, thereby adjusting ratios of intensities of the fluorescence obtained at each of the light emission wavelengths λ1 and λ2.

Figure 35:
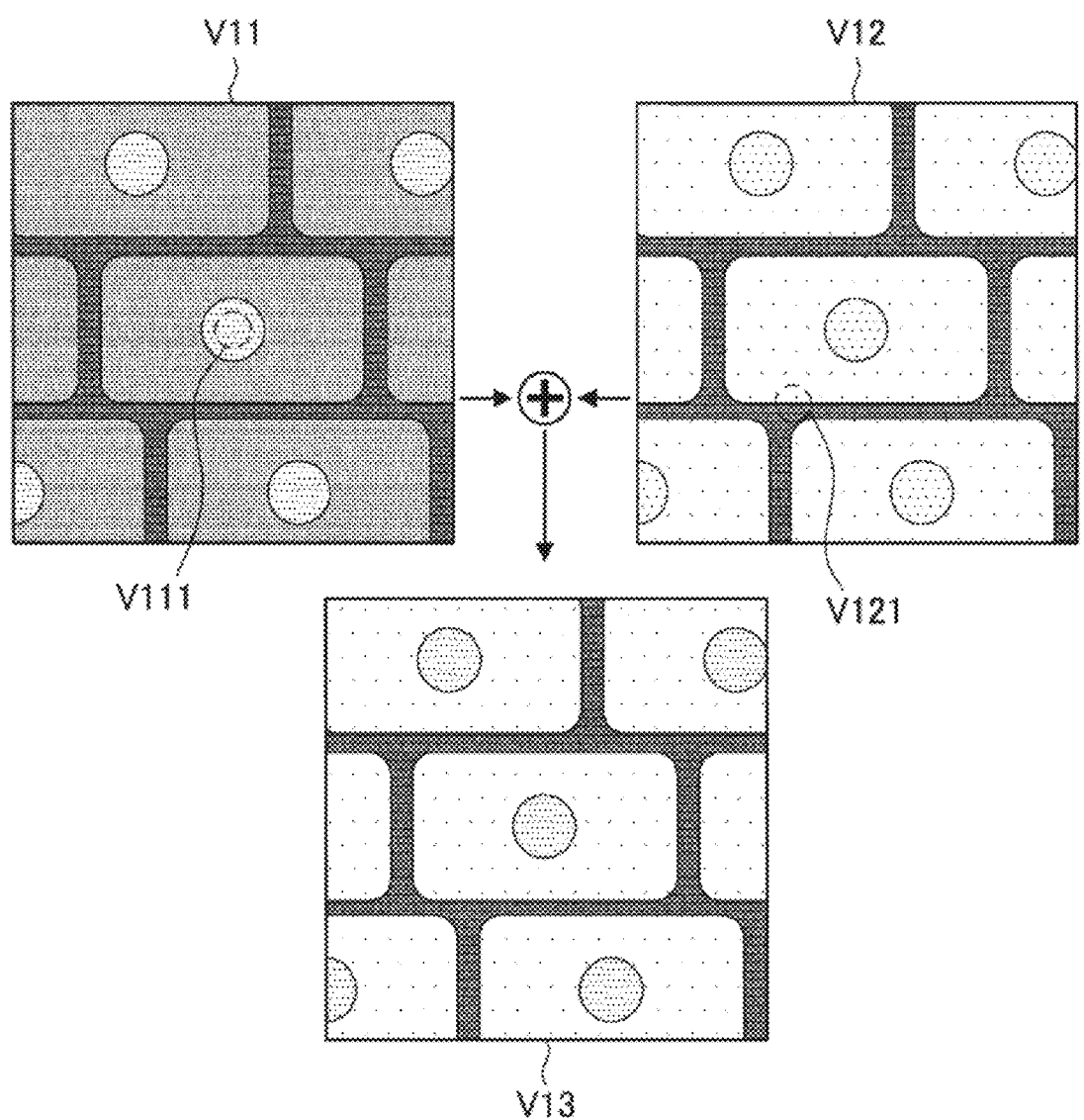
FIG. 35 is an illustrative diagram for describing the principle of wavelength control of laser light emitted from the light source.

Hereinbelow, an example of a process of the system control unit 61a to compute the contrast of the identification image of two colors generated by combining the intensity distributions of the fluorescence that are obtained based on each of the light emission wavelengths λ1 and λ2 will be described with reference to FIG. 35. FIG. 35 is an illustrative diagram for describing the principle of wavelength control of laser light emitted from the light source 2 and for describing an example of a computation method of the contrast used when a sample is observed using a plurality of observation wavelengths.

In FIG. 35, reference numeral V11 represents the intensity distribution of the fluorescence at the light emission wavelength λ1, and reference numeral V12 represents the intensity distribution of the fluorescence at the light emission wavelength λ2. In addition, reference numeral V13 represents an example of the identification image of two colors obtained by combining the intensity distributions of the fluorescence V11 and V12.

First, the system control unit 61a computes initial values of the light emission wavelengths λ1 and λ2 based on fluorescence relative efficiencies E11=E(λ1, F1), E12=E(λ1, F2), E21=E(λ2, F1), and E22=E(λ2, F2) to cause formula 12 shown below to have a maximum value.

$$|E(\lambda 1, F1) - E(\lambda 1, F2)| + |E(\lambda 2, F1) - (\lambda 2, F2)| \qquad \text{Formula 12}$$

Note that it is better to configure, for example, the storage unit 66 as a database and to store data indicating the excitation spectrums and the fluorescence spectrums of each of the fluorochromes F1 and F2 in the database in advance. Accordingly, the system control unit 61a can compute the fluorescence relative efficiencies E11, E12, E21, and E22 based on the data indicating the excitation spectrums and the fluorescence spectrums of each of the fluorochromes F1 and F2 stored in the storage unit 66 (database).

After the initial values of the light emission wavelengths λ1 and λ2 are decided as described above, the system control unit 61a controls such that the light source 2 outputs laser light having the decided light emission wavelengths λ1 and λ2, and then acquires the intensity distributions of the fluorescence based on each of the light emission wavelengths λ1 and λ2. Accordingly, the intensity distributions of the fluorescence V11 and V12 based on the initial values of the light emission wavelengths λ1 and λ2 are obtained.

Next, the system control unit 61a specifies coordinates V111=(x1, y1) having a high luminance (for example, a maximum luminance) from the acquired intensity distribution of the fluorescence V11. Likewise, the system control unit 61a specifies coordinates V121=(x2, y2) having a high luminance from the acquired intensity distribution of the fluorescence V12.

After the coordinates V111 and V121 are specified, the system control unit 61a computes luminances L(λ1, x1, y1) and L(λ1, x2, y2) of the coordinates V111 and V121 in the intensity distribution of the fluorescence V11. Likewise, the system control unit 61a computes luminances L(λ2, x1, y1) and L(λ2, x2, y2) of the coordinates V111 and V121 in the intensity distribution of the fluorescence V12.

The system control unit 61a computes contrast C(λ1, λ2) based on the computed luminances L(λ1, x1, y1), L(λ1, x2, y2), L(λ2, x1, y1), and L(λ2, x2, y2) and formula 13 shown below.

$$C(\lambda 1, \lambda 2) = |L(\lambda 1, x1, y1) - L(\lambda 2, x1, y1)| - |L(\lambda 1, x2, y2) - L(\lambda 2, x2, y2)| \qquad \text{Formula 13}$$

From the above operation, the contrast C(λ1, λ2) of an identification image V13 of two colors generated by combining the intensity distributions V11 and V12 of the fluorescence obtained based on each of the light emission wavelengths λ1 and λ2 is computed.

Note that the system control unit 61a repeats control of the light emission wavelengths λ1 and λ2, and computation and evaluation of the contrast C(λ1, λ2) based on the controlled light emission wavelengths λ1 and λ2 to adjust the light emission wavelengths λ1 and λ2 so as to cause the contrast C(λ1, λ2) to have a maximum value.

Figure 36:
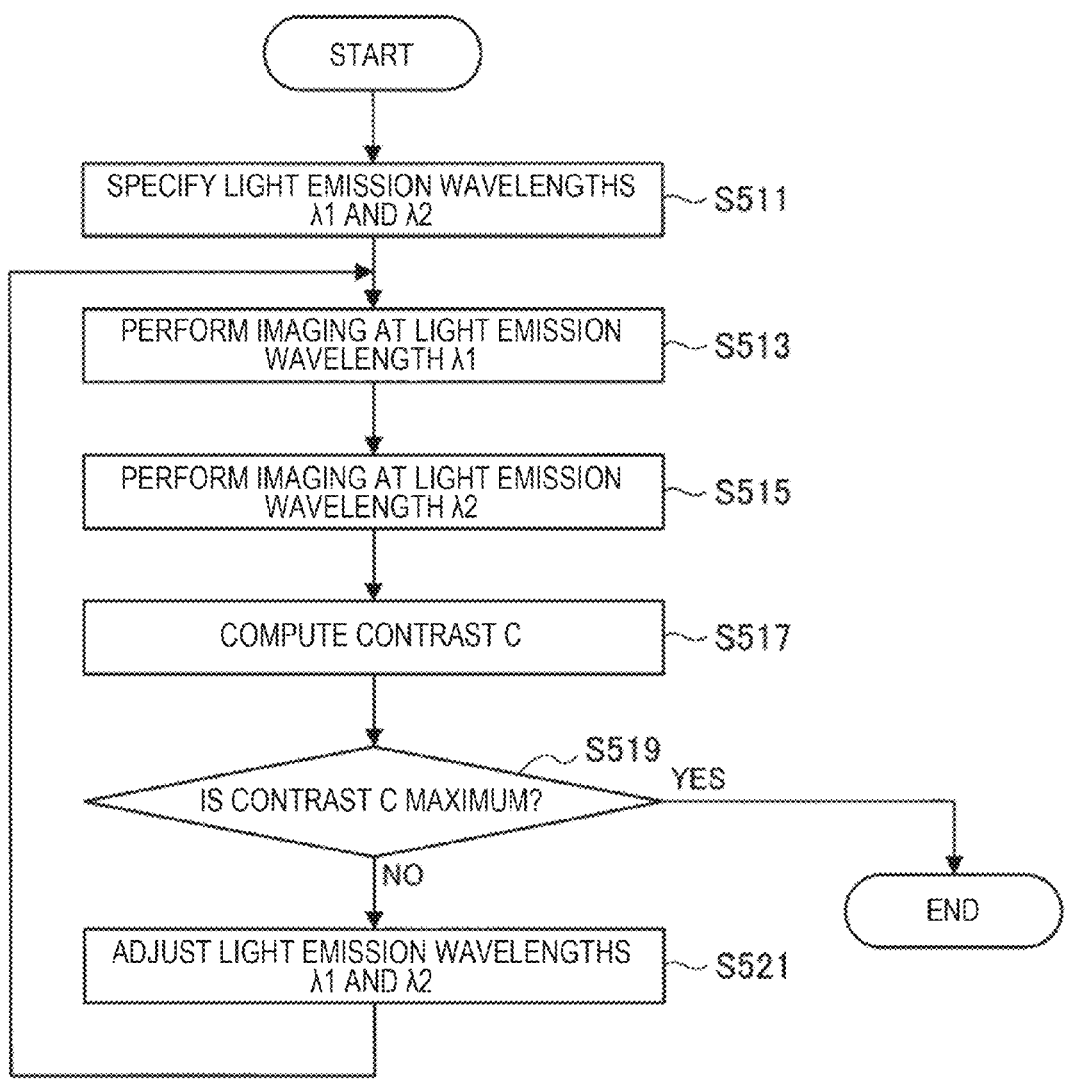
FIG. 36 is a flowchart for describing the flow of a process relating to wavelength control of laser light emitted from the light source.

Next, the flow of the control of the light emission wavelengths λ1 and λ2 by the system control unit 61a when a sample is observed using the plurality of observation wavelengths will be described with reference to FIG. 36. FIG. 36 is a flowchart for describing the flow of a process relating to wavelength control of laser light emitted from the light source 2, showing an example in which the sample is observed using the plurality of observation wavelengths.

(Step S511)

First, the system control unit 61a computes the initial values of the light emission wavelengths λ1 and λ2 based on the fluorescence relative efficiencies E11=E(λ1, F1), E12=E(λ1, F2), E21=E(λ2, F1), and E22=E(λ2, F2). Note that the initial values of the light emission wavelengths λ1 and λ2 may be computed so as to cause formula 12 described above to have a maximum value.

(Step S513)

Next, the system control unit 61a controls such that the wavelength of the excitation light emitted from the light source 2 becomes the computed light emission wavelength 1. Accordingly, a fluorescence detection result obtained using the controlled excitation light is output from the measurement unit 3 to the distribution information generation unit 62a. Then, the distribution information generation unit 62a generates the intensity distribution of the fluorescence V11 at the light emission wavelength λ1 based on the acquired fluorescence detection result. The distribution information generation unit 62a outputs the generated intensity distribution of the fluorescence V11 to the system control unit 61a. Through the above operation, the system control unit 61a acquires the intensity distribution of the fluorescence V11 that is based on the controlled excitation light from the distribution information generation unit 62a.

(Step S515)

Next, the system control unit 61a controls such that the wavelength of the excitation light emitted from the light source 2 becomes the computed light emission wavelength λ2. Accordingly, a fluorescence detection result obtained using the controlled excitation light is output from the measurement unit 3 to the distribution information generation unit 62a. Then, the distribution information generation unit 62a generates the intensity distribution of the fluorescence V12 at the light emission wavelength λ2 based on the acquired fluorescence detection result. The distribution information generation unit 62a outputs the generated intensity distribution of the fluorescence V12 to the system control unit 61a. Through the above operation, the system control unit 61a acquires the intensity distribution of the fluorescence V12 that is based on the controlled excitation light from the distribution information generation unit 62a.

(Step S517)

The system control unit 61a computes the contrast $C(\lambda 1, \lambda 2)$ based on the intensity distributions of the fluorescence V11 and V12 based on each of the generated light emission wavelengths $\lambda 1$ and $\lambda 2$.

(Step S521)

The system control unit 61a continues the process described above (No in Step S519) while adjusting the light emission wavelengths $\lambda 1$ and $\lambda 2$ until the contrast $C(\lambda 1, \lambda 2)$ has the maximum value and finishes the series of the processes (Yes in Step S519) when the contrast $C(\lambda 1, \lambda 2)$ has the maximum value.

Next, an example of a method of the system control unit 61a specifying the light emission wavelengths $\lambda 1$ and $\lambda 2$ that cause the contrast $C(\lambda 1, \lambda 2)$ to have the maximum value will be described.

First, the system control unit 61a sets the case in which both of the light emission wavelengths $\lambda 1$ and $\lambda 2$ have the initial values as a reference state and then acquires the intensity distributions of the fluorescence V11 for when the light emission wavelength $\lambda 1$ is changed by $\lambda s$ in the positive direction from the reference state and when it is changed by $\lambda s$ in the negative direction therefrom. Then, the system control unit 61a computes the contrast $C(\lambda 1, \lambda 2)$ based on each of the acquired intensity distributions of the fluorescence V11 and then specifies a change direction of the light emission wavelength $\lambda 1$ in which the contrast $C(\lambda 1, \lambda 2)$ increases.

Similarly, the system control unit 61a acquires the intensity distributions of the fluorescence V12 for when the light emission wavelength $\lambda 2$ is changed by $\lambda s$ in the positive direction from the reference state and when it is changed by $\lambda s$ in the negative direction therefrom. Then, the system control unit 61a computes the contrast $C(\lambda 1, \lambda 2)$ based on each of the acquired intensity distributions of the fluorescence V12 and then specifies a change direction of the light emission wavelength $\lambda 2$ in which the contrast $C(\lambda 1, \lambda 2)$ increases.

Then, the system control unit 61a changes each of the light emission wavelengths $\lambda 1$ and $\lambda 2$ by each $\lambda s$ from the reference state in the specified direction a plurality of times (for example, two times) and thereby computes the contrast $C(\lambda 1, \lambda 2)$ for each of the changes. Then, the system control unit 61a specifies a light emission wavelength between the light emission wavelengths $\lambda 1$ and $\lambda 2$ at which a change amount of the contrast $C(\lambda 1, \lambda 2)$ is greater (in other words, a light emission wavelength at which the difference of the contrast $C(\lambda 1, \lambda 2)$ before and after the control is greater) based on the computation results of the contrast $C(\lambda 1, \lambda 2)$. Note that description will be provided hereinbelow on the assumption that the change amount of the contrast $C(\lambda 1, \lambda 2)$ is greater when the light emission wavelength $\lambda 1$ is changed than when the light emission wavelength $\lambda 2$ is changed.

The system control unit 61a computes the contrast $C(\lambda 1, \lambda 2)$ while fixing the light emission wavelength $\lambda 2$ and changing the light emission wavelength $\lambda 1$ by each $\lambda s$ in the specified direction, and thereby specifies the light emission wavelength $\lambda 1$ at which the contrast $C(\lambda 1, \lambda 2)$ has the maximum value.

The system control unit 61a computes the contrast $C(\lambda 1, \lambda 2)$ while fixing the light emission wavelength $\lambda 1$ and changing the light emission wavelength $\lambda 2$ by each $\lambda s$ in the specified direction, and thereby specifies the light emission wavelength $\lambda 2$ at which the contrast $C(\lambda 1, \lambda 2)$ has the maximum value.

Through the above operation, the system control unit 61a specifies the light emission wavelengths $\lambda 1$ and $\lambda 2$ at which the contrast $C(\lambda 1, \lambda 2)$ has the maximum value. Note that it is needless to say that the example shown above is merely an example and the method is not particularly limited as long as the light emission wavelengths $\lambda 1$ and $\lambda 2$ at which the contrast $C(\lambda 1, \lambda 2)$ has the maximum value can be specified.

So far, details of the operation relating to the wavelength control of laser light emitted from the light source 2 by the control unit 6a according to the present embodiment have been described with reference to FIGS. 33 to 36 exemplifying the case in which the composition of the sample is identified using the plurality of observation wavelengths.

<<2.5.2. An Aspect of Wavelength Control: A Case in which a Sample is Observed Using a Single Observation Wavelength>>

Next, a case in which a sample is observed using a single observation wavelength will be described as an aspect of the operation relating to control by the system control unit 61a according to the present embodiment of a wavelength of laser light emitted from the light source 2. Note that, in the present description, the system control unit 61a is assumed to target the fluorochrome F1 in the sample S and control the light emission wavelength $\lambda 1$.

In this case, the system control unit 61a first decides the initial value of the light emission wavelength $\lambda 1$ so that the fluorescence relative efficiency $E11=E(\lambda 1, F1)$ has the maximum value. Note that the system control unit 61a may compute the light emission wavelength $\lambda 1$ at which the fluorescence relative efficiency E11 has the maximum value based on the peak value of the excitation spectrum of the fluorochrome F1.

Next, the system control unit 61a sets the state of the initial value of the light emission wavelength $\lambda 1$ as a reference state and then acquires the intensity distributions of the fluorescence V11 for the cases in which the light emission wavelength $\lambda 1$ is changed by $\lambda s$ in the positive direction from the reference state and in which the wavelength is changed by $\lambda s$ in the negative direction therefrom. Then, the system control unit 61a computes contrast of the acquired intensity distributions of the fluorescence V11 and then specifies the change direction of the light emission wavelength $\lambda 1$ in which the contrast increases. Note that, as a computation method of contrast of the intensity distribution of the fluorescence V11, for example, it is possible to apply a so-called general contrast computation method as the contrast computation method that is based on the maximum and minimum pixel values present in the intensity distribution of the fluorescence V11.

After the change direction of the light emission wavelength $\lambda 1$ in which the contrast increases is specified, the system control unit 61a computes contrast while changing the light emission wavelength $\lambda 1$ by each $\lambda s$ in the change direction, and thereby specifies the light emission wavelength $\lambda 1$ at which the contrast has a maximum value.

Through the above operation, the system control unit 61a specifies the light emission wavelength $\lambda 1$ at which the contrast has the maximum value. Note that it is needless to say that the example shown above is merely an example and the method is not particularly limited as long as the light emission wavelength $\lambda 1$ at which the contrast has the maximum value can be specified.

2.6. Conclusion

As described above, the image acquisition device 1a according to the present embodiment uses the laser module that can control a wavelength of output laser light (excitation light) as the light source 2, and controls the wavelength of the laser light based on an intensity distribution of observed fluorescence. With this configuration, the image acquisition device 1a according to the present embodiment can acquire a high contrast image without requiring, for example, an observer (user) to perform a troublesome task such as controlling operations of the light source 2 while checking observation results or switching the light source 2 itself.

In addition, the image acquisition device 1a according to the present embodiment can control a wavelength of laser light so that contrast of an acquired intensity distribution of fluorescence has a maximum value even in a situation in which the wavelength of the laser light changes according to an increase of temperature. For this reason, the image acquisition device 1a according to the present embodiment can stabilize the wavelength of the laser light even when, for example, the light source 2 is mounted in the same housing, and thus the size of the image acquisition device 1a itself can be reduced.

3. Third Embodiment

3.1. Overview of an Image Acquisition Device

Next, an image acquisition device according to a third embodiment will be described. In the first embodiment described above, intensity control and correction of emitted light from the light source 2 have been described, and wavelength control of emitted light from the light source 2 has been described in the second embodiment, however, it is needless to say that both of the embodiments may be combined and implemented. Thus, in the third embodiment, a configuration in which the image acquisition device 1 according to the first embodiment and the image acquisition device 1a according to the second embodiment described above are combined will be described. Note that the image acquisition device according to the present embodiment may be referred to hereinafter as an "image acquisition device 1b" in order to be distinguished from the image acquisition device 1 according to the first embodiment and the image acquisition device 1a according to the second embodiment described above.

3.2. Configuration of the Image Acquisition Device

<<3.2.1. Configuration of an Optical System>>

First, a configuration of an optical system of the image acquisition device 1b according to the present embodiment will be described. The configuration of the optical system of the image acquisition device 1b according to the present embodiment is the same as that of the optical system of the image acquisition device 1 according to the first embodiment shown in FIG. 14.

That is, in the image acquisition device 1b according to the present embodiment, the light source 2 includes the wavelength conversion module (OPO) 250, thereby converting an input laser light (pump light) into laser light having two wavelengths (in other words, signal light and idler light) and then outputs them. In the image acquisition device 1b according to the present embodiment, any one of the signal light and the idler light output from the light source 2 is radiated toward the sample S as excitation light. It will be assumed below that the signal light is radiated toward the sample S as excitation light.

Note that the configuration in which excitation light is radiated toward the sample S is the same as the optical system of the image acquisition device 1w (refer to FIG. 10) according to the comparative example described above and the optical system of the image acquisition device (refer to FIGS. 14 and 27) according to each embodiment. In other words, the excitation light emitted from the light source 2 is guided to the objective lens 42 via the beam-forming lens 511, the galvano mirror 51, the lens 513, the mirror 517, the lens 515, and the dichroic mirror 52, and then collected toward the sample S by the objective lens 42.

In addition, when the sample S is irradiated with the excitation light, some molecules of the sample S are excited by the excitation light and thereby emit fluorescence, and the fluorescence forms an image on the detection plane of the PMT 53 via the objective lens 42, the dichroic mirror 52, the image-forming lens 521, and the emission filter 523. At this time, light other than colored light (natural light) that has been enlarged by the objective lens 42 is absorbed by the emission filter 523, (in other words, only the colored light is transmitted therethrough), and then an image of the colored light that has lost the natural light is formed on the PMT 53.

<<3.2.2. Functional Configuration of the Image Acquisition Device>>

Figure 37:
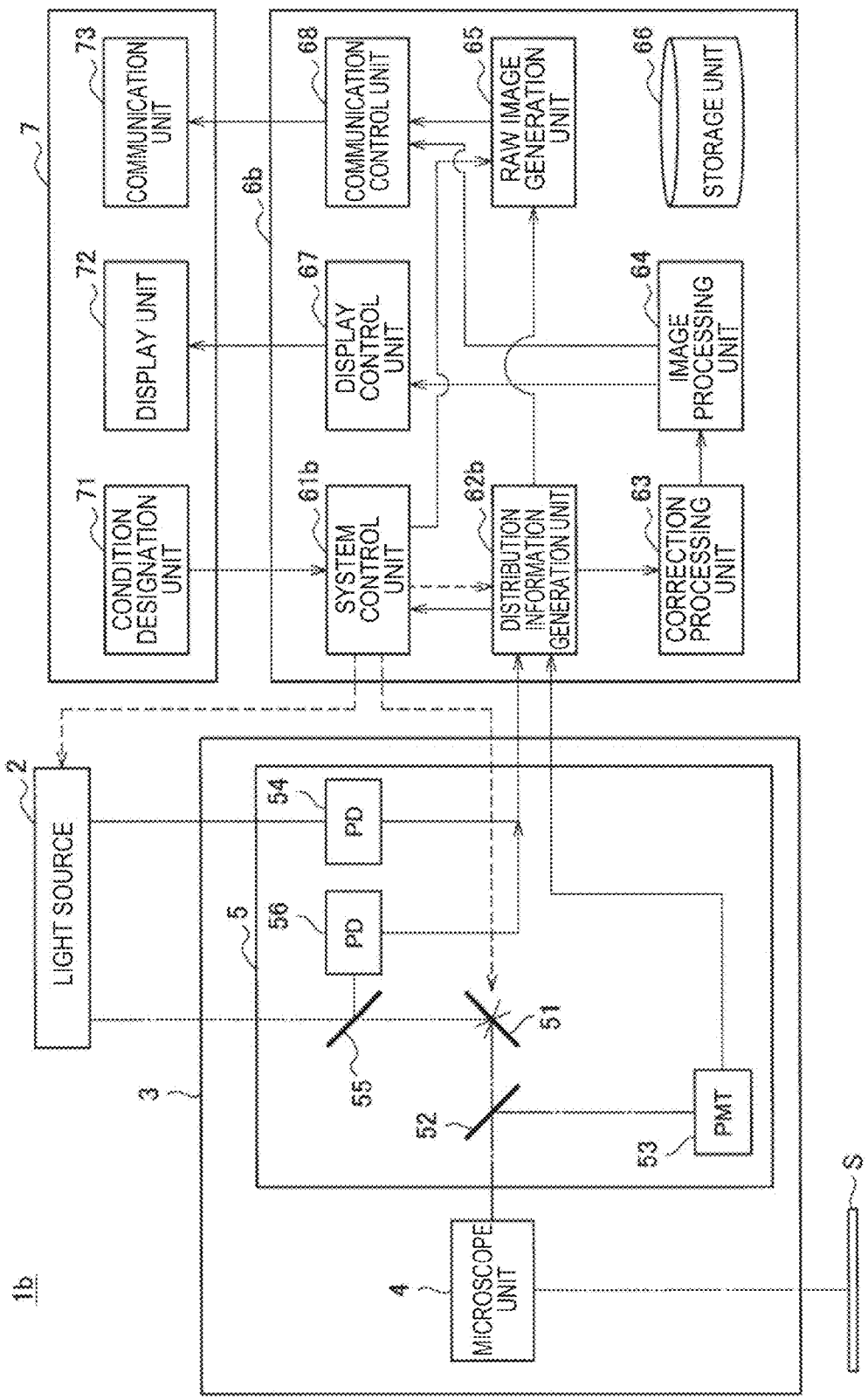
FIG. 37 is an illustrative diagram for describing an example of a functional configuration of an image acquisition device according to a third embodiment of the present disclosure.

Next, an example of the functional configuration of the image acquisition device 1b according to the present embodiment will be described with reference to FIG. 37. As shown in FIG. 37, the image acquisition device 1b according to the present embodiment includes the light source 2, the measurement unit 3, a control unit 6b, and the I/F 7. In addition, the measurement unit 3 includes the microscope unit 4 and a scanning system (detection system) 5. Note that the configurations of the light source 2, the microscope unit 4, and the I/F 7 are the same as those of the image acquisition device 1 according to the first embodiment described above. For this reason, description will be provided hereinbelow focusing particularly on the configuration of the control unit 6b which are different from the image acquisition device 1 according to the first embodiment. Note that, in the example shown in FIG. 37, each constituent element of the scanning system (detection system) 5a corresponds to that to which the same reference numeral is given in the optical system shown in FIG. 14. In addition, some of the constituent elements shown in FIG. 14 are omitted in the example shown in FIG. 37.

As shown in FIG. 37, fluorescence generated from the sample S by the radiated excitation light is guided to the scanning system (detection system) 5 via the microscope unit 4, and then detected by the PMT 53 of the scanning system (detection system) 5. The PMT 53 converts the detected fluorescence into an electric signal through photoelectric conversion at a sampling rate set in advance, and outputs the signal to the control unit 6b as data indicating an intensity of the fluorescence.

In addition, the PD 54 measures the intensity of the idler light at a sampling rate set in advance. The PD 54 converts the measured intensity of the idler light into an electric signal, and outputs the signal to the control unit 6b as data indicating the intensity of the idler light. Note that, instead of the PD 54, the PD 56 that measures an intensity of the excitation light (signal light) may be provided. As described, the configurations of the PMT 53, the PD 54, and the PD 56 are the same as those of the image acquisition device 1 according to the first embodiment described above.

As shown in FIG. 37, the control unit 6b includes a system control unit 61b, a distribution information generation unit 62b, the correction processing unit 63, the image processing unit 64, the raw image generation unit 65, the storage unit 66, the display control unit 67, and the communication control unit 68. Note particularly that the control unit 6b according to the present embodiment has the system control unit 61b and the distribution information generation unit 62b with different configurations from the control unit 6 according to the first embodiment described above (refer to FIGS. 15 and 16) and control unit 6a according to the second embodiment (refer to FIGS. 28 and 29).

Figure 38:
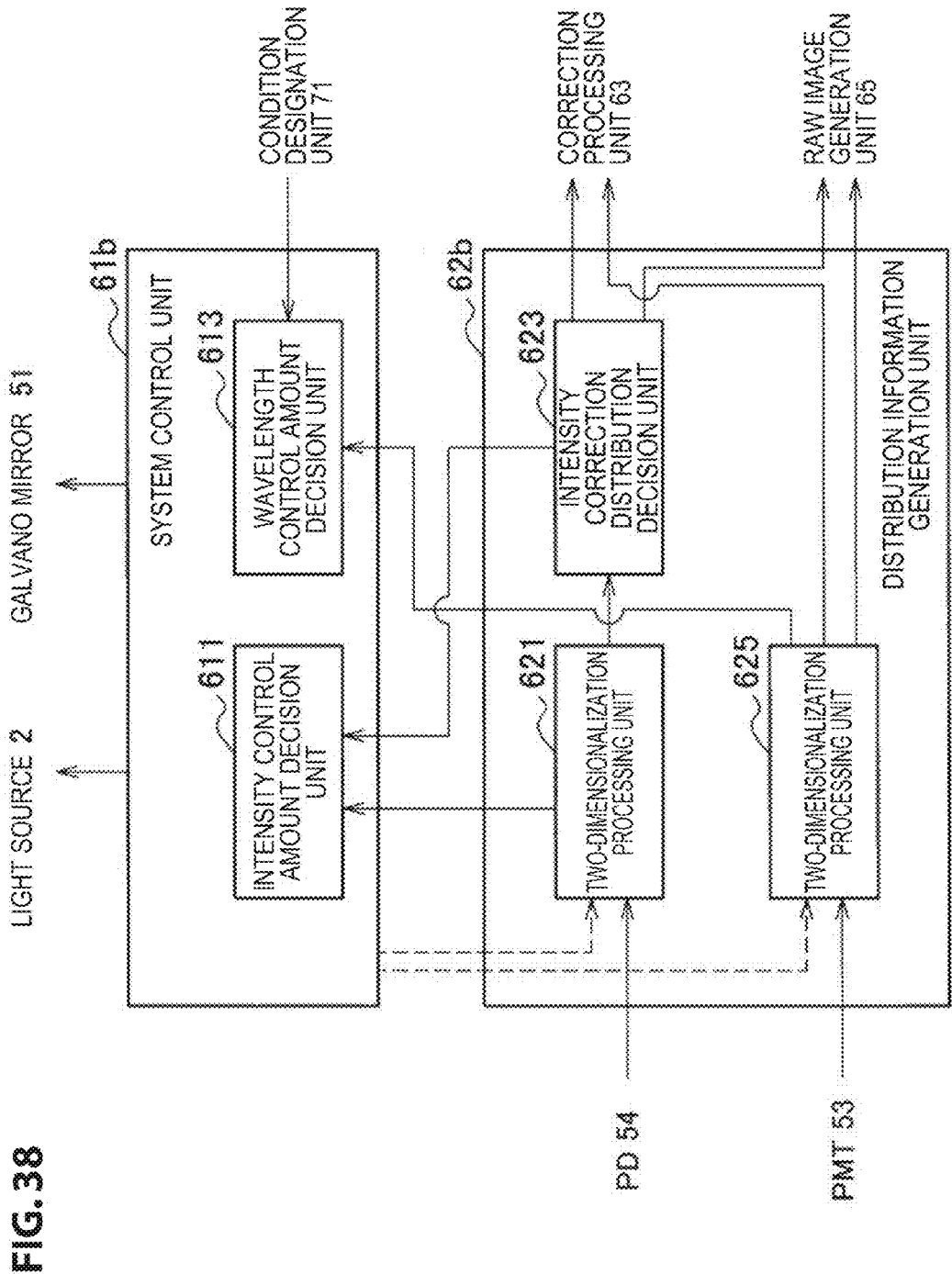
FIG. 38 is an illustrative diagram for describing a detailed functional configuration of a distribution information generation unit and a system control unit according to the embodiment.

Herein, the configurations of the system control unit 61*b* and the distribution information generation unit 62*b* will be described in detail with reference to FIG. 38. As shown in FIG. 38, the distribution information generation unit 62*b* includes the two-dimensionalization processing unit 621, the intensity correction distribution decision unit 623, and the two-dimensionalization processing unit 625. In addition, the system control unit 61*b* includes the intensity control amount decision unit 611 and the wavelength control amount decision unit 613.

Note that operations of the two-dimensionalization processing unit 621, the intensity correction distribution decision unit 623, and the intensity control amount decision unit 611 and an operation of the system control unit 61*b* based on an operation of the intensity control amount decision unit 611 are the same as those of the image acquisition device 1 according to the first embodiment described above (refer to FIG. 16).

In other words, the intensity control amount decision unit 611 acquires an intensity distribution of the idler light from the two-dimensionalization processing unit 621, is informed of a maximum gap of correction amounts from the intensity correction distribution decision unit 623, and then monitors a state of the light source 2 (particularly, a change in an intensity of excitation light) based on the acquired intensity distribution of the idler light and the maximum gap of the correction amounts. In addition, the intensity control amount decision unit 611 generates control information for controlling an intensity of laser light (pump light) emitted from the light source 2 based on the monitoring result. Then, the system control unit 61*b* may control the intensity of the laser light (pump light) emitted from the light source 2 based on the control information generated by the intensity control amount decision unit 611.

In addition, operations of the two-dimensionalization processing unit 625, the wavelength control amount decision unit 613, and the system control unit 61*b* based on an operation of the wavelength control amount decision unit 613 are the same as those of the image acquisition device 1*a* according to the second embodiment described above (refer to FIG. 29).

That is, the wavelength control amount decision unit 613 acquires the generated intensity distribution of the fluorescence from the two-dimensionalization processing unit 625, and decides a control amount of the wavelength (frequency) of the laser light (excitation light) emitted from the light source 2 so as to improve contrast of the intensity distribution of the fluorescence. When the control amount of the wavelength of the laser light is decided by the wavelength control amount decision unit 613, the system control unit 61*b* controls the wavelength of the laser light emitted from the light source 2 based on the control amount by controlling the light source 2.

When the wavelength of the laser light emitted from the light source 2 is controlled, the two-dimensionalization processing unit 625 acquires the intensity distribution of the fluorescence that is based on the laser light after the control, and outputs the acquired intensity distribution of the fluorescence to the wavelength control amount decision unit 613. The wavelength control amount decision unit 613 evaluates the intensity distribution of the fluorescence that has been acquired again, and then computes a control amount of the wavelength of the laser light so as to improve contrast of the intensity distribution of the fluorescence.

By repeating the above operation, the wavelength of the laser light emitted from the light source 2 is controlled by the system control unit 61*b* and the wavelength control amount decision unit 613 so that the contrast of the intensity distribution of the fluorescence has the maximum value.

In addition, an operation of the raw image generation unit 65 according to the present embodiment is the same as that of the raw image generation unit 65 according to the first and the second embodiments described above. In other words, the raw image generation unit 65 acquires the intensity distribution of the fluorescence from the two-dimensionalization processing unit 625, and generates a raw file by forming the intensity distribution of the fluorescence in a predetermined file format as image data (raw image). In addition, the raw image generation unit 65 may acquire information relating to the intensity distribution of the fluorescence from the system control unit 61*b* to associate the acquired information with the generated raw file as relevant information. Note that it is needless to say that the relevant information associated with the raw file can include, for example, the relevant information shown in the first embodiment (refer to FIG. 19) or the relevant information shown in the second embodiment (refer to FIG. 31).

Hereinabove, the configuration of the image acquisition device 1*b* according to the present embodiment has been described with reference to FIGS. 37 and 38.

3.3. Conclusion

As described above, the combination of the image acquisition device 1 according to the first embodiment and the image acquisition device 1*a* according to the second embodiment can be operated as the image acquisition device 1*b* according to the present embodiment. Note that it is needless to say that the image acquisition device 1*b* according to the present embodiment likewise exhibits effects of both of the image acquisition device 1 according to the first embodiment and the image acquisition device 1*a* according to the second embodiment.

4. Fourth Embodiment

4.1. Overview of an Image Acquisition Device

Figure 39:
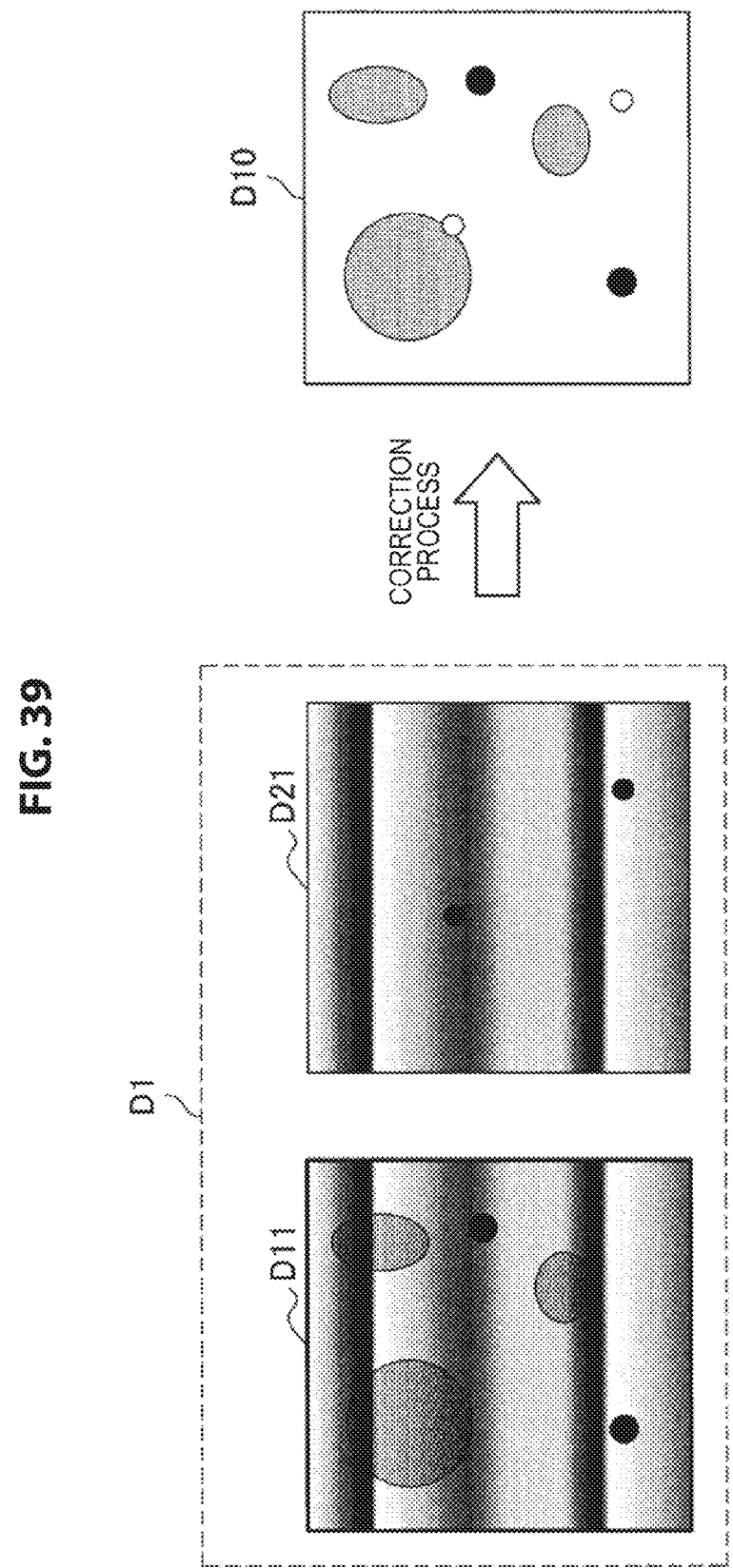
FIG. 39 is an illustrative diagram for describing an overview of an image acquisition device according to a fourth embodiment of the present disclosure.
Figure 40:
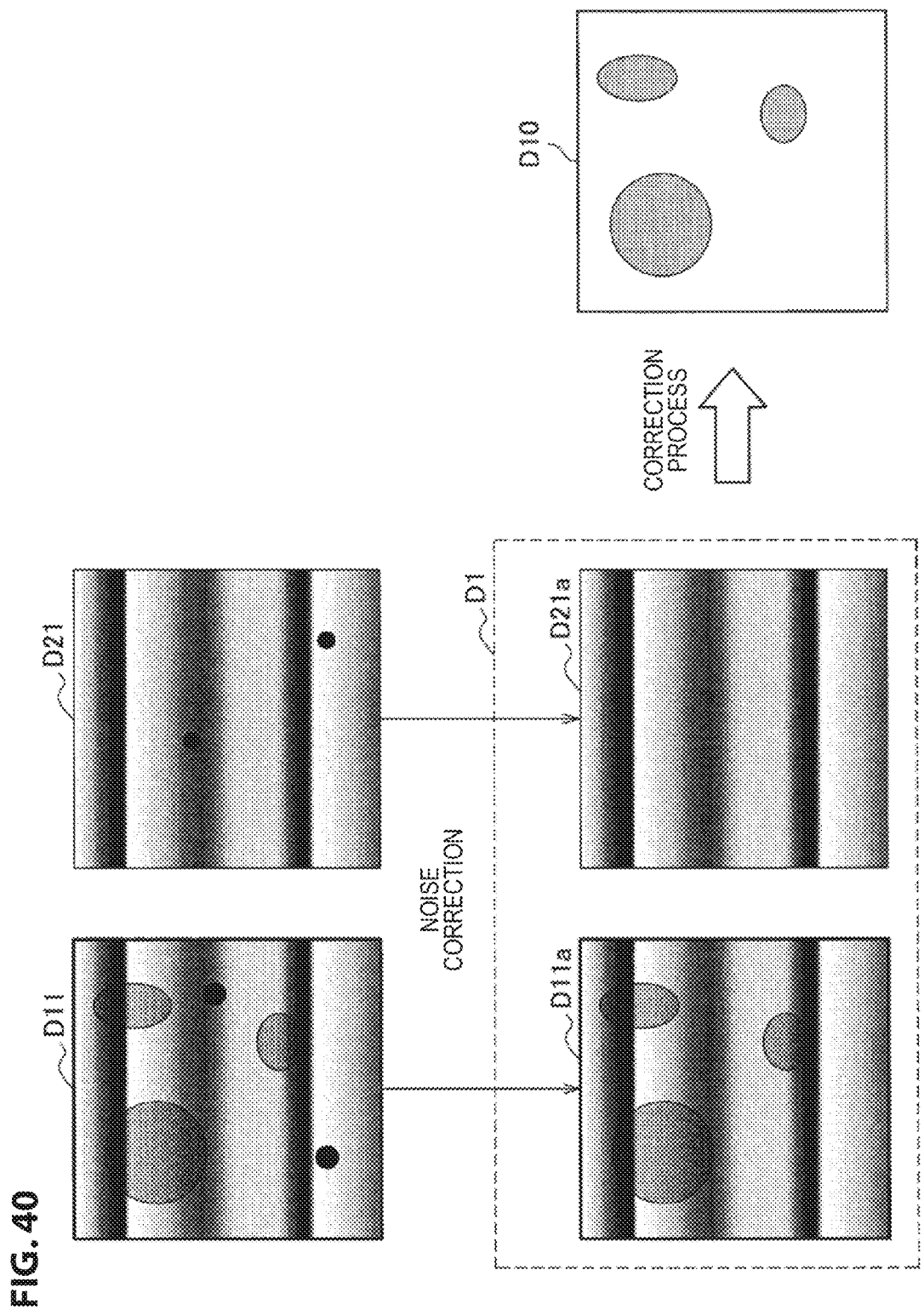
FIG. 40 is an illustrative diagram for describing the principle of a correction process according to the embodiment.

Next, an image acquisition device according to a fourth embodiment will be described. First, a problem of the image acquisition device according to the present embodiment will be summarized with reference to FIGS. 39 and 40. FIG. 39 is an illustrative diagram for describing an overview of the image acquisition device according to the present embodiment. In addition, FIG. 40 is an illustrative diagram for describing the principle of a correction process according to the present embodiment. Note that the image acquisition device according to the present embodiment may be referred to hereinafter as an "image acquisition device 1*c*" in order to be distinguished from the image acquisition devices according to other embodiments.

The image acquisition device 1 according to the first embodiment and the image acquisition device 1*b* according to the third embodiment described above generate correction data based on the intensity distribution of idler light and correct noise appearing on the intensity distribution of fluorescence which is accompanied by a change in the intensity of laser light based on the generated correction data.

Meanwhile, because intensities of fluorescence and idler light are separately detected, there are cases in which noise that is independent of a change in the intensity of laser light occurs separately in the generated intensity distribution of the fluorescence and intensity distribution of the idler light. For example, FIG. 39 schematically shows states of each of the generated intensity distribution of the fluorescence D11 and intensity distribution of the idler light D21 in which different types of noise occur.

In the example shown in FIG. 39, when the intensity distribution of the fluorescence D11 is corrected based on the intensity distribution of the idler light D21, the noise occurring in the intensity distribution of the idler light D21 is superimposed on the noise occurring in the intensity distribution of the fluorescence D11 before correction in a correction-processed intensity distribution of the fluorescence D10. In other words, in the example shown in FIG. 39, while noise that is accompanied by the change in the intensity of the laser light is corrected through the correction process, the noise occurring in each of the intensity distribution of the fluorescence D11 and the intensity distribution of the idler light D21 is not reduced and appears in the correction-processed intensity distribution of the fluorescence D10.

Thus, in the image acquisition device 1c according to the present embodiment, a noise correction process is performed in each of the generated intensity distribution of the fluorescence D11 and intensity distribution of the idler light D21 as shown in FIG. 40. Accordingly, the image acquisition device 1c corrects noise that appears in the intensity distribution of the fluorescence D11 and intensity distribution of the idler light D21 and is independent of the change in the intensity of the laser light, thereby generating noise-corrected intensity distribution of the fluorescence D11a and intensity distribution of the idler light D21a.

Then, the image acquisition device 1c corrects the noise that appears in the intensity distribution of the fluorescence D11a and is accompanied by the change in the intensity of the laser light by correcting the intensity distribution of the fluorescence D11a based on the intensity distribution of the idler light D21a, thereby generating the correction-processed intensity distribution of the fluorescence D10. With this configuration, the image acquisition device 1c can suppress appearance of the noise that occurs in each of the intensity distribution of the fluorescence D11 and the intensity distribution of the idler light D21 and is independent of the change in the intensity of the laser light.

In addition, the image acquisition device 1c according to the present embodiment generates the raw file D1 based on the noise-corrected intensity distribution of the fluorescence D11a and intensity distribution of the idler light D21a. Accordingly, even when an external device such as the information processing device 800 likewise generates the correction-processed intensity distribution of the fluorescence D10, the device can suppress appearance of noise that is independent of a change in the intensity of the laser light. Hereinbelow, details of the image acquisition device 1c according to the present embodiment will be described.

4.2. Configuration of the Image Acquisition Device

Figure 41:
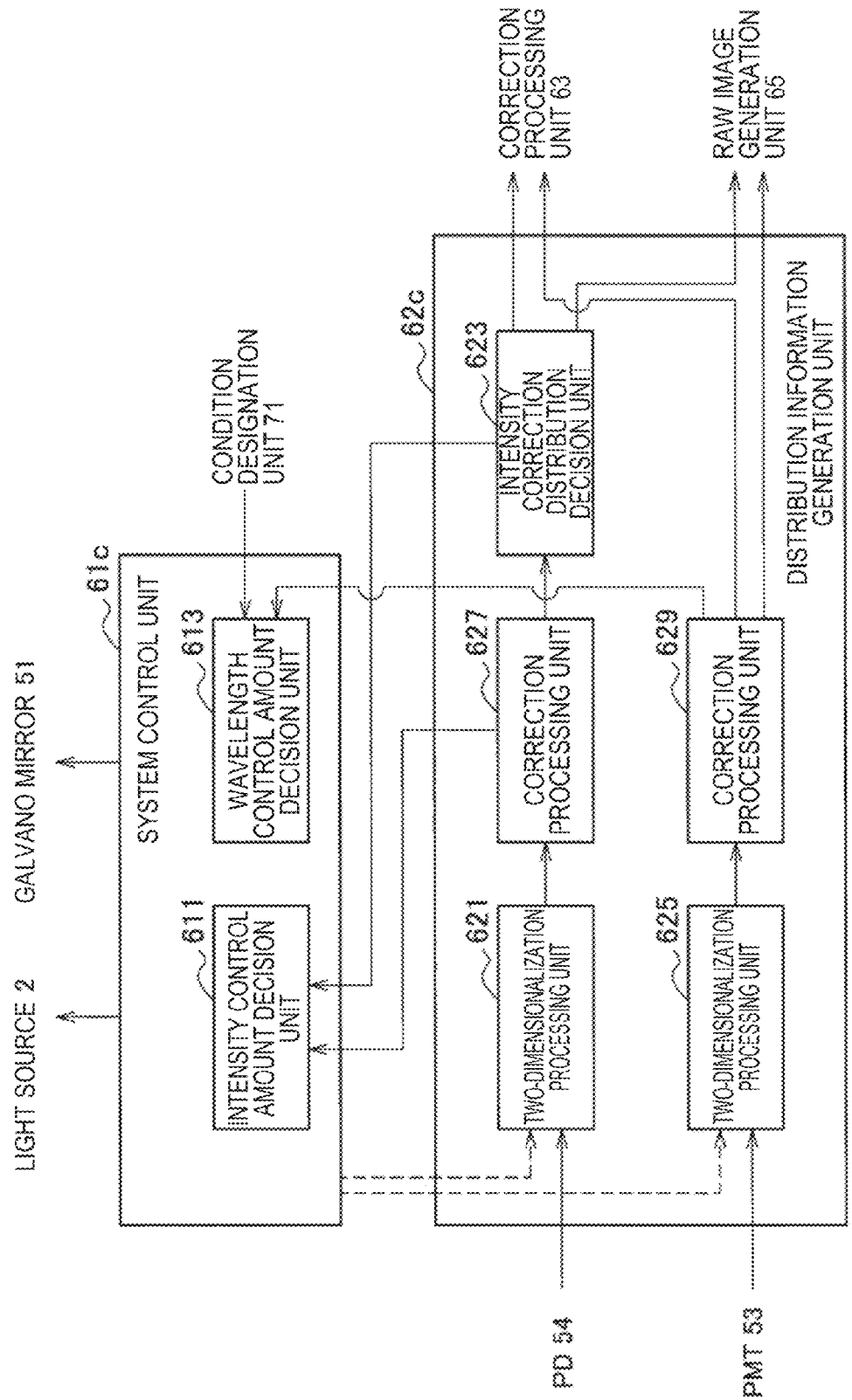
FIG. 41 is an illustrative diagram for describing a detailed functional configuration of a distribution information generation unit and a system control unit according to the embodiment.

The image acquisition device according to the present embodiment has the distribution information generation unit 62c which corresponds to the distribution information generation unit 62b of the image acquisition device 1b according to the third embodiment described above but has a different configuration from that of the image acquisition device 1b, and other configurations are basically the same as those of the image acquisition device 1b. For this reason, description will be provided hereinbelow focusing on the configuration of the distribution information generation unit 62c according to the present embodiment with reference to FIG. 41. FIG. 41 is an illustrative diagram for describing a detailed functional configuration of the distribution information generation unit 62c and the system control unit 61c according to the present embodiment.

As shown in FIG. 41, the distribution information generation unit 62c according to the present embodiment is different from the distribution information generation unit 62b according to the third embodiment described above (refer to FIG. 38) in that the former includes a correction processing unit 627 and another correction processing unit 629.

In the distribution information generation unit 62c according to the present embodiment, the two-dimensionalization processing unit 621 outputs a generated intensity distribution of idler light to the correction processing unit 627.

The correction processing unit 627 acquires the intensity distribution of the idler light from the two-dimensionalization processing unit 621, and performs a correction process on the acquired intensity distribution of the idler light for noise that is independent of a change in the intensity of laser light. At this time, the correction processing unit 627 applies filters in units of pixels for the acquired intensity distribution of the idler light.

As an example of the filters in units of pixels, for example, a median filter is exemplified. In this case, the correction processing unit 627 uses each pixel in the intensity distribution of the idler light as, for example, a reference pixel and the pixel value of the reference pixel as a threshold value, and then performs threshold processing on other peripheral pixels (for example, 8 peripheral pixels). Then, the correction processing unit 627 smoothes pixel values of the reference pixel and the other peripheral pixels.

Note that, when the correction processing unit 627 smoothes the pixel values of the reference pixel and the other peripheral pixels, a simple average may be used, or the pixel values may be smoothed according to predetermined statistics.

In addition, the correction processing unit 627 may have anisotropy on the threshold processing with respect to the other peripheral pixels or the process relating to smoothing of the pixel values of the reference pixel and the other peripheral pixels. As a specific example, the correction processing unit 627 may control a parameter of a noise removal process (for example, a threshold value) so that the noise removal process is performed more intensively in the lateral direction than in the longitudinal direction.

The correction processing unit 627 outputs the intensity distribution of the idler light that has undergone the noise removal process to the intensity correction distribution decision unit 623 and the intensity control amount decision unit 611. Note that processes performed thereafter, in other words, operations of the intensity correction distribution decision unit 623 and the intensity control amount decision unit 611, are the same as those in the image acquisition devices according to the first and the third embodiments described above except that the former targets the intensity distribution of the idler light that has undergone the noise removal process.

In addition, in the distribution information generation unit 62c according to the present embodiment, the two-dimensionalization processing unit 625 outputs generated intensity distribution of fluorescence to the correction processing unit 629.

The correction processing unit 629 acquires the intensity distribution of the fluorescence from the two-dimensionalization processing unit 625, and performs a correction process on the acquired intensity distribution of the fluorescence for noise that does not depend on fluctuation of the intensity of laser light. At this time, the correction processing unit 629 applies filters in units of frequencies (i.e., frequency filters) to the acquired intensity distribution of the fluorescence.

Specifically, the correction processing unit 629 sets a predetermined frequency as a threshold value, regards a signal having a frequency higher than the threshold value as noise, and then removes the noise (in other words, removes a high frequency component). In this manner, the correction processing units 627 and 629 perform different kinds of noise removal processes on the intensity distributions that the respective units have acquired.

The correction processing unit 629 outputs the intensity distribution of the fluorescence that has undergone the noise removal process to the wavelength control amount decision unit 613, the correction processing unit 63, and the raw image generation unit 65. Note that processes performed thereafter, i.e., operations of the wavelength control amount decision unit 613, the correction processing unit 63, and the raw image generation unit 65, are the same as those of the image acquisition devices according to the second and the third embodiments described above except that the former targets the intensity distribution of the fluorescence that has undergone the noise removal process.

In addition, it is needless to say that the raw image generation unit 65 according to the present embodiment generates a raw file using the noise-removed intensity distribution of the fluorescence as image data and associates the raw file with the noise-removed intensity distribution of the idler light as relevant information.

Hereinabove, the configuration of the image acquisition device 1c according to the present embodiment has been described with reference to FIG. 41 particularly focusing on the operation of the distribution information generation unit 62c. Note that it is not necessary to provide both of the correction processing units 627 and 629 and any one of them may be provided.

4.3. File Format of a Raw File

Figure 42:
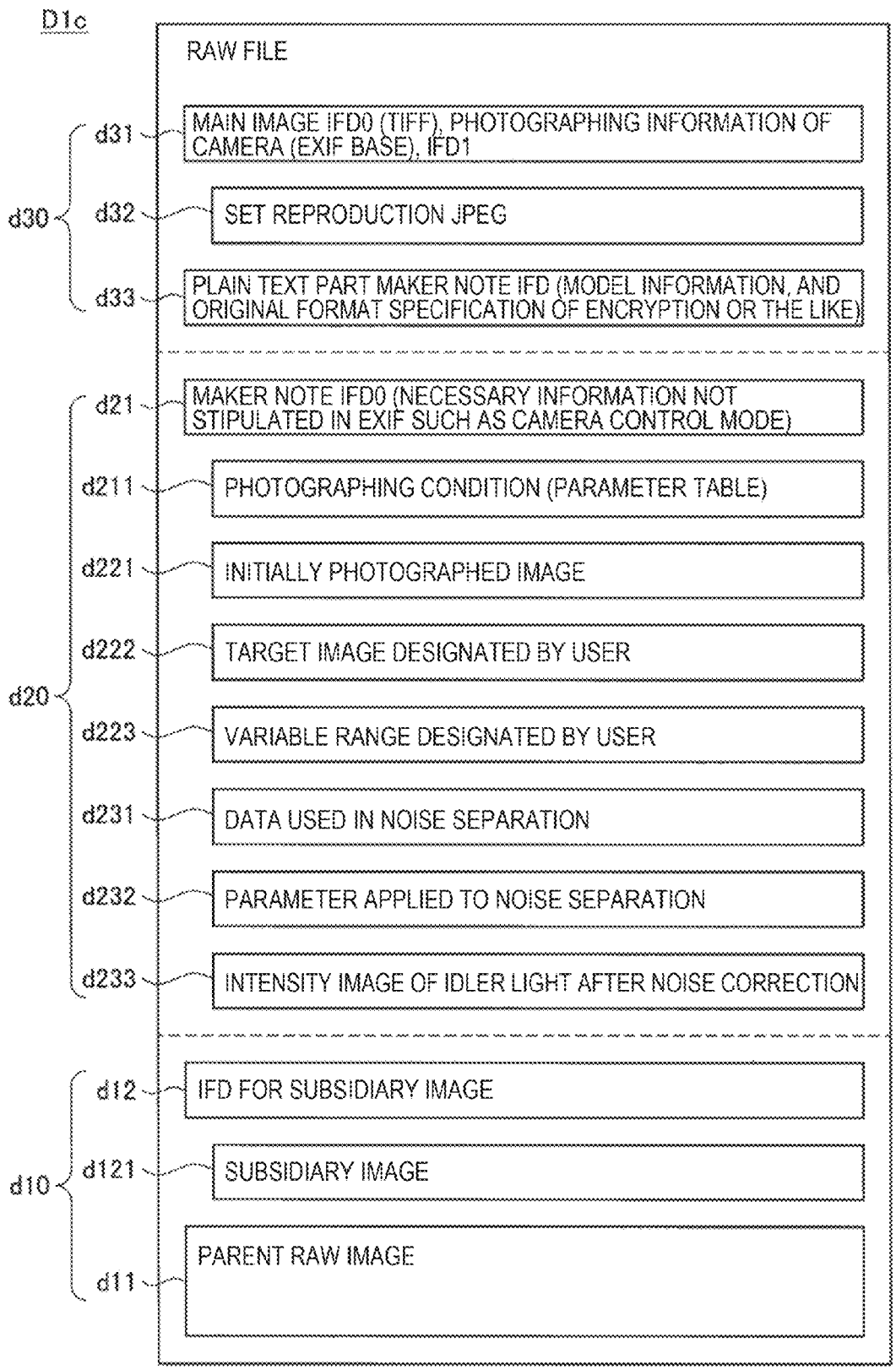
FIG. 42 is a diagram showing an example of a file format of a raw file according to the embodiment.

Next, an example of a file format of the raw file D1c according to the present embodiment will be described with reference to FIG. 42. FIG. 42 is a diagram showing the example of the file format of the raw file D1c according to the present embodiment.

As shown in FIG. 42, the raw file D1c according to the present embodiment includes, for example, the data area d10, the basic control information area d30, and an extended area d20c. Note that, since configurations of the data area d10 and the basic control information area d30 are the same as those of the raw file D1 according to the first embodiment (refer to FIG. 19), detailed description thereof will be omitted.

The extended area d20c includes a maker note IFD d21 as shown in FIG. 42. The maker note IFD d21 is an IFD for storing information such as a camera control mode that is not stipulated in the EXIF, and also storing photographing information and control information intrinsic to the image acquisition device 1.

In addition, the maker note IFD d21 according to the present embodiment includes, for example, the photographing condition d211, the initially photographed image d221, the target image designated by a user d222, the variable range designated by a user d223, data used in noise separation d231, a parameter applied to noise separation d232, and a noise-corrected intensity image of idler light d233. Note that the photographing condition d211, the initially photographed image d221, the target image designated by a user d222, and the variable range designated by a user d223 are the same as those in the raw file D1a according to the second embodiment described above (refer to FIG. 31).

The noise-corrected intensity image of idler light d233 represents the intensity distribution of the idler light D21a for which the correction processing unit 627 has performed the noise removal process. Note that, instead of the intensity distribution of the idler light D21a, correction data computed based on the intensity distribution of the idler light D21a may be recorded in the raw file D1c as the noise-corrected intensity image of idler light d233.

The data used in noise separation d231 represents data of the frequency filter applied to the intensity distribution of the fluorescence D11 for noise removal. Note that a form of the data used in noise separation d231 is not particularly limited as long as the content of the noise removal process performed on the intensity distribution of the fluorescence D11 can be specified. As a specific example, the data used in noise separation d231 may be a histogram that indicates a characteristic of the frequency filter (frequency characteristic).

By recording the data used in noise separation d231 in the raw file D1c as above, an external device (for example, the information processing device 800) that has read the raw file D1c can correct noise on the parent raw image d11 like the image acquisition device 1c according to the present embodiment.

The parameter applied to noise separation d232 is a parameter indicating the type and the content of the noise removal process (for example, information indicating an applied filter or a parameter thereof) that has been performed on the correction data based on the intensity distribution of the idler light D21. Note that a form of the parameter applied to noise separation d232 is not particularly limited as long as the type and the content of the noise removal process performed on the correction data can be specified.

By recording the parameter applied to noise separation d232 in the raw file D1c as above, an external device (for example, the information processing device 800) that has read the raw file D1c can specify the content of the noise removal process performed on the noise-corrected intensity image of the idler light.

Hereinabove, the file format of the raw file D1c according to the present embodiment has been described with reference to FIG. 42. Note that the file format of the raw file D1c shown above is merely an example, and it is needless to say that all kinds of information may not necessarily be included therein.

4.4. Conclusion

As described above, the image acquisition device 1c according to the present embodiment performs the respective noise removal processes on the intensity distribution of the fluorescence D11 and the intensity distribution of the idler light D21 and thereby generates the noise-corrected intensity distribution of the fluorescence D11a and intensity distribution of the idler light D21a. Then, the image acquisition device 1c corrects the noise that appears in the intensity distribution of the fluorescence D11a and is accompanied by the change in the intensity of the laser light by correcting the intensity distribution of the fluorescence D11a based on the intensity distribution of the idler light D21a, thereby generating the correction-processed intensity distribution of the fluorescence D10. With this configuration, the image acquisition device 1c according to the present embodiment can suppress appearance of the noise that occurs in each of the intensity distribution of the fluorescence D11 and the intensity distribution of the idler light D21 and is independent of the change in the intensity of the laser light.

In addition, the image acquisition device 1c according to the present embodiment generates the raw file D1c based on the noise-corrected intensity distribution of the fluorescence D11a and intensity distribution of the idler light D21a. Accordingly, even when an external device such as the information processing device 800 likewise generates the correction-processed intensity distribution of the fluorescence D10, the device can suppress appearance of noise that is independent of a change in the intensity of the laser light.

5. Hardware Configuration

Figure 43:
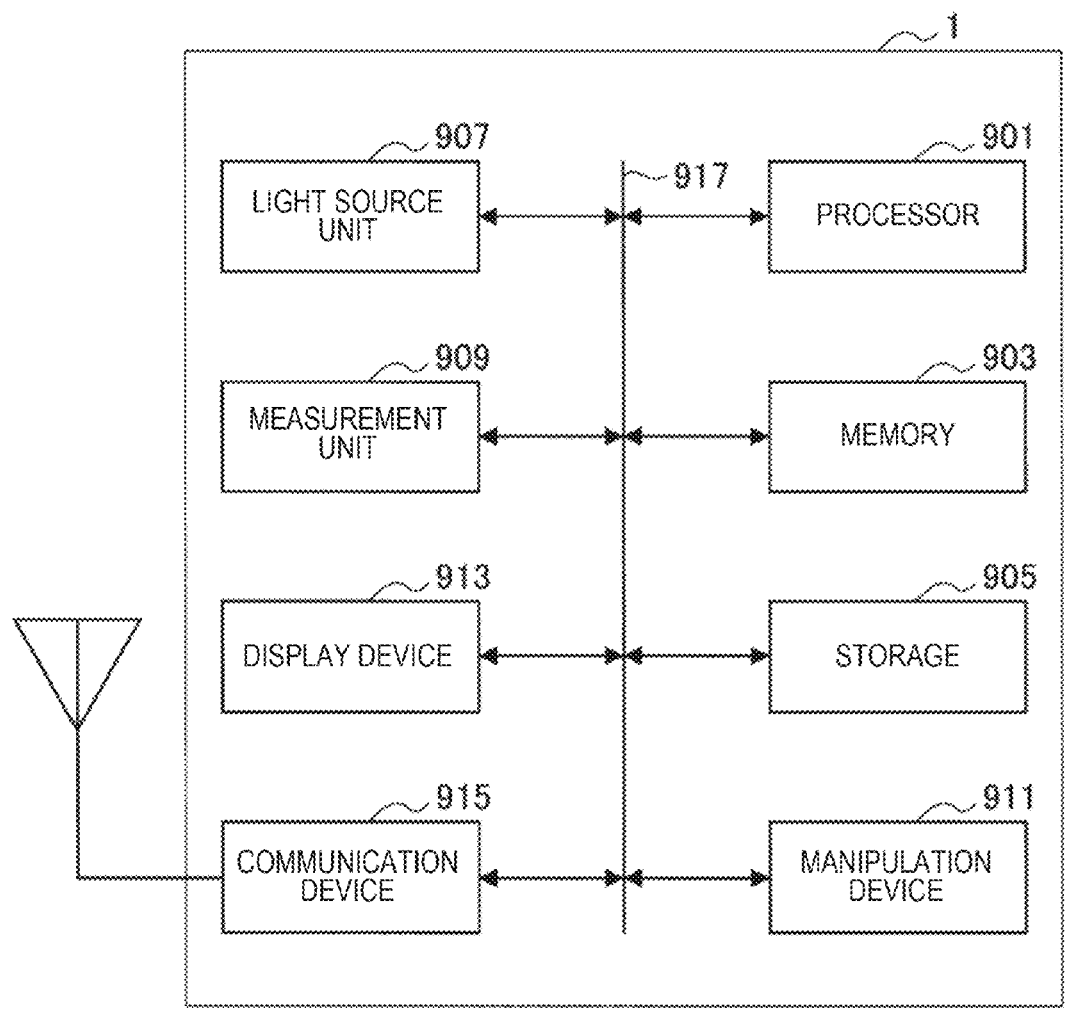
FIG. 43 is an example of a hardware configuration of the image acquisition device.

Next, an example of a hardware configuration of the image acquisition device 1 according to the embodiment will be described with reference to FIG. 43. FIG. 43 is a diagram showing an example of the hardware configuration of the image acquisition device 1 according to the embodiment.

As shown in FIG. 43, the image acquisition device 1 according to the present embodiment includes a processor 901, a memory 903, a storage 905, a light source unit 907, a measurement unit 909, a manipulation device 911, a display device 913, a communication device 915, and a bus 917.

The processor 901 may be, for example, a central processing unit (CPU), a graphics processing unit (GPU), a digital signal processor (DSP), or a system-on-chip (SoC), and executes various kinds of processing of the image acquisition device 1. The processor 901 can be configured by, for example, an electronic circuit for executing various kinds of arithmetic operations. Note that each of the constituent elements included in the control unit 6 described above can be configured by the processor 901.

The memory 903 includes a random access memory (RAM) and a read only memory (ROM), and stores programs executed by the processor 901 and data. The storage 905 can include a storage medium such as a semiconductor memory or a hard disk. Note that the storage unit 66 described above can be configured by, for example, the memory 903 or the storage 905.

The light source unit 907 is a unit for radiating excitation light onto the sample S, and corresponds to the light source 2 described above. The intensity and wavelength of the excitation light emitted from light source unit 907 are controlled by the processor 901.

The measurement unit 909 is a unit that guides the excitation light emitted from the light source unit 907 to the sample S and detects fluorescence generated from the sample S, and corresponds to the measurement unit 3 described above. The measurement unit 909 controls the optical path of the light emitted from the light source unit 907 to scan the top of the sample S using the light according to control of the processor 901.

The manipulation device 911 has the function of generating input signals for enabling a user to perform desired manipulations. The manipulation device 911 may be configured using an input unit, for example, buttons and switches for enabling the user to input information, an input control circuit that generates input signals based on inputs from the user and supplies the signals to the processor 901, and the like. Note that the condition designation unit 71 described above can be configured by the manipulation device 911.

The display device 913 is an example of an output device, and may be a display device such as a liquid crystal display (LCD) device, or an organic light emitting diode (OLED) display device. The display device 913 can provide information to the user by displaying screens. Note that the display unit 72 described above can be configured by the display device 913.

The communication device 915 is a communication section included in the image acquisition device 1, communicating with an external device such as the information processing device 800 through a network. The communication device 915 is an interface for wireless communication, and may include a communication antenna, a radio frequency (RF) circuit, a baseband processor, and the like.

The communication device 915 has the function of performing various kinds of signal processing on signals received from the external device, and can supply digital signals generated from received analog signals to the processor 901. Note that the communication unit 73 described above can be configured by the communication device 915.

The bus 917 connects the processor 901, the memory 903, the storage 905, the light source unit 907, the measurement unit 909, the manipulation device 911, the display device 913, and the communication device 915 to one another. The bus 917 may include a plurality of kinds of buses.

In addition, a program for causing the hardware including the CPU, the ROM, the RAM, and the like in a computer to exhibit the same function as the configuration of the image acquisition device 1 described above can also be created. In addition, a computer-readable storage medium in which the program is recorded can also be provided.

6. Conclusion

So far, the exemplary embodiments of the present disclosure have been described in detail with reference to the accompanying drawings, however, a technical scope of the present disclosure is not limited thereto. It should be understood by those skilled in the art that various modifications, combinations, sub-combinations and alterations may occur depending on design requirements and other factors insofar as they are within the scope of the appended claims or the equivalents thereof.

In addition, the effects described in the present specification are merely illustrative or demonstrative, and not limitative. In other words, the technology according to the present disclosure can exhibit other effects that are evident to those skilled in the art based on the present specification along with or instead of the effects.

Additionally, the present technology may also be configured as below.

(1) An image acquisition device including:
a light source configured to emit laser light and to be capable of controlling a wavelength of the laser light;
a measurement unit configured to scan a sample using the laser light and to measure an intensity of measurement target light from the sample by receiving the laser light; and
a control unit configured to generate an image of the sample based on intensity distribution of the measured measurement target light,
wherein the control unit controls a wavelength of the laser light based on the intensity distribution of the measured measurement target light.

(2) The image acquisition device according to (1),
wherein the light source emits laser light having a first wavelength and laser light having a second wavelength that is different from the first wavelength in a switching manner,
wherein the measurement unit scans the sample using each of the laser light having the first wavelength and the laser light having the second wavelength, and measures a first intensity of the measurement target light that is based on the laser light having the first wavelength and a second intensity of the measurement target light that is based on the laser light having the second wavelength, and wherein the control unit controls at least one of the first wavelength and the second wavelength based on the intensity distribution of the first intensity and the intensity distribution of the second intensity.

(3) The image acquisition device according to (2),
wherein, when fluorescence relative efficiencies of a first fluorochrome and a second fluorochrome which are included in the sample and different from each other at the first wavelength are set to $E(\lambda 1, F1)$ and $E(\lambda 1, F2)$ respectively, and fluorescence relative efficiencies of the first fluorochrome and the second fluorochrome at the second wavelength are set to $E(\lambda 2, F1)$ and $E(\lambda 2, F2)$ respectively, the control unit decides the first wavelength and the second wavelength before control so that the formula expressed by formula 12 shown below has a maximum value.

$$|E(\lambda 1,F1)-E(\lambda 1,F2)|+|E(\lambda 2,F1)-E(\lambda 2,F2)| \quad \text{Formula 12}$$

(4) The image acquisition device according to (2) or (3),
wherein the measurement unit measures an intensity of the measurement target light that is based on the laser light having the wavelengths at each of a wavelength that is higher than one of the wavelengths and a wavelength that is lower than the wavelength,
wherein the control unit computes contrast of each of the intensity distribution of the measurement target light that is based on the laser light having the high wavelength and the intensity distribution of the measurement target light that is based on the laser light having the low wavelength and compares the contrast, and thereby controls the one wavelength to be one of the high wavelength and the low wavelength corresponding to the intensity distribution in which the computed contrast is high based on the comparison result.

(5) The image acquisition device according to (4), wherein, by repeating the control of the one wavelength and the comparison of the contrast of the intensity distributions of the measurement target light that are based on the laser light having the high wavelength and the laser light having the low wavelength using the one wavelength after the control as a reference, the control unit controls the one wavelength so that contrast of the intensity distribution of the measurement target light has a maximum value.

(6) The image acquisition device according to (5), wherein the control unit controls one of the first wavelength and the second wavelength and fixes the other wavelength so that the contrast of the intensity distribution of the measurement target light has the maximum value, and then fixes the controlled one wavelength and controls the other wavelength so that the contrast of the intensity distribution of the measurement target light has the maximum value.

(7) The image acquisition device according to any one of (2) to (6),
wherein the measurement unit changes each of the first wavelength and the second wavelength by a predetermined wavelength and then measures intensities of the measurement target light that are based on the laser light having each of the first wavelength and the second wavelength at each of the wavelengths before the change and after the change, and
wherein the control unit computes contrast of each of the intensity distribution of the measurement target light before the change and the intensity distribution of the measurement target light after the change at each of the first wavelength and the second wavelength and then compares the contrast, and thereby sets one of the first wavelength and the second wavelength at which the difference between the computed contrast before the change and after the change is great as the one wavelength based on the comparison result.

(8) The image acquisition device according to any one of (4) to (7),
wherein, when first coordinates that indicate a pixel having a highest luminance in a first image that is based on the intensity distribution of the measurement target light measured based on the laser light having the first wavelength are set to (x1, y1), second coordinates that indicate a pixel having a highest luminance in a second image that is based on the intensity distribution of the measurement target light measured based on the laser light having the second wavelength are set to (x2, y2), the luminance of the first coordinates and the luminance of the second coordinates in the first image are respectively set to $L(\lambda 1, x1, y1)$ and $L(\lambda 1, x2, y2)$, and the luminance of the first coordinates and the luminance of the second coordinates in the second image are respectively set to $L(\lambda 2, x1, y1)$ and $L(\lambda 2, x2, y2)$, the control unit decides the contrast $C(\lambda 1, \lambda 2)$ based on formula 13 shown below.

$$C(\lambda 1,\lambda 2)=|L(\lambda 1,x1,y1)-L(\lambda 2,x1,y1)|-|L(\lambda 1,x2,y2)-L(\lambda 2,x2,y2)| \quad \text{Formula 13}$$

(9) The image acquisition device according to (1),
wherein the measurement unit sets one of wavelengths of the emittable laser light as a reference wavelength, and at each of a wavelength that is higher than the reference wavelength and a wavelength that is lower than the reference wavelength, measures an intensity of the measurement target light that is based on laser light having the wavelength, and
wherein the control unit computes contrast of each of the intensity distribution of the measurement target light that is based on the laser light having the high wavelength and the intensity distribution of the measurement target light that is based on the laser light having the low wavelength and compares the contrast, and then controls the wavelength of the laser light to be one of the high wavelength and the low wavelength corresponding to the intensity distribution in which the computed contrast is high from the reference wavelength based on the comparison result.

(10) The image acquisition device according to (9), wherein, by repeating the control of the wavelength of the laser light and the comparison of the contrast of the intensity distributions of the measurement target light that are based on the laser light having the high wavelength and the laser light having the low wavelength using the wavelength after the control as the reference wavelength, the control unit controls the wavelength of the laser light so that contrast of the intensity distribution of the measurement target light has a maximum value.

(11) The image acquisition device according to any one of (1) to (11), wherein the light source is configured to include a laser unit that outputs pump light having a predetermined frequency and an optical parametric oscillator and to be capable of controlling a wavelength of the laser light by controlling an oscillation condition of the optical parametric oscillator.

(12) The image acquisition device according to any one of (1) to (11), wherein the light source and the measurement unit are provided in the same housing.

(13) The image acquisition device according to any one of (1) to (12),
wherein the measurement unit measures an intensity of laser light emitted from the light source, and
wherein the control unit executes at least one of control of the intensity of the laser light emitted from the light source and correction of intensity distribution of the measured measurement target light based on the measured intensity of the laser light.

(14) An image acquisition method including:
scanning a sample using laser light emitted from a light source configured to be capable of controlling a wavelength of the laser light and measuring an intensity of measurement target light generated from the sample by receiving the laser light;
generating an image of the sample based on intensity distribution of the measured measurement target light; and
controlling a wavelength of the laser light based on the intensity distribution of the measured measurement target light.

What is claimed is:

1. An image acquisition device comprising:
a light source configured to emit laser light and to be capable of controlling a wavelength of the laser light, wherein the light source emits laser light having a first wavelength and laser light having a second wavelength that is different from the first wavelength in a switching manner;
a measurement unit configured to scan a sample using the laser light and to measure an intensity of measurement target light from the sample by receiving the laser light, wherein the measurement unit scans the sample using each of the laser light having the first wavelength and the laser light having the second wavelength and measures a first intensity of the measurement target light that is based on the laser light having the first wavelength and a second intensity of the measurement target light that is based on the laser light having the second wavelength; and
a control unit configured to generate an image of the sample based on intensity distribution of the measured measurement target light,
wherein the control unit controls a wavelength of the laser light based on the intensity distribution of the measured measurement target light and controls at least one of the first wavelength and the second wavelength based on the intensity distribution of the first intensity and the intensity distribution of the second intensity,
wherein the measurement unit measures an intensity of the measurement target light that is based on the laser light having the wavelengths at each of a wavelength that is higher than one of the wavelengths and a wavelength that is lower than the wavelength, and
wherein the control unit computes contrast of each of the intensity distribution of the measurement target light that is based on the laser light having the high wavelength and the intensity distribution of the measurement target light that is based on the laser light having the low wavelength and compares the contrast, and thereby controls the one wavelength to be one of the high wavelength and the low wavelength corresponding to the intensity distribution in which the computed contrast is high based on the comparison result.

2. The image acquisition device according to claim 1, wherein, when fluorescence relative efficiencies of a first fluorochrome and a second fluorochrome which are included in the sample and different from each other at the first wavelength are set to $E(\lambda 1, F1)$ and $E(\lambda 1, F2)$ respectively, and fluorescence relative efficiencies of the first fluorochrome and the second fluorochrome at the second wavelength are set to $E(\lambda 2, F1)$ and $E(\lambda 2, F2)$ respectively, the control unit decides the first wavelength and the second wavelength before control so that the formula expressed by formula 12 shown below has a maximum value $$|E(\lambda 1, F1) - E(\lambda 1, F2)| + |E(\lambda 2, F1) - (\lambda 2, F2)|. \quad \text{Formula 12}$$

3. The image acquisition device according to claim 1, wherein, by repeating the control of the one wavelength and the comparison of the contrast of the intensity distributions of the measurement target light that are based on the laser light having the high wavelength and the laser light having the low wavelength using the one wavelength after the control as a reference, the control unit controls the one wavelength so that contrast of the intensity distribution of the measurement target light has a maximum value.

4. The image acquisition device according to claim 3, wherein the control unit controls one of the first wavelength and the second wavelength and fixes the other wavelength so that the contrast of the intensity distribution of the measurement target light has the maximum value, and then fixes the controlled one wavelength and controls the other wavelength so that the contrast of the intensity distribution of the measurement target light has the maximum value.

5. The image acquisition device according to claim 1,
wherein the measurement unit changes each of the first wavelength and the second wavelength by a predetermined wavelength and then measures intensities of the measurement target light that are based on the laser light having each of the first wavelength and the second wavelength at each of the wavelengths before the change and after the change, and
wherein the control unit computes contrast of each of the intensity distribution of the measurement target light before the change and the intensity distribution of the measurement target light after the change at each of the first wavelength and the second wavelength and then compares the contrast, and thereby sets one of the first wavelength and the second wavelength at which the difference between the computed contrast before the change and after the change is great as the one wavelength based on the comparison result.

6. The image acquisition device according to claim 1,
wherein, when first coordinates that indicate a pixel having a highest luminance in a first image that is based on the intensity distribution of the measurement target light measured based on the laser light having the first wavelength are set to (x1, y1), second coordinates that indicate a pixel having a highest luminance in a second image that is based on the intensity distribution of the measurement target light measured based on the laser light having the second wavelength are set to (x2, y2), the luminance of the first coordinates and the luminance of the second coordinates in the first image are respectively set to $L(\lambda 1, x1, y1)$ and $L(\lambda 1, x2, y2)$, and the luminance of the first coordinates and the luminance of the second coordinates in the second image are respectively set to $L(\lambda 2, x1, y1)$ and $L(\lambda 2, x2, y2)$, the control unit decides the contrast $C(\lambda 1, \lambda 2)$ based on formula 13 shown below $$C(\lambda 1, \lambda 2) = |L(\lambda 1, x1, y1) - L(\lambda 2, x1, y1)| - |L(\lambda 1, x2, y2) - L(\lambda 2, x2, y2)|. \quad \text{Formula 13}$$

7. The image acquisition device according to claim 1,
wherein the measurement unit sets one of wavelengths of the emittable laser light as a reference wavelength, and at each of a wavelength that is higher than the reference wavelength and a wavelength that is lower than the reference wavelength, measures an intensity of the measurement target light that is based on laser light having the wavelength, and
wherein the control unit computes contrast of each of the intensity distribution of the measurement target light that is based on the laser light having the high wavelength and the intensity distribution of the measurement target light that is based on the laser light having the low wavelength and compares the contrast, and then controls the wavelength of the laser light to be one of the high wavelength and the low wavelength corresponding to the intensity distribution in which the computed contrast is high from the reference wavelength based on the comparison result.

8. The image acquisition device according to claim 7, wherein, by repeating the control of the wavelength of the laser light and the comparison of the contrast of the intensity distributions of the measurement target light that are based on the laser light having the high wavelength and the laser light having the low wavelength using the wavelength after the control as the reference wavelength, the control unit controls the wavelength of the laser light so that contrast of the intensity distribution of the measurement target light has a maximum value.

9. The image acquisition device according to claim 1, wherein the light source is configured to include a laser unit that outputs pump light having a predetermined frequency and an optical parametric oscillator and to be capable of controlling a wavelength of the laser light by controlling an oscillation condition of the optical parametric oscillator.

10. The image acquisition device according to claim 1, wherein the light source and the measurement unit are provided in the same housing.

11. The image acquisition device according to claim 1, wherein the measurement unit measures an intensity of laser light emitted from the light source, and
wherein the control unit executes at least one of control of the intensity of the laser light emitted from the light source and correction of intensity distribution of the measured measurement target light based on the measured intensity of the laser light.

12. An image acquisition method comprising:
scanning a sample using laser light emitted from a light source configured to be capable of controlling a wavelength of the laser light and measuring an intensity of measurement target light generated from the sample by receiving the laser light;
setting one of wavelengths of the emittable laser light as a reference wavelength;
measuring, at each of a wavelength that is higher than the reference wavelength and a wavelength that is lower than the reference wavelength, an intensity of the measurement target light that is based on laser light having the wavelength;
generating an image of the sample based on intensity distribution of the measured measurement target light;
computing contrast of each of the intensity distribution of the measurement target light that is based on the laser light having the high wavelength and the intensity distribution of the measurement target light that is based on the laser light having the low wavelength; and
controlling, based on comparing the contrast, a wavelength of the laser light based on the intensity distribution of the measured measurement target light to be one of the high wavelength and the low wavelength corresponding to the intensity distribution in which the computed contrast is high from the reference wavelength.

13. The image acquisition method according to claim 12, wherein, controlling the wavelength of the laser light further comprises, by repeating the control of the wavelength of the laser light and the comparison of the contrast of the intensity distributions of the measurement target light that are based on the laser light having the high wavelength and the laser light having the low wavelength using the wavelength after the control as the reference wavelength, controlling the wavelength of the laser light so that contrast of the intensity distribution of the measurement target light has a maximum value.

14. An image acquisition device comprising:
a light source configured to emit laser light and to be capable of controlling a wavelength of the laser light;
a measurement unit configured to scan a sample using the laser light and to measure an intensity of measurement target light from the sample by receiving the laser light, wherein the measurement unit sets one of wavelengths of the emittable laser light as a reference wavelength, and at each of a wavelength that is higher than the reference wavelength and a wavelength that is lower than the reference wavelength, measures an intensity of the measurement target light that is based on laser light having the wavelength; and
a control unit configured to generate an image of the sample based on intensity distribution of the measured measurement target light,
wherein the control unit controls a wavelength of the laser light based on the intensity distribution of the measured measurement target light and computes of each of the intensity distribution of the measurement target light that is based on the laser light having the high wavelength and the intensity distribution of the measurement target light that is based on the laser light having the low wavelength and compares the contrast, and then controls the wavelength of the laser light to be one of the high wavelength and the low wavelength corresponding to the intensity distribution in which the computed contrast is high from the reference wavelength based on the comparison result.

15. The image acquisition device according to claim 14, wherein, by repeating the control of the wavelength of the laser light and the comparison of the contrast of the intensity distributions of the measurement target light that are based on the laser light having the high wavelength and the laser light having the low wavelength using the wavelength after the control as the reference wavelength, the control unit controls the wavelength of the laser light so that contrast of the intensity distribution of the measurement target light has a maximum value.

16. The image acquisition device according to claim 14, wherein the light source is configured to include a laser unit that outputs pump light having a predetermined frequency and an optical parametric oscillator and to be capable of controlling a wavelength of the laser light by controlling an oscillation condition of the optical parametric oscillator.

17. The image acquisition device according to claim 14, wherein the light source and the measurement unit are provided in the same housing.

18. The image acquisition device according to claim 14, wherein the measurement unit measures an intensity of laser light emitted from the light source, and
wherein the control unit executes at least one of control of the intensity of the laser light emitted from the light source and correction of intensity distribution of the measured measurement target light based on the measured intensity of the laser light.

* * * * *